US010023632B2

(12) United States Patent
Sass et al.

(10) Patent No.: US 10,023,632 B2
(45) Date of Patent: Jul. 17, 2018

(54) ANTIGENIC GM-CSF PEPTIDES AND ANTIBODIES TO GM-CSF

(71) Applicant: Morphotek, Inc., Exton, PA (US)

(72) Inventors: Philip M. Sass, Audubon, PA (US); Nicholas C. Nicolaides, Glen Mills, PA (US); Luigi Grasso, Bryn Mawr, PA (US); Wolfgang Ebel, Plymouth Meeting, PA (US); Jian Li, Fort Washington, PA (US); Qimin Chao, Havertown, PA (US); Eric Routhier, Glen Mills, PA (US)

(73) Assignee: Morphotek, Inc., Exton, PA (US)

( * ) Notice: Subject to any disclaimer, the term of this patent is extended or adjusted under 35 U.S.C. 154(b) by 45 days.

(21) Appl. No.: 15/212,779

(22) Filed: Jul. 18, 2016

(65) Prior Publication Data

US 2016/0333089 A1    Nov. 17, 2016

Related U.S. Application Data

(60) Division of application No. 14/091,028, filed on Nov. 26, 2013, now Pat. No. 9,422,367, which is a continuation of application No. 13/629,165, filed on Oct. 24, 2012, now Pat. No. 8,623,364, which is a continuation of application No. 12/761,464, filed on Apr. 16, 2010, now Pat. No. 8,318,168, which is a division of application No. 11/672,902, filed on Feb. 8, 2007, now Pat. No. 7,741,450.

(60) Provisional application No. 60/771,251, filed on Feb. 8, 2006, provisional application No. 60/774,500, filed on Feb. 17, 2006.

(51) Int. Cl.
| | |
|---|---|
| *C07K 16/24* | (2006.01) |
| *C07K 16/22* | (2006.01) |
| *C12N 15/09* | (2006.01) |
| *C12N 15/13* | (2006.01) |
| *C12N 15/63* | (2006.01) |
| *C12P 21/08* | (2006.01) |
| *A61K 39/395* | (2006.01) |
| *C07K 16/00* | (2006.01) |

(52) U.S. Cl.
CPC ........ *C07K 16/243* (2013.01); *A61K 39/3955* (2013.01); *C07K 16/00* (2013.01); *C07K 16/22* (2013.01); *C12N 15/09* (2013.01); *C12N 15/63* (2013.01); *C07K 2317/21* (2013.01); *C07K 2317/33* (2013.01); *C07K 2317/34* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,164,369 A | 11/1992 | Cochrane et al. |
| 5,260,273 A | 11/1993 | Cochrane et al. |
| 5,407,914 A | 4/1995 | Cochrane et al. |
| 5,475,087 A | 12/1995 | Seelig et al. |
| 5,602,007 A | 2/1997 | Dunn et al. |
| 5,789,381 A | 8/1998 | Cochrane et al. |
| 5,891,429 A | 4/1999 | Clark et al. |
| 5,952,303 A | 9/1999 | Bornstein et al. |
| 6,013,619 A | 1/2000 | Cochrane et al. |
| 6,013,764 A | 1/2000 | Abdei-Magid et al. |
| 6,120,795 A | 9/2000 | Klimchak et al. |
| 6,135,430 A | 10/2000 | Bergman, Jr. et al. |
| 6,498,027 B1 | 12/2002 | VanEs et al. |
| 6,613,734 B2 | 9/2003 | Cochrane et al. |
| 7,108,852 B2 | 9/2006 | Devalaraja et al. |
| 7,381,801 B2 | 6/2008 | Renner et al. |
| 7,741,450 B2 | 6/2010 | Sass et al. |
| 7,867,495 B2 * | 1/2011 | Steidl .................. C07K 16/243 424/130.1 |
| 7,935,795 B2 | 5/2011 | Kannagi |
| 8,318,168 B2 | 11/2012 | Sass et al. |
| 2002/0010126 A1 | 1/2002 | Hamilton et al. |
| 2004/0053365 A1 * | 3/2004 | Renner ................ C07K 14/525 435/69.1 |
| 2004/0092717 A1 | 5/2004 | Carr et al. |
| 2006/0257359 A1 | 11/2006 | Francois et al. |
| 2008/0292641 A1 | 11/2008 | Sass et al. |

FOREIGN PATENT DOCUMENTS

| | | |
|---|---|---|
| AU | 2007-213716 | 6/2008 |
| EP | 0499161 A2 | 8/1992 |
| EP | 1593690 A1 | 11/2005 |

(Continued)

OTHER PUBLICATIONS

Argani et al., "Mesothelin is overexpressed in the Vast Majority of Ductal Adenocarcinomas of the Pancreas: Identification of a Few Pancreatic Cancer Marker by Serial Analysis of Gene Expression (SAGE)," Clin. Cancer Res., Dec. 2001, 7, 3862-3868.
Baritaki et al., "Generation of Human Anti-MUC3 1gG Antibodies After In Vitro Immunization of Naive Peripheral Blood-Lymphocytes," Cancer Immunol. Immunother., Apr. 2001, 50, 109-114.
Beffy et al., "An Immunodominant Epitope in a Functional Domain Near the N-terminus of Human Granulocyte-Macrophage C olony-Stimulating F actor Identified by C ross-Reaction of Synthetic Peptides With Neutralizing Anti-Protein and A nti-Peptide Antibodies," Hybridoma, Dec. 1994, 13(6), 457-468.
Bischof et al., "Exacerbation of Acute Inflammatory Arthritis by the Colony-Stimulating Factors CSF-1 and Granulocyte Macrophage (GM)-CSF: Evidence of Macrophage Infiltration and Local Proliferation," Clin. Exp. Immunol., Feb. 2000, 119, 361-367.
Blake et al., "Stepwise Deletions of P olyA Sequence in Mismatch Repair-Deficient Colorectal C ancers," Am. J. Pathol., May 2001, 158(5), 1867-1870.

(Continued)

*Primary Examiner* — Xiaozhen Xie
(74) *Attorney, Agent, or Firm* — Baker & Hostetler LLP

(57) ABSTRACT

Hybridoma lines that secrete human monoclonal antibodies with high binding specificity and biological activity, particularly neutralizing activity against granulocyte-macrophage colony stimulating factor, and methods of generating the hybridoma lines are provided. Target antigens and epitopes are also provided. The antibodies may be used in therapeutic methods, for example in the treatment of cancer, infectious disease, or autoimmune disease.

8 Claims, 15 Drawing Sheets

(56) References Cited

FOREIGN PATENT DOCUMENTS

| EP | 1598419 A1 | 11/2005 |
|---|---|---|
| JP | 2005-040126 | 2/2005 |
| JP | 2005-176792 | 7/2005 |
| JP | 2007-116947 | 5/2007 |
| WO | WO 89-06657 A1 | 7/1989 |
| WO | WO 92-22315 A1 | 12/1992 |
| WO | WO 98-49191 | 11/1998 |
| WO | WO 03-068924 A3 | 8/2003 |
| WO | WO 04-046330 A3 | 6/2004 |
| WO | WO 05-014652 A1 | 2/2005 |
| WO | WO 06-111353 A2 | 10/2006 |
| WO | WO 06-122797 A2 | 11/2006 |
| WO | WO 07-049472 A1 | 5/2007 |

OTHER PUBLICATIONS

Boerner et al., "Production of Antigen-Specific Human Monoclonal Antibodies From In Vitro-Primed Human Splenocytes," J. Immunol., Jul. 1991, 147, 86-95.
Bonfield et al., "Anti-GM-CSF Titer Predicts Response to GM-CSF Therapy in Pulmonary Alveolar Proteinosis," Clin. Immunol., Dec. 2002, 105(3), 342-350.
Burgess et al., "The Nature and Action of Granulocyte-Macrophage Colony Stimulating Factors," Blood, Dec. 1980, 56(6) 947-958.
Burgess et al., "Purification and Properties of Colony-Stimulating Factor From Mouse Lung-Conditioned Medium," J. Bioi. Chem., Mar. 1977, 252(6), 1998-2003.
Campbell et al., "Granulocyte-Macrophage Colony Stimulating Factor Exacerbates Collagen Induced Arthritis in Mice," Ann. Rheum. Dis., Jun. 1997, 56(6), 364-368.
Campbell et al., "Protection From Collagen-Induced Arthritis in Granulocyte-Macrophage Colony-Stimulating," J. Immunol., Oct. 1998, 161, 3639-3644.
Chang et al., "Molecular Cloning of Mesothelin, a Differentiation Antigen Present on Mesothelium, Mesotheliomas and Ovarian Cancers," Proc. Natl. Acad. Sci. USA, Jan. 1996, 93(1), 136-140.
Chothia et al., "Canonical Structures for Hypervariable Regions of Immunoglobulins," J. Mol. Bioi., Aug. 20, 1987, 196(4), 901-917.
Clackson et al., "Making antibody fragments using phage display libraries", Nature, Aug. 1991, 352,624-628.
Cook et al, "Blockade of Collagen-Induced Arthritis Post-Onset by Antibody to Granulocyte-Macrophage Colony-Stimulating Factor (GM-CSF): Requirement for GM-CSF in the Effector Phase of Disease", Arthritis Res. Jun. 2001, 3(5), 293-298.
Creighton et al., "Structures and Molecular Principles," Proteins, 1984, index only, 4 pages.
De Vries et al., "Flare-up of Rheumatoid Arthritis During GM-CSF Treatment After Chemotherapy," The Lancet, Aug. 24, 1991, 338(8765), 517-518.
Dempsey et al., "Monoclonal Antibodies That Recognize Human Granulocyte-Macrophage Colony-Stimulating Factor and Neutralize Its Bioactivity In Vitro," Hybridoma, Dec. 1990, 9(6), 545-558.
Eisenbarth et al., "Lipopolysaccharide-Enhanced, Toll-Like Receptor 4-Dependent T Helper Cell Type 2 Responses to Inhaled Antigen," J. Exp. Med., Dec. 16, 2002, 196(12), 1645-1651.
Emanuel, et al., "Selective Hypersensitivity to Granulocyte-Macrophage Colony-Stimulating Factor by Juvenile Chronic Myeloid Leukemia Hematopoietic Progenitors," Blood, Mar. 1, 1991, 77(5), 925-929.
Emanuel et al., "Juvenile Myelomonocytic Leukemia," Curr. Hematol. Rep., May 2004, 3(3), 203-209.
Fleetwood et al., "Functions of Granulocyte-Macrophage Colony-Stimulating Factor," Crit. Rev. Immunology, 2005, 25(5), 405-428.
Foote et al., "Antibody Framework Residues Effecting the Conformation of the Hypervariable Loop," J. Mol. Bioi., Mar. 20, 1992, 224(2), 487-499.
Gadi et al., "In Vivo Sensitization of Ovarian Tumors to Chemotherapy by Expression of E. coli Purine Nucleoside Phosphorylase in a Small Fraction of Cells," Gene Therepy, Oct. 2000, 7(20), 1738-1743.

Garmestani, et al., "Synthesis and Evaluation of a Macrocyclic Bifunctional Chelating Agent for Use With Bismuth Radionuclides," Nucl, Med, Bioi., May 2001, 28(4), 409-418.
Gajewska et al., "GM-CSF and Dendritic Cells in Allergic Airway Inflammation: basic mechanism and prospects for T herapeutic I ntervention," Curr. Drug Target Inflamm. Allergy, Dec. 2003, 2(4), 279-292.
Gamble et al., "Stimulation of the Adherence of Neutrophils to Umbilical Vein Endothelium by Human Recombinant Tumor Necrosis Factor," Proc. Natl. Acad. Sci. USA, Dec. 1985, 82(24), 8667-8671.
Grasso, et al., "Enhancing Therapeutic Antibodies and Titer Yields of Mammalian Cell Lines," BioProcess Int., Nov. 2004, 2(10), 58-64.
Hamilton "Colony Stimulating Factors, Cytokines and Monocyte-Macrophages—Some Controversies," Immunol. Today, Jan. 1993, 14(1), 18-24.
Hamilton, "Rheumatoid Arthritis: O pposing A ctions of H aematopoietic Growth Factors and Slow-Acting Anti-Rheumatic Drugs," Lancet, Nov. 1993, 342(8870), 536-539.
Hamilton et al., "Stimulation of Macrophage Plasminogen Activator Activity by Colony-Stimulating Factors," J. of Cellular Physiology, Jun. 1980, 103(3), 435-445.
Hamilton, "GM-CSF Inflammation and Autoimmunity," Trends in Immunol., Aug. 2002, 23,(8), 403-408.
Handman et al., "Stimulation by Granulocyte-Macrophage Colony-Stimulating Factor of Leishmania Tropica Killing by Macrophages," J. Immunol., Mar. 1979, 122(3), 1134-1137.
Hart et al., "Synergistic Activation of Human Monocytes by Granulocyte-Macrophage Colony-Stimulating Factor and IFN-y," J. Immunol., Sep. 1988, 141 (5), 1516-1521.
Hassan et al., "Mesothelin: A New Target for Immunotherapy," Clin. Cancer Res., Jun. 2004, 10(12 pt 1), 3937-3942.
Hazenberg et al., "Correction of Granulocytopenia in felty's Syndrome by Granulocyte-Macrophage Colony-Stimulating Factor, Simultaneous Induction of Interleukin-6 Release and Flare-Up of the Arthritis," Blood, Dec. 1989, 74(8), 2769-2770.
Irie et al., "Phase 1 pilot clinical trial of human IgM monoclonal antibody to ganglioside GM3 in patients with metastatic melanoma," Cancer Immunol. Immunother., Feb. 2004, 53(2), 110-117, Epublication Oct. 16, 2003.
Irie et al., "Regression of cutaneous Metastatic melanoma by intralesional injection with human monoclonal antibody to ganglioside GD2," Proc. Natl. Acad. Sci. USA, Nov. 1986, 83(22), 8694-8698.
Iversen et al., "Inhibition of Granulocyte-Macrophage Colony-Stimulating Factor Prevents Dissemination and Induces Remission of Juvenile Myelomonocytic Leukemia in Engrafted Immunodeficient Mice," Blood, Dec. 1997, 90(12), 4910-4907.
Jian et al., "Human Antibodies for Immunotherapy Development Generated Via a Human Cell Hybridoma Technology," PNAS, Mar. 27, 2006, 103(10), 3557-3562.
Jirholt et al., "Exploiting Sequence Space: Shuffling in Vivo Formed Complementarity Determining Regions Into a Master Framework," Gene, Jul. 1998, 215(2), 471-476.
Jones et al., "Replacing the complementarity-determining regions in a human antibody with those from a mouse," May 29-Jun. 4, 1986, 321(6069), 522-525.
Kay et al., "Messenger RNA Expression of the Cytokine Gene Cluster, Interleukin 3 (IL-3), IL-4, IL-5, and Granulocyte/Macrophage Colony-Stimulating Factor, in Allergen-Induced Later-Phase Cutaneous Reaction in Atopic Subjects," J.Exp. Med., Mar. 1991, 173, 775-778.
Kala et al., "Phage Displayed Antibodies to Heat Stable Alkaline Phosphatase: Framework Region as a Determinant of Specificity," J. Biochem. Oct. 2002, 132(4), 535-541.
Kaufman et al., "Selection and Coamplification of Heterologous Genes in Mammalian Cells," Meth Enzymology, 1990, 185, 537-567.
Kohler et al., "Continuous Cultures of Fused Cells Secreting Antibody of Predefined Specificity," Nature, Aug. 1975, 256(5517), 495-497.

(56) References Cited

OTHER PUBLICATIONS

Kohler et al., "Derivation of Specific Antibody-Producing Tissue Culture and Tumor Lines by Cell Fusion," Eur. J. Immunol., Jul. 1976, 6(7), 511-519.
Kirman et al., "Isolation of native human monoclonal autoantibodies to breast cancer," Hybrid & Hybridomics, Dec. 2002, 21(6), 405-414.
Knappik et al., "Fully Synthetic Human Combinatorial Antibody Libraries (HuCAL) Based on Modular Consensus Frameworks and CDRs Randomized With Trinucleotides", J. Mol. Bioi., Feb. 2000, 296(1), 57-86.
Kreitman et al., "Immunotoxins for Targeted Cancer Therapy," Adv. Drug Del. Rev., Apr. 1998, 31(1-2), 53-88.
Lang et al., "Transgenic Mice Expressing a Hemopoietic Growth Factor Gene (GM_CSF) Develop Accumulations of Macrophages, Blindness, and a Fatal Syndrome of Tissue Damage," Cell, Nov. 1987, 51(4), 675-686.
Lei et al., "Compartmentalized Transgene Expression of Granulocyte-Macrophage Colony-Stimulating Factor (GM-CSF) in Mouse Lung Enhances Allergic Airways I nflammation," Clin. Experimental Immunol., Aug. 1998, 113(2), 157-165.
Leizer et al., "Cytokine R egulation o f C olony-Stimulating F actor Production in Cultured Human Synovial Fibroblasts: I. Induction of GM-CSF and G-CSF Production by Interleukin-1 and Tumor Necrosis Factor," Blood, Nov. 1990, 76(10), 1989-1996.
Marks et al., By-Passing Immunization: Human Antibodies From V-Gene Libraries Displayed on Phage, J. Mol. Bioi., Dec. 1991, 222(3), 581-597.
Mazzone et al., "Our New Understanding of Pulmonary Alveolar Proteinosis: What an Internist Needs to Know," Clev. Clin. J. Med., Dec. 2001, 68(12), 977-993.
McQualter et al., "Granulocyte Macrophage Colony-Stimulating Factor: a New Putative Therapeutic Target in Multiple Sclerosis," J. Med., Oct. 2001, 194(7), 873-881.
Metcalf et al., "Hemopoietic Responses in Mice Infected With Purified Recombinant Murine GM-CSF," Exp. Hematol., Jan. 1987, 15(1), 1-9.
Morea et al., "Conformations Out of the Third Hypervariable Region in the VH D omain of Immunoglobulins," J. Mol. Bioi., Jan. 1998, 275(2), 269-294.
Morrison et al., "Chimeric Human Antibody Molecules: Mouse Antigen-Binding Domains With Human Constant Region Domains," Proc. Natl. Acad. Sci. USA, Nov. 1984, 81(21), 6851-6855.
Nice et al., "Human Granulocyte-Macrophage Colony-Stimulating Factor (hGM-CSF): Identification of a Binding Site for a Neutralizing Antibody," Growth Factors, Jan. 1990, 3(4), 159-169.
Nicolaides et al., "Morphogenics as a Tool for Target Discovery and Drug D evelopment," Ann. N.Y. Acad. Sci., Nov. 2005, 1059, 86-96.
Nicolaides et al., "A Naturally Occurring hPMS2 Mutation Can Confer a Dominant Negative Mutator Phenotype," Mol. Cell. Bioi., Mar. 1998, 18(3), 1635-1641.
Nicolaides et al., "Genomic Organization of the Human PMS2 Gene Family," Genomics, Nov. 1995, 30(2), 195-206.
Nishinakamura et al., "The Pulmonary Alveolar Proteinosis in Granulocyte Macrophage Colony-Stimulating Factor/Interleukins 3/5 Be Receptor-Deficient Mice is Reversed by Bone Marrow Transplantation," J. Exp. Med., Jun. 1996, 183(6), 2657-2662.
Okayama et al., "A eDNA Cloning Vector That Permits Expression of eDNA Inserts in Mammalian Cells," Mol. Cell. Bioi., Feb. 1983, 3(2), 280-289.
Panka et al., "Variable Region Framework Difference Result in Decreased or Increased AffinityOf Variant Anti-Digoxin Antibodies," Proc. Natl. Acad. Sci. USA, May 1988, 85(9), 3080-3084.
Perkins et al., "Effects of Continuous High Dose rhGM-CSF Infusion of Human Monocyte Activity," Am. J. Hematol., Aug. 1993, 43(4), 279-285.
Plater-Zyberk et al, "GM-CSF Neutralisation Suppresses Inflammation and Protects Cartilage in Acute Streptococcal Cell Wall Arthritis of Mice", Ann Rheum Dis., 2007, 66, 452-457.

Portolano et al., "Lack of Promiscuity in Autoantigen-Specific H and L Chain Combinations as revealed by human Hand L chain 'Roulette'", J. Immunol., Feb. 1993, 150(3), 880-887.
Potter et al., "Enhancer-Dependent Expression of Human k Immunoglobulin Genes Introduced Into Mouse pre-B Lymphocytes by Electroporation," Proc. Natl. Acad. Sci. USA, Nov. 1984, 81(22), 7161-7165.
Presta, L. G., "Antibody Engineering," Current Opin in Biotech., Aug. 1992, 2, 593-596.
Reed et al., "Aerosolized GM-CSF A meliorates P ulmonary A lveolar P roteinosis in GM-CSF-Deficient Mice," Am. J. Physiol., Apr. 1999, 276(4 Pt 1), L556-L573.
Reichmann et al., "Reshaping Human Antibodies for Therapy," Nature, Mar. 1988, 332(6162), 323-329.
Schaffner et al., "Direct Transfer of Cloned Genes From Bacteria to Mammalian cells," Proc. Natl. Acad. Sci. USA, Apr. 1980, 77(4), 2163-2167.
Seki et al., "Type II Collagen-Induced Murine Arthritis: I. Induction and Perpetuation of Arthritis Require Synergy Between Humoral and Cell-Mediated Immunity," J. Immunol., Mar. 1988, 140(5), 1477-1484.
Selgas et al., "Immunomodulation of Peritoneal Macrophages by Granulocyte-Macrophages Colony-Stimulating Factor in Humans," Kidney Int., Dec. 1996, 50(6), 2070-2078.
Söderland et al., "Recombining Germline-Derived CDR Sequences for Creating Diverse Single-Framework Antibody Libraries," Nature Biotechnology, Aug. 2000, 18(8), 852-856.
Shah et al., "Pulmonary Alveolar Proteinosis: Clinical Aspects and Current Concepts on Pathogenesis," Thorax, Jan. 2000, 55(1), 67-77.
Shinkawa et al., "The Absence of Fucose But Not the Presence of Galactose or Bisecting M-acetylglucosamine of Human IgG1 Complex-Type Oligosaccharides Shows the Critical Role of Enhancing Antibody-Dependent Celluar Cytotoxicty," J. Bioi. Chem., Jan. 31, 2003, 278(5), 3466-3473.
Stanley et al., "Granulocyte/macrophage Colony-Stimulating Factor-Deficient Mice Show No Major Perturbation of Hematopoiesis But Develop a Characteristic Pulmonary Pathology," Proc. Natl. Acad. Sci. USA, Jun. 1994, 91, 5592-5596.
Takahashi et al., "Effect of Granulocyte-Macrophage Colony-Stimulating Factor and Interleukin-3 on Interleukin-8 Production by Human Neutrophils and Monocytes," Blood, Jan. 1993, 81(2), 357-364.
Tien-Wen et al., "Peripheral Blood Lymphocytes From Normal Individuals Can Be Induced to Secrete Immunoglobulin G Antibodies Against Self-Antigen Thyroglobulin In Vitro," J. Clin. Endocrinol. Metab., Feb. 1985, 60(2), 279-282.
Thomas et al., "Mesothelin-specific CDS+T Cell Responses Provide Evidence of In Vivo Cross-Priming by Antigen-Presenting Cells in Vaccinated Pancreatic Cancer Patient," J. Exp. Med., Aug. 2004, 200(3), 297-306.
Van Dijk et al., "Human Antibodies As Next Generation Therapeutics," Curr. Opin. Chem. Biol., Aug. 2001, 5(4), 368-374.
Williamson et al., "The Detection and Initial Characterization of Colony-Stimulating Factors in Synovial Fluid," Clin. Exp. Immunol., Apr. 1988, 72(1), 67-73.
Wooley, P., "Collagen-Induced Arthritis in the Mouse," Methods Enzymol., 1988, 162, 361-373.
Xu et al., "Cytokines in Chronic Inflammatory Arthritis. II. Granulocyte-Macrophage Colony-Stimulating Factor in Rheumatoid Synovial Effusions," J. Clin. Invest., Mar. 1989, 83(3), 876-882.
Yamashita et al., "Attenuation of Airway Hyperresponsiveness in a Murine Asthma Model by Neutralization of Granulocyte-Macrophage Colony-Stimulating F actor (GM-CSF)," Cell Immunol., Oct. 2002, 219, 92-97.
Yang, Y. and Hamilton, J., "Dependence of Interleukin-1—Induced Arthritis on Granulocyte—Macrophage Colony-Stimulating Factor", Arthritis & Rheumatism, 44(1), Jan. 2001, 111-119.
Yuzuru et al., "Identification of Functionally Distinct Domains of Human Granulocyte-Macrophage Colony-Stimulating Factor Using Monoclonal Antibodies," Blood, Mar. 1, 1991, 77(5), 1033-1043.

(56) References Cited

OTHER PUBLICATIONS

Zafiropoulos et al., "Induction of Antigen-Specific Isotype Switching by In Vitro Immunization of Human naTve B Lymphocytes," J. Immunol. Methods, Jan. 1997, 200(1-2), 181-190.

Zsengaller et al., "Adenovirus-Mediated Granulocyte-Macrophage Colony-Stimulating Factor Improves Lung Pathology of Pulmonary Alveolar Proteinosis in Granulocyte-Macrophage Colony-Stimulating Factor-Deficient Mice," Hum. Gene Ther., Sep. 1998, 9(14), 2101-2109.

Van Djik et al., "Human Antibodies As Next Generation Therapeutics," Current Opinion in Chemical Biology, Aug. 2001 5(4), 368-374.

Kanakura et al., "Identification of Functionally Distinct Domains of Human Granulocyte-Macrophase Colony-Stimulating Factor Using monoclonal Antibodies," Blood, Mar. 1991, 77(5), 1033-1043.

\* cited by examiner

```
CSISAPARSPSPSTQPWEHVNAIQEARRLLNLSRDTAAEMNETVEVISEMPDLQEPTCLQTRLELYKQGLRGSLTKLKGPLT
CSISAPARSPSP (12)
    PARSPSPSTQPW (12)
        SPSTQPWEHVNA (12)
            PWEHVNAIQEAR (12)
                NAIQEARRLLNL (12)
                    ARRLLNLSRDTA (12)
                        NLSRDTAAEMNE (12)
                            TAAEMNETVEVI (12)
                                NETVEVISEMPD (12)
                                    VISEMPDLQEPT (12)
                                        FDLQEPTCLQTR (12)
                                            PTCLQTRLELYK (12)
                                                TRLELYKQGLRG (12)
                                                    YKQGLRGSLTKL (12)
                                                        RGSLTKLKGPLT (12)

ELKGPLTMMASHYKQHCPPTPETSCATQIITPESFKENLKDFLLVIPFDCWEPVQE
ELKGPLTMMASH (12)
    LTMMASHYKQHC (12)
        SHYKQHCPPTPE (13)
            HCPPTPETSCAT (12)
                PETSCATQIITF (12)
                    ATQIITPESFKE (12)
                        TPESFKENLKDF (13)
                            KENLKDFLLVIP (12)
                                DFLLVIPFDCWE (12)
                                    IPFDCWEPVQE (12)
```

Figure 14

| Peptide Number | Sequence |
|---|---|
| 1 | CSISAPARSPSP |
| 2 | PARSPSPSTQPW |
| 3 | SPSTQPWEHVNA |
| 4 | PWEHVNAIQEAR |
| 5 | NAIQEARRLLNL |
| 6 | ARRLLNLSRDTA |
| 7 | NLSRDTAAEMNE |
| 8 | TAAEMNETVEVI |
| 9 | NETVEVISEMFD |
| 10 | VISEMFDLQEPT |
| 11 | FDLQEPTCLQTR |
| 12 | PTCLQTRLELYK |
| 13 | TRLELYKQGLRG |
| 14 | YKQGLRGSLTKL |
| 15 | RGSLTKLKGPLT |
| 16 | KLKGPLTMMASH |
| 17 | LTMMASHYKQHC |
| 18 | SHYKQHCPPTP |
| 19 | HCPPTPETSCA |
| 20 | PETSCATQIIT |
| 21 | ATQIITFESFK |
| 22 | TFESFKENLKDF |
| 23 | KENLKDFLLVIP |
| 24 | DFLLVIPFDCWE |
| 25 | IPFDCWEPVQE |
| 26 | GEQKLISEEDLG |

Figure 15

ANTIGENIC GM-CSF PEPTIDES AND ANTIBODIES TO GM-CSF

CROSS-REFERENCE TO RELATED APPLICATIONS

This application is a divisional application of U.S. application Ser. No. 14/091,028, filed Nov. 26, 2013, now U.S. Pat. No. 9,422,367, which is a continuation of U.S. application Ser. No. 13/659,165, filed Oct. 24, 2012, now U.S. Pat. No. 8,623,364, which is a continuation of U.S. application Ser. No. 12/761,464, filed Apr. 16, 2010, now U.S. Pat. No. 8,318,168, which is a divisional application of U.S. application Ser. No. 11/672,902, filed Feb. 8, 2007, now U.S. Pat. No. 7,741,450, which claims benefit of U.S. Provisional Application Nos. 60/771,251, filed Feb. 8, 2006, and 60/774,500, filed Feb. 17, 2006. The contents of each of these applications are incorporated by reference herein.

SEQUENCE LISTING

The instant application contains a Sequence Listing which has been submitted electronically in ASCII format and is hereby incorporated by reference in its entirety. Said ASCII copy, created on Jul. 14, 2016, is named 104018.000955_SL.txt and is 49,267 bytes in size.

FIELD

The invention relates generally to the field of immunotherapeutics. More specifically, the invention relates to antigens for generating monoclonal antibodies, and monoclonal antibodies that can neutralize autoimmune and cancer cells, and can neutralize the inflammatory response.

BACKGROUND

Various publications, including patents, published applications, technical articles and scholarly articles are cited throughout the specification. Each of these cited publications is incorporated by reference herein, in its entirety and for all purposes Several disease-associated antigens are currently being targeted using therapeutic monoclonal antibodies (MAbs) because of their unique pharmacological and safety profiles. Among the disease-associated target antigens are CD20, Tumor Necrosis Factor alpha (TNF-α), Epidermal Growth Factor Receptors (EGFR), and granulocyte-macrophage colony stimulating factor.

Granulocyte macrophage-colony stimulating factor (GM-CSF) was originally discovered as a protein with the capacity to generate both granulocyte and macrophage colonies from precursor cells in mouse bone marrow, and was accordingly named (Burgess et al. (1980) Blood 56:947-58.). Subsequent studies have demonstrated a role of GM-CSF in potentiating the function of mature macrophages and granulocytes (Handman and Burgess (1979) J. Immunol. 122: 1134-1137; Hamilton et al. (1980) J. Cell Physiol. 103:435-445; Gamble et al. (1985) Proc. Natl. Acad. Sci. USA 82:8667-8671), suggesting a role for GM-CSF in inflammatory responses (Hamilton et al. (1980) J. Cell Physiol. 103:435-445). As the molecule was studied it became clear that GM-CSF has other functions arising from its ability to affect the properties of more mature myeloid cells such as granulocytes, macrophages and eosinophils. The functions of GM-CSF are mediated by binding to CD116, the granulocyte-macrophage colony stimulating factor receptor, also known as colony stimulating factor 2 receptor alpha that binds GM-CSF with low affinity. The beta subunit, called CD131, which is also shared with the IL3 and IL5 receptors, has no detectable binding activity for GM-CSF by itself but is necessary for high affinity binding when in association with the alpha subunit and plays a fundamental role in signal transduction. The GM-CSF receptors are found on myeloid progenitors and mature myeloid cells including neutrophils, eosinophils, mononuclear phagocytes, and monocytes. In addition, GM-CSF receptor subunits have been shown to be present in normal, non-hematopoietic tissues such as human placenta, endothelium, and oligodendrocytes of the central nervous system.

GM-CSF plays a major biological role in the generation of granulocytes and macrophages from early bone marrow progenitors within the bone marrow. What was not appreciated at first but later uncovered was additional physiological functions of GM-CSF in host responses to external stimuli and in inflammatory and autoimmune conditions. In very early studies, GM-CSF was purified from lung tissue-conditioned medium following lipopolysaccharide (LPS) injection into mice (Burgess et al. (1977) J. Biol. Chem. 252:1998-2003). GM-CSF is considered by many investigators to be one of the major regulators of granulocyte, macrophage and eosinophil lineage cell number and activation state under normal physiological conditions. However, it has also been hypothesized that aberrant expression of GM-CSF may lead to altered immune and inflammatory responses with associated pathologic consequences. It was suggested several years ago that GM-CSF should be viewed as a proinflammatory cytokine (Hamilton et al., 1980, J. Cell Physiol. 103:435-445). Furthermore, GM-CSF may play a role in the diathesis of a multitude of human inflammatory pathologies, such as rheumatoid arthritis, autoimmune pathologies, inflammatory renal disease and inflammatory lung disorders such as asthma and chronic obstructive pulmonary disease (COPD). Interestingly, it has been proposed that there is a link between multiple sclerosis and GM-CSF (McQualter et al. (2001) J. Exp. Med., 194:873-881). In an experimental model of autoimmune encephalomyelitis, a model for multiple sclerosis, GM-CSF was found to be involved in the autoimmune-mediated demyelination.

In vivo studies following monocyte, macrophage and neutrophil treatment with GM-CSF have demonstrated that GM-CSF can activate these cell types and prolong their survival characteristics. Moreover, GM-CSF exposure results in release of inflammatory mediators from these cell types, and further studies have demonstrated the ability of these cells to kill certain organisms and even tumor cells (Hamilton (1993) Immunol. Today 14:18-24; Hamilton, (1993) Lancet 342:536-539; Takahashi, (1993) Blood 81:357-364). To determine if the in vivo studies were indicative of the function of GM-CSF in vivo, systemic administration was performed with rodents. It was shown that artificially increasing circulating levels of GM-CSF by intraperitoneal administration of the protein did result in increased numbers of both circulating neutrophils and cycling peritoneal macrophages and that there was an increase in the development and differentiation of CD5+ macrophages in the peritoneal cavity of rodents (Metcalf et al., (1987) Exp. Hematol. 15:1-9).

It has also been shown that GM-CSF can "prime" cells to respond in a more robust, synergistic manner to a second stimulus, such as LPS or interferon-gamma (Hart et al., 1988, J. Immunol. 141:1516-1521). Mice can be primed both in vitro as well as in vivo with GM-CSF so that they produce increased levels of circulating pro-inflammatory cytokines following subsequent challenge with LPS or TNF-alpha.

In a clinical setting, administration of GM-CSF into peritoneal dialysis patients resulted in a marked recruitment of macrophages (Selgas et al., 1996, Kidney Int. 50:2070-2078). Interestingly, and as predicted from the rodent studies, administration of GM-CSF in a clinical setting can result in accentuated production of inflammatory cytokines and potential unwanted side effects. For example, when patients with rheumatoid arthritis were treated with GM-CSF to correct the neutropenia associated with Felty's syndrome, their arthritis was exacerbated (Hazenberg et al., 1991, Blood 74:2769-2770). In another clinical setting, following cancer chemotherapy, GM-CSF treatment made rheumatoid arthritis worse (de Vries et al., (1991) J. Immunol. 163: 4985-4993). Systemic administration of GM-CSF to human donors increased the ability of isolated granulocytes to produce superoxide, and both accentuated the cytotoxicity of circulating monocytes as well as led to an increase in the number of monocytes (Perkins et al., 1993, Am J. Hematol. 43:279-285). Aberrant expression of GM-CSF is associated with disease of the lung in human as well. For example, it appears that upregulation of GM-CSF in the lung by minor irritants, endotoxins or infections predisposes towards TH2 immune deviation and asthma (Eisenbarth et al. (2002) J. Exp. Med. 196:1645-1651). The studies summarized above suggest that GM-CSF plays a role in the activation of the inflammatory process through cell recruitment, increased cell survival and/or priming for activation.

Several association and experimental data suggest a role for GM-CSF in asthma. The use of neutralizing antibodies in a mouse model of asthma have demonstrated the ability to suppress asthmatic phenotypes (Yamashita (2002) Cell Immunol. 219:92), while several studies measuring cytokines in BAL fluid of asthmatic patients have found an increase in GM-CSF (Gajewska (2003) Curr Drug Targets Inflamm Allergy 2:279).

Rheumatoid arthritis (RA) is a chronic inflammatory autoimmune disease for which there is ample evidence that GM-CSF may be involved. GM-CSF has been found at elevated levels in RA lesions (Xu et al. (1989) J. Clin. Invest. 83:876) and is produced in vitro by resident joint cells (chondrocytes and synovial fibroblasts) following their stimulation with inflammatory cytokines such as IL-1 and TNF-alpha (Leizer et al. (1990) Blood 76:1989). Collagen-induced arthritis (CIA) in the mouse is an autoimmune model of RA that is dependent upon both humoral and cellular immune responses to type II collagen (CII) (Seki et al. (1988) J. Immunol. 140, 1477). Historically this RA phenotype is restricted to mouse strains bearing the H-2q or H-2r haplotypes and is generally performed in DBA/1 mice (Wooley (1988) Methods Enzymol. 162:361). A series of studies were performed in transgenic mice that were homozygous null for the murine GM-CSF locus (Stanley et al. (1994) Proc. Natl. Acad. Sci. USA 91:5592). Interestingly, the GM-CSF-deficient mice are resistant to the induction of collagen-induced arthritis as compared to their wild-type control litter mates (Campbell et al. (1998) J. Immunol. 161:3639-3644).

Of further interest is that GM-CSF null mice have impaired surfactant clearance that leads to murine pulmonary alveolar proteinosis (PAP), which closely mimics the human condition as described herein. Moreover, the PAP phenotype can be corrected by lung-specific delivery of the GM-CSF gene (Zsengaller et al. (1998) Hum. Gene Ther. 9:2101-2109), aerosolization of GM-CSF or bone marrow transplantation for hematopoeitic reconstitution (Reed et al. (1999) Am. J. Physiol. 276:L556-L563; Nishinakamura et al. (1996) J. Exp. Med. 183:2657-2662).

Adult human pulmonary alveolar proteinosis (PAP) is a rare disease characterized by the accumulation of phospholipids and surfactant proteins in the alveoli. It has been hypothesized that PAP is due to the inability of the alveolar macrophages and type II epithelial cells to clear excess surfactant (Mazzone et al. (2001) Clev. Clin. J. Med. 68:977-992). The diagnosis of PAP generally requires an open lung biopsy and the standard therapy for the disease is physical removal of the accumulated surfactant by whole-lung lavage (Shah et al. (2000) Thorax 55:67-77). Furthermore, patients with PAP have been shown to have circulating, neutralizing antibodies to GM-CSF, thereby implicating this cytokine as causative of the disease. Whether this autoimmune response is specific for GM-CSF is unclear. However, it has been shown that a subset of PAP patients improve with GM-CSF therapy, supporting the hypothesis that the absence of GM-CSF either by gene disruption or antibody-mediated neutralization results in the development of PAP.

There is also evidence to support a role for GM-CSF in cancer. For example, GM-CSF plays a role in the genesis and progression of leukemias, such as juvenile myelomonocytic leukemia (JMML); Emanuel P D (2004) Curr. Hematol. Rep. 3:203-209). JMML is characterized by disruption of normal hemopoiesis resulting in excessive, inappropriate proliferation of immature myeloid cells in the bone marrow. These proliferating hematopoietic cancer cells can metastasize to the spleen and liver. Interestingly, patients with JMML are hypersensitive to GM-CSF and exhibit pathologic features similar to those in transgenic mice that overexpress GM-CSF (Lang et al. (1987) 51:675-86). Furthermore, GM-CSF has been shown to promote JMML cell growth and survival (Emanuel et al. (1991) Blood 77:925-9). In the transgenic mouse model of JMML, blockade of GM-CSF reduced JMML cell burden in the bone marrow, blood and spleen (Iversen et al. (1997) Blood, 90:4910-7).

It is clear from murine disease models in which GM-CSF is knocked-out as well as human diseases such as PAP in which circulating antibodies are generated in the systemic circulation to GM-CSF that this cytokine is an important mediator of pathology. Therefore an approach to develop a drug that can antagonize the activity of GM-CSF, either by developing an antibody to the cytokine itself or by blockade of the GM-CSF receptor, may be a valuable human therapeutic. Several polyclonal and monoclonal antibodies have been generated to the recombinant GM-CSF molecule. For example, Beffy et al. ((1994), Hybridoma 13:457-468), generated polyclonal antibodies to recombinant human GM-CSF in New Zealand White rabbits and monoclonal antibodies in Balb/c mice. These rabbit and some of the murine monoclonal antibodies were capable of neutralizing the activity of GM-CSF in an in vitro cell proliferation assay with MO7e cells. In further studies, Nice et al. (1990, Growth Factors 3, 159-169) epitope-mapped the binding site of one neutralizing murine anti-GM-CSF antibody, LMM102. A well-defined epitope was delineated by generating a series of digestion products from recombinant, human GM-CSF, using reverse phase HPLC fractionation to separate the fragments, followed by additional S. aureus V8 digestion of the tryptic fragments to define a product comprising two peptides linked by a disulphide bond. Three murine antibodies to human GM-CSF were generated by Dempsey et al. (1990, Hybridoma 9, 545-558) that neutralized GM-CSF in an in vitro assay system with an EC50 in the 0.1 to 1.7 nanomolar range. These antibodies did not react with murine GM-CSF or other related cytokines. All of the above-described antibodies are useful reagents for the detection of GM-CSF in human serum as well as for in vitro assays to inhibit GM-CSF signaling. However, all of these antibodies have little value as therapeutics due to the fact that they are derived from either a murine or rabbit system. Attempts have been made to generate chimeric antibodies from murine counterparts by subcloning the variable domain from the murine anti-GM-CSF antibody into a human backbone. This strategy has led to a chimeric antibody that can neutralize GM-CSF in vitro and may be useful as a therapeutic (WO 03/068924 A2).

An important aspect of a therapeutic antibody is its ability to elicit immune effector functions, such as antibody dependent cellular cytotoxicity (ADCC). Rodent MAbs, for example, have been shown to poorly mediate effector functions in humans because of sequence differences in the Fc region and therefore chimerization or humanization are required to gain optimal pharmacological properties. In addition, MAbs with fully human sequences may still fail to support ADCC if they are produced in non-human host cells that may alter native glycosylation pattern of MAbs (Shinkawa et al. (2003) J. Biol. Chem. 278:3466-73).

In view of these facts, production of therapeutic antibodies by human B-cells is preferred. Methods for generation of hybridomas secreting human MAbs have been previously reported (WO2004/046330). Therapeutic MAbs generated by human B-cells are able to exert human effector functions and have very limited immunogenicity because of their native human structure. The generation of hybridoma or Epstein-Barr virus (EBV)-transformed lymphoblastoid lines derived from human B-cells has been previously reported (Kirman et al. (2002) Hybrid Hybridomics 21:405-14; Boemer et al. (1991) J. Immunol. 147:86-95; Zafiropoulos et al. (1997) J. Immunol. Methods 200:181-90); however, information on the characterization of these antibodies and the lines with respect to their long term stability, suitability to manufacturing processes, and the antibody's pharmacological properties is limited (van Dijk et al. (2001) Curr. Opin. Chem. Biol. 5:368-74).

There is thus a need for therapeutic human antibodies for the treatment of inflammation associated with infectious, inflammatory diseases, autoimmune disorders, and other diseases such as cancer. It is further desired that such antibodies would elicit immune effector functions, as well as be well-tolerated in human patients. The present invention addresses these and other long felt needs.

SUMMARY

The invention features isolated human antibodies that specifically bind to GM-CSF. The antibodies can comprise a heavy chain CDR3 having SEQ ID NO:42 or 48. In some preferred embodiments, the antibodies can comprise a heavy chain having SEQ ID NO:8 or 16. In some preferred embodiments, the antibodies can comprise a light chain having SEQ ID NO: 12 or 18. In some embodiments, the antibodies have two heavy chains. In some embodiments, the antibodies have two light chains. The antibodies are high affinity antibodies, and can have an affinity of less than about $1 \times 10^{-8}$ M. Preferably, the antibodies are monoclonal antibodies, and more preferably, are human monoclonal antibodies. In highly preferred embodiments, the antibodies specifically bind to an epitope on a polypeptide comprising the amino acid sequence SEQ ID NO:3, 4, 5, 35, 36, 37, 38, or 39. Cells that express such antibodies, such as hybridoma cells are also provided.

The invention also features polynucleotides that encode antibodies that specifically bind to GM-CSF. In some preferred embodiments, the polynucleotides comprise a heavy chain sequence of SEQ ID NO:10 or 17. In some preferred embodiments, the polynucleotides comprise a light chain sequence of SEQ ID NO: 14 or 19. Vectors comprising such polynucleotides are also provided.

The invention also features methods for treating GM-CSF-mediated inflammatory disease in a subject in need of such treatment. The methods comprise administering to the subject a composition comprising a pharmaceutically acceptable carrier and at least one antibody that specifically binds to GM-CSF in an amount effective to treat a GM-CSF-mediated inflammatory disease. In preferred aspects of these methods, the antibodies can comprise a heavy chain CDR3 having SEQ ID NO:42 or 48. In some preferred embodiments, the antibodies can comprise a heavy chain having SEQ ID NO:8 or 16. In some preferred embodiments, the antibodies can comprise a light chain having SEQ ID NO: 12 or 18. The antibodies are high affinity antibodies, and can have an affinity of less than about $1 \times 10^{-8}$ M.

BRIEF DESCRIPTION OF THE DRAWINGS

As shown in FIG. 2A, soluble human GM-CSF was bound to murine hybridoma cells presenting cell surface immunoglobulin (Ig) to human GM-CSF. MAb E5 was subsequently added to the reaction and its binding to human GM-CSF measured using FITC-conjugated goat anti-human Ig. E5 did not bind any of the surface proteins expressed by the murine hybridoma cells (middle panel) but only bound soluble GM-CSF captured by the cell surface Ig (lower panel). As shown in FIG. 2B, phycoerythrin (PE)-labeled human GM-CSF (PE-GM) can react to Ig expressed on E10 cell surface. Excess of unlabeled GM-CSF (bottom panel) competed for PE-GM binding.

FIG. 14 illustrates a strategy to map G9 epitope. Overlapping peptides used to map G9 epitope binding location correspond to amino acid sequences of SEQ ID NOs: 35-38, and 64-85.

FIG. 15 shows G9 epitope mapping analysis using Western blot analysis with overlapping peptides that cover human GM-CSF protein sequence corresponding to amino acid sequences of SEQ ID NOs: 35-38, and 65-86. Antibody positive peptides include SEQ ID NO: 35-38.

DETAILED DESCRIPTION OF ILLUSTRATIVE EMBODIMENTS

Figure 1:
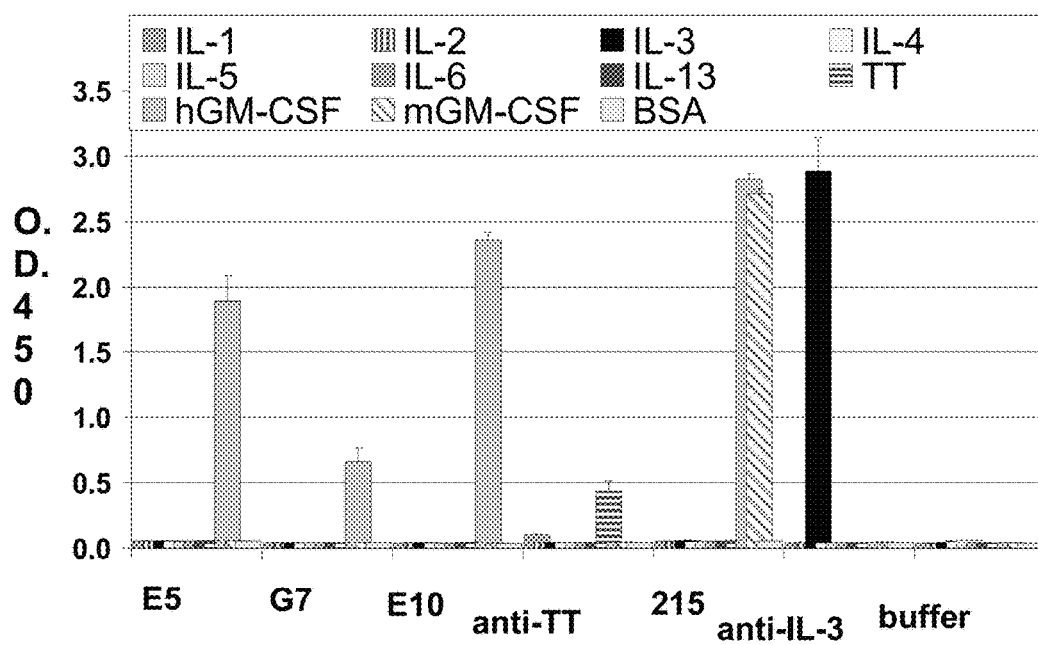
FIG. 1 illustrates the antigen panel ELISA for selection of antigen-specific human MAbs. Three GM-CSF-specific human MAbs (E5, G7, E10), reacted with human GM-CSF and none of the other antigens in the panel. Antibody 215 is a murine MAb that binds to human GM-CSF (hGM-CSF) and murine GM-CSF (mGM-CSF).

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

It is to be understood that this invention is not limited to particular methods, reagents, compounds, compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes a combination of two or more cells, and the like.

Each range recited herein includes all combinations and sub-combinations of ranges, as well as specific numerals contained therein.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Infectious disease" includes, but is not limited to, infection with a pathogen, virus, bacterium, fungus or parasite. Examples of viruses include, but are not limited to, severe acute respiratory syndrome (SARS; caused by SARS-associated coronavirus), hepatitis type B or type C, influenza, varicella, adenovirus, herpes simplex virus type I or type II, rinderpest, rhinovirus, echovirus, rotavirus, respiratory syncytial virus, papilloma virus, papova virus, cytomegalovirus, echinovirus, arbovirus, hantavirus, coxsachie virus, mumps virus, measles virus, rubella virus, polio virus, and human immunodeficiency virus (HIV) type I or type II. Examples of bacteria include, but are not limited to, Ebola, *Staphylococcus* A-E, *Plasmodium* (malaria), *M. tuberculosis, mycobacterium, mycoplasma, neisseria* and *legionella*. Examples of parasites include, but are not limited to, *rickettsia* and *chlamydia*.

"Inflammatory diseases" include, but are not limited to, acute and chronic immune and autoimmune pathologies, such as, but not limited to, rheumatoid arthritis, autoimmune disease, inflammatory renal disease and inflammatory lung disorders such as asthma and chronic obstructive pulmonary disease (COPD), multiple sclerosis, and autoimmune encephalomyelitis.

An "autoimmune disease" is a disease or disorder arising from and directed against an individual's own tissues or a co-segregate or manifestation thereof or resulting condition therefrom. Examples of autoimmune diseases include, but are not limited to arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, non-granulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, allergic reaction, eczema including allergic or atopic eczema, asteatotic eczema, dyshidrotic eczema, and vesicular palmoplantar eczema, asthma such as asthma bronchiale, bronchial asthma, and autoimmune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus, juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, diabetic retinopathy, diabetic nephropathy, diabetic large-artery disorder, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis, large-vessel vasculitis (including polymyalgia rheumatica and giant-cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Behcet's disease/syndrome, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, thermal injury, preeclampsia, an immune complex disorder such as immune complex nephritis, antibody-mediated nephritis, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP), post-transfusion purpura (PTP), heparin-induced thrombocytopenia, and autoimmune or immune-mediated thrombocytopenia such as idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant-cell hepatitis, chronic active hepatitis or autoimmune chronic active hepatitis, lymphoid interstitial pneumonitis (LIP), bronchiolitis obliterans (non-transplant) vs NSIP, Guillain-Barre syndrome, Berger's disease (IgA nephropathy), idiopathic IgA nephropathy, linear IgA dermatosis, acute febrile neutrophilic dermatosis, subcomeal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia areata, alopecia totalis, CREST syndrome (calcinosis, Raynaud's phenomenon, esophageal dysmotility, sclerodactyly, and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis, endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant-cell polymyalgia, chronic hypersensitivity pneumonitis, keratoconjunctivitis sicca, epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, non-malignant thymoma, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, autoimmune polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism, neurological disease, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, and endometriosis.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

"Recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "nucleic acid" or "polynucleotide sequence" refers to a single or double-stranded polymer of deoxyribonucleotide or ribonucleotide bases read from the 5' to the 3' end. Nucleic acids can also include modified nucleotides that permit correct read through by a polymerase and do not alter expression of a polypeptide encoded by that nucleic acid, including, for example, conservatively modified variants.

"Polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. Polypeptides of the invention include conservatively modified variants. One of skill will recognize that substitutions, deletions or additions to a nucleic acid, peptide, polypeptide, or protein sequence which alter, add or delete a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (33). The term "conservative substitution" also includes the use of a substituted amino acid in place of an unsubstituted parent amino acid provided that such a polypeptide also displays the requisite binding activity.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analog" refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones but retain the same basic chemical structure as a naturally occurring amino acid. "Amino acid mimetic" refers to a chemical compound having a structure that is different from the general chemical structure of an amino acid but that functions in a manner similar to a naturally occurring amino acid.

Amino acids can be referred to herein by either their commonly known three letter symbols or by the one-letter symbols recommended by the IUPAC-IUB Biochemical Nomenclature Commission (see Table 1 below). Nucleotides, likewise, can be referred to by their commonly accepted single-letter codes.

TABLE 1

| SYMBOL | | |
| --- | --- | --- |
| 1-Letter | 3-Letter | AMINO ACID |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

It should be noted that all amino acid sequences are represented herein by formulae whose left to right orientation is in the conventional direction of amino-terminus to carboxy-terminus.

As used herein, the term "in vitro" or "ex vivo" refers to an artificial environment and to processes or reactions that occur within an artificial environment, for example, but not limited to, test tubes and cell cultures. The term "in vivo" refers to a natural environment (e.g., an animal or a cell) and to processes or reactions that occur within a natural environment.

"Pharmaceutically acceptable," "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

The term "pharmaceutically acceptable carrier" refers to reagents, excipients, cells, compounds, materials, compositions, and/or dosage forms which are, within the scope of sound medical judgment, suitable for use in contact with the tissues of human beings and animals without excessive toxicity, irritation, allergic response, or other complication commensurate with a reasonable benefit/risk ratio. As described in greater detail herein, pharmaceutically acceptable carriers suitable for use in the present invention include gases, liquids, and semi-solid and solid materials.

Except when noted, "subject" or "patient" are used interchangeably and refer to mammals such as human patients and non-human primates, as well as experimental animals such as rabbits, dogs, cats, rats, mice, and other animals. Accordingly, "subject" or "patient" as used herein means any mammalian patient or subject to which the compositions of the invention can be administered. In some embodiments of the present invention, the patient will be suffering from an infectious or inflammatory disease, or an autoimmune disease. In some embodiments of the present invention, the patient will have been diagnosed with cancer. In an exemplary embodiment of the present invention, to identify candidate patients for treatment according to the invention, accepted screening methods are employed to determine the status of an existing disease or condition in a subject or risk factors associated with a targeted or suspected disease or condition. These screening methods include, for example, examinations to determine whether a subject is suffering from an infectious disease, an inflammatory disease, cancer, or an autoimmune disease. These and other routine methods allow the clinician to select subjects in need of therapy.

"Treating" refers to any indicia of success in the treatment or amelioration of, for example, an infectious disease, an inflammatory disease such as a GM-CSF-mediated inflammatory disease, cancer, or an autoimmune disease, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination. Accordingly, the term "treating" includes the administration of the compounds or agents of the present invention to delay, to alleviate, or to arrest or inhibit development of the symptoms or conditions associated with cancer, an infectious disease, an inflammatory disease such as a GM-CSF-mediated inflammatory disease, or an autoimmune disease. Treating includes, for example, inhibition of growth of dysplastic cells, inhibition of the progression of cancer or neoplastic disease, maintenance of inhibited tumor growth, and induction of remission.

"Therapeutic compound" as used herein refers to a compound useful in the prophylaxis or treatment of a disease or condition such as cancer, an infectious disease, an inflammatory disease, or an autoimmune disease.

"Therapeutic effect" refers to the reduction, elimination, or prevention of the disease, symptoms of the disease, or side effects of the disease in the subject. "Effective amount" refers to an amount necessary to produce a desired effect. A "therapeutically effective amount" means the amount that, when administered to a subject for treating a disease, condition or disorder, is sufficient to effect treatment for that disease.

"Concomitant administration," "concurrent administration," or "co-administration" as used herein includes administration of the active agents (e.g., MAbs, chemotherapeutic agents, biomolecules), in conjunction or combination, together, or before or after each other. The multiple agent(s) may be administered by the same or by different routes, simultaneously or sequentially, as long as they are given in a manner sufficient to allow all agents to achieve effective concentrations at the site of action. A person of ordinary skill in the art would have no difficulty determining the appropriate timing, sequence, and dosages of administration for particular drugs and compositions of the present invention.

"Donor cells" is used broadly to refer to cells fused to human B-cells to generate hybridomas. The cells include but are not limited to rodent myelomas as understood by those skilled in the art; rodent cell lines, human cell lines; avian cell lines. Cell lines may be derived by any means known by those skilled in the art.

"Immunoglobulin" or "antibody" is used broadly to refer to both antibody molecules and a variety of antibody-derived molecules and includes any member of a group of glycoproteins occurring in higher mammals that are major components of the immune system. The term "antibody" is used in the broadest sense and specifically covers monoclonal antibodies, antibody compositions with polyepitopic specificity, bispecific antibodies, diabodies, and single-chain molecules, as well as antibody fragments (e.g., Fab, F(ab')2, and Fv), so long as they exhibit the desired biological activity. An immunoglobulin molecule includes antigen binding domains, which each include the light chains and the end-terminal portion of the heavy chain, and the Fc region, which is necessary for a variety of functions, such as complement fixation. There are five classes of immunoglobulins wherein the primary structure of the heavy chain, in the Fc region, determines the immunoglobulin class. Specifically, the alpha, delta, epsilon, gamma, and mu chains correspond to IgA, IgD, IgE, IgG and IgM, respectively. As used herein "immunoglobulin" or "antibody" includes all subclasses of alpha, delta, epsilon, gamma, and mu and also refers to any natural (e.g., IgA and IgM) or synthetic multimers of the four-chain immunoglobulin structure. Antibodies non-covalently, specifically, and reversibly bind an antigen.

The term "monoclonal antibody" as used herein refers to an antibody obtained from a population of substantially homogeneous antibodies, i.e., the individual antibodies comprising the population are identical except for possible naturally occurring mutations that can be present in minor amounts. For example, monoclonal antibodies may be produced by a single clone of antibody-producing cells. Unlike polyclonal antibodies, monoclonal antibodies are monospecific (e.g., specific for a single epitope of a single antigen). The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention can be made by the hybridoma method first described by Kohler et al., *Nature*, 256: 495, 1975, or can be made by recombinant DNA methods. The "monoclonal antibodies" can also be isolated from phage antibody libraries using the techniques described in Marks et al., *J. Mol. Biol.*, 222: 581-597, 1991, for example.

As used herein "chimerized" refers to an immunoglobulin, wherein the heavy and light chain variable regions are not of human origin and wherein the constant regions of the heavy and light chains are of human origin.

"Humanized" refers to an immunoglobulin such as an antibody, wherein the amino acids directly involved in antigen binding, the complementarity determining regions (CDR), of the heavy and light chains are not of human origin, while the rest of the immunoglobulin molecule, the framework regions of the variable heavy and light chains and the constant regions of the heavy and light chains, are of human origin.

"Fully human" refers to an immunoglobulin, such as an antibody, where the whole molecule is of human origin or consists of an amino acid sequence identical to a human form of the antibody.

"Epitope" refers to an immunological determinant of an antigen that serves as an antibody-binding site. As used herein, the term "conformational epitope" refers to a discontinuous epitope formed by a spatial relationship between amino acids of an antigen other than an unbroken series of amino acids.

"Hybridoma" refers to the product of a cell-fusion between a cultured neoplastic lymphocyte and a primed B- or T-lymphocyte which expresses the specific immune potential of the parent cell.

"GM-CSF" refers to a family of glycoprotein growth factors that control the production, differentiation, and function of granulocytes and monocytes-macrophages. Exemplary, but by no means the only form of such molecules, can be seen in U.S. Pat. No. 5,602,007 (34), incorporated by reference.

As used herein the term "biomolecule" refers to any molecule that can be conjugated to, coadministered with, administered before or after administering an antibody, or otherwise used in association with an antibody of the invention. Biomolecules include, but are not limited to, enzymes, proteins, peptides, amino acids, nucleic acids, lipids, carbohydrates, and fragments, homologs, analogs, or derivatives, and combinations thereof. Examples of biomolecules include but are not limited to interleukin-2, interferon alpha, interferon beta, interferon gamma, rituxan, zevalin, herceptin, erbitux, and avastin. The biomolecules can be native, recombinant, or synthesized, and may be modified from their native form with, for example, glycosylations, acetylations, phosphorylations, myristylations, and the like. The term biomolecule as it is used herein is not limited to naturally occurring molecules, and includes synthetic molecules having no biological origin.

Polypeptides in accordance with the present invention can be synthesized from amino acids by techniques known to those skilled in the polypeptide art. In general, these methods comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group (e.g., lysine).

Various methods of preparing polypeptides of the present invention are known in the art (WO 89/06657; WO 92/22315; WO 98/49191; U.S. Pat. Nos. 5,260,273; 5,164, 369; 5,407,914; 5,789,381; 5,952,303; 6,013,619; 6,013, 764; 6,120,795; 6,613,734.).

Additional residues can be added at either terminus of a polypeptide of the present invention, such as for the purpose of providing a "linker" by which such a polypeptide can be conveniently affixed to a label or solid matrix, or carrier. Labels, solid matrices and carriers that can be used with the polypeptides of this invention are known in the art; some examples are also described herein.

Amino acid residue linkers are usually at least one residue and can be 40 or more residues, more often 1 to 10 residues. Typical amino acid residues used for linking are tyrosine, cysteine, lysine, glutamic and aspartic acid, or the like. In addition, a polypeptide sequence of this invention can differ from the natural sequence by the sequence being modified by terminal-$NH_2$ acylation, e.g., acetylation, or thioglycolic acid amidation, terminal-carboxylamidation, e.g., ammonia, methylamine, and the like.

While it is appreciated that many useful polypeptides disclosed herein, e.g., SEQ ID NOs: 1-5, it is also true that a wide variety of other molecules, including uncommon but naturally occurring amino acids, metabolites and catabolites of natural amino acids, substituted amino acids, and amino acid analogs, as well as amino acids in the "D" configuration, are useful in molecules and compositions of the present invention. In addition, "designed" amino acid derivatives, analogs and mimetics are also useful in various compounds, compositions and methods of the present invention, as well as polymers including backbone structures composed of non-amide linkages.

As used herein, "analogs" and "derivatives" of polypeptides and amino acid residues are intended to encompass metabolites and catabolites of amino acids, as well as molecules which include linkages, backbones, side-chains or side-groups which differ from those ordinarily found in what are termed "naturally-occurring" L-form amino acids. (The terms "analog" and "derivative" can also conveniently be used interchangeably herein.). Thus, D-amino acids, molecules which mimic amino acids and amino acids with "designed" side chains (i.e., that can substitute for one or more amino acids in a molecule having surfactant activity) are also encompassed by the terms "analogs" and "derivatives" herein.

For example, in addition to the L-amino acids listed in Table 1, amino acid metabolites such as homoarginine, citrulline, ornithine, and α-aminobutanoic acid are also useful in molecules and compositions of the present invention.

In another variation, one can wish to construct a molecule that adopts a more "rigid" conformation; one means of accomplishing this would be to add methyl or other groups to the α carbon atom of the amino acids.

Further, substituted amino acids which are not generally derived from proteins, but which are known in nature, are useful as disclosed herein, include the following examples: L-canavanine; 1-methyl-L-histidine; 3-methyl-L-histidine; 2-methyl L-histidine; α,ε-diaminopimelic acid (L form, meso form, or both); sarcosine; L-ornithine betaine; betaine of histidine (herzynine); L-citrulline; L-phosphoarginine; D-octopine; o-carbamyl-D-serine; γ-aminobutanoic acid; and β-lysine. D-amino acids and D-amino acid analogs, including the following, are also useful in proteins, peptides and compositions of the present invention: D-alanine, D-serine, D-valine, D-leucine, D-isoleucine, D-alloisoleucine, D-phenylalanine, D-glutamic acid, D-proline, and D-allo-hydroxyproline, and the like. The foregoing can also be used in GM-CSF polypeptides according to the present invention.

It should also be appreciated that the present invention encompasses a wide variety of modified amino acids, including analogs, metabolites, catabolites, and derivatives, irrespective of the time or location at which modification occurs. In essence, one can place modified amino acids into three categories: (1) catabolites and metabolites of amino acids; (2) modified amino acids generated via posttranslational modification (e.g., modification of side chains); and (3) modifications made to amino acids via non-metabolic or non-catabolic processes (e.g., the synthesis of modified amino acids or derivatives in the laboratory).

The present invention also contemplates that one can readily design side chains of the amino acids of residue units that include longer or shortened side chains by adding or subtracting methylene groups in either linear, branched chain, or hydrocarbon or heterocyclic ring arrangements. The linear and branched chain structures can also contain non-carbon atoms such as S, O, or N. Fatty acids can also be useful constituents of surfactant molecules herein. The designed side chains can terminate with (R') or without (R) charged or polar group appendages.

Analogs, including molecules resulting from the use of different linkers, are also useful in the peptides of the invention. Molecules with side chains linked together via linkages other than the amide linkage, e.g., molecules containing amino acid side chains or other side chains (R- or R'-) wherein the components are linked via carboxy- or phospho-esters, ethylene, methylene, ketone or ether linkages, to name a few examples, are also useful as disclosed herein. In essence, any amino acid side chain, R or R' group-containing molecule can be useful as disclosed herein.

The present invention also contemplates molecules comprising peptide dimers joined by an appropriate linker, e.g., peptide dimers linked by cysteine molecules. (As those of skill in the art are aware, two cysteine molecules can be linked together by a disulfide bridge formed by oxidation of their thiol groups.). Such linkers or bridges can thus cross-link different polypeptide chains, dimers, trimers, and the like. Other useful linkers which can be used to connect peptide dimers and/or other peptide multimers include those listed above, e.g., carboxy- or phospho-ester, ethylene, methylene, ketone or ether linkages, and the like.

One of skill in the art will appreciate that one can make a variety of modifications to individual amino acids, to the linkages, and/or to the chain itself, which modifications will produce molecules falling within the scope of the present invention, as long as the resulting molecule possesses biological (e.g., antigenic) activity as described herein.

Preferred antigenic polypeptides of the invention are antigenic peptides of GM-CSF (SEQ ID NO:1), and preferably of mature GM-CSF (SEQ ID NO:2). In some embodiments, the antigenic peptide comprises at least 5 consecutive amino acids of the amino acid sequence shown in SEQ ID NO: 1 or SEQ ID NO:2. In other embodiments, the antigenic peptide comprises at least 10 consecutive amino acids of the amino acid sequence shown in SEQ ID NO: 1 or SEQ ID NO:2. In other embodiments, the antigenic peptide comprises at least 15 consecutive amino acids of the amino acid sequence shown in SEQ ID NO:1 or SEQ ID NO:2. In other embodiments, the immunogenic portion comprises at least 20 consecutive amino acids of the amino acid sequence shown in SEQ ID NO:1 or SEQ ID NO:2. In still other embodiments, the immunogenic portion comprises at least 25 consecutive amino acids of the amino acid sequence shown in SEQ ID NO: 1 or SEQ ID NO:2. In certain preferred embodiments of the invention, the antigenic peptide of the GM-CSF protein is amino acids 14-28 (SEQ ID NO:3), amino acids 9-23 (SEQ ID NO:4), or amino acids 80-94 (SEQ ID NO:5) of the mature amino acid sequence of mature GM-CSF (SEQ ID NO:2).

In some embodiments of the invention, GM-CSF or antigenic peptides thereof are conjugated to an immunogenic protein to enhance the immunogenicity of the antigen. The immunogenic protein may be any protein that enhances the immune response of the cells, such as, but not limited to tetanus toxoid C (TT), keyhole limpet hemocyanin (KLH), albumin, ovalbumin, chick albumin (CAB), bovine serum albumin, thyroglobulin, diptheria toxoid, BCG, cholera toxin and the like. In some embodiments, the antigen is generated by denaturing the mature protein.

Previously reported methods for generation of hybridomas secreting human MAbs (WO2004/046330) using primary human B-cells were employed herein. Peripheral blood mononuclear cells, preferably human PBMCs, are immunized ex vivo in the presence of target antigen and then immortalized via cell fusion with donor cells. Alternatively, selected PBMCs are identified whose sera have high immune reactivity to antigen of interest.

Hybrid cells derived from the donor cells are screened for secretion of target antigen-specific MAbs. In some embodiments are provided methods for producing hybridoma cells producing monoclonal antibodies against a target antigen from ex vivo immunized immunoglobulin-producing cells comprising: (a) combining peripheral blood mononuclear cells comprising immunoglobulin-producing cells with a target antigen ex vivo; (b) fusing the immunoglobulin-producing cells with donor cells to form hybridoma cells; (c) determining binding of antigen by antibodies produced from the hybridoma cells; and (d) selecting hybridoma cells that produce antibodies that bind the target antigen; thereby generating hybridoma cells that produce antibodies against the target antigen. In a preferred embodiment, the PBMCs are from healthy donors. The target antigen is preferably GM-CSF and more preferably comprises an amino acid sequence of one of SEQ ID NOs:35-38.

Alternatively, methods for generating hybridomas that produce monoclonal antibodies against target disease-associated antigen comprise the steps of: (a) fusing ex vivo peripheral blood mononuclear cells comprising immunoglobulin-producing B-cells derived from a patient having a disease or an antigen-exposed donor with donor cells to form hybridoma cells; (b) determining binding by the antibodies produced from the hybridoma cells to target antigen; and (c) selecting hybridoma cells that produce antibodies that bind to the target antigen; thereby producing hybridoma cells that express antibodies against the target disease. Preferably, the target antigen is a disease-associated antigen, and preferably is associated with cancer, an infectious disease, or an autoimmune disease. More preferably, the disease associated antigen is GM-CSF. The target antigen is preferably GM-CSF and more preferably comprises an amino acid sequence of one of SEQ ID NOs:35-38. In a preferred embodiment, the antigen-exposed donor has been exposed to GM-CSF or may have pulmonary alveolar proteinosis (PAP).

The invention provides methods for producing hybridoma cells producing antibodies to target antigen (e.g., GM-CSF or antigenic peptides thereof) from ex vivo-immunized immunoglobulin-producing cells comprising: (a) combining peripheral blood mononuclear cells comprising immunoglobulin-producing cells with target antigen ex vivo; (b) fusing the immunoglobulin-producing cells with donor cells to form hybridoma cells; (c) performing a screen for binding of immunoglobulins produced by the hybridoma cells to target antigen; thereby producing hybridoma cells producing antibodies to target antigen. In a preferred embodiment, the PBMCs are from healthy donors. In some embodiments, the target antigen comprises an antigenic polypeptide of the invention. The target antigen preferably comprises an amino acid sequence of one of SEQ ID NOs:1-5, preferably any one of SEQ ID NOs:3-5.

Alternatively, the invention provides methods for producing hybridoma cells producing antibodies to a target antigen (e.g., GM-CSF, or antigenic peptides thereof) comprising: (a) selecting peripheral blood mononuclear cells comprising immunoglobulin-producing cells from an antigen-exposed donor; (b) fusing the immunoglobulin-producing cells with myeloma cells to form hybridoma cells; (c) performing a screen for binding of immunoglobulins produced by the hybridoma cells to a target antigen; thereby producing hybridoma cells producing antibodies to the target antigen. In some embodiments, the target antigen comprises an antigenic polypeptide of the invention. The target antigen preferably comprises an amino acid sequence of one of SEQ ID NOs: 1-5, more preferably SEQ ID NOs:3-5. In a preferred embodiment, the donor has been exposed to GM-CSF, or antigenic peptides thereof, or may have pulmonary alveolar proteinosis (PAP).

In some embodiments, the donor (e.g., myeloma) cells express a protein inhibitor of mismatch repair. In some aspects, the hybridoma cells express a protein inhibitor of mismatch repair. In some embodiments of the method of the invention, the protein inhibitor of mismatch repair is introduced into the hybridoma cell after the fusion of the myeloma with the immunoglobulin-producing cells. In other embodiments, the protein inhibitor of mismatch repair is introduced into the donor or myeloma cell prior to the fusion with the immunoglobulin-producing cells. In still other embodiments, the donor or myeloma cells or antibody producing cells are naturally deficient in mismatch repair.

Protein inhibitors of mismatch repair include dominant negative alleles of mismatch repair genes. Dominant negative alleles of mismatch repair genes include but are not limited to dominant negative alleles of PMS2, PMS1, PMSR3, PMSR2, PMSR6, MLH1, GTBP, MSH3, MSH2, MLH3, or MSH1, and homologs of mutL and mutS genes. In addition, polypeptides capable of interfering in mismatch repair may be used. For example, a dominant negative allele of mutL PMS2 comprises the first 133 amino acids PMS2. Further delineation of amino acids in mutL homologs reveals amino acids LSTAVKELVENSLDAGAT-NIDLKLKDYGVDLIEVSDNGCGVEEENFE (SEQ ID NO:6) and LRQVLSNLLDNAIKYTPEGGEIT-VSLERDGDHLEITVEDNGPGIPEEDLE (SEQ ID NO:7) or fragments thereof. Protein inhibitors of mismatch repair thus include polypeptides of SEQ ID NOs: 6 and 7 and fragments thereof. In preferred embodiments, the protein inhibitor of mismatch repair is inactivated. For example, the protein inhibitor of mismatch repair may be inactivated before or after identification of a hybridoma cell that generates monoclonal antibodies to the target antigen. Inactivation of the protein inhibitor of mismatch repair may be by any means known in the art, for example, removal of an inducer or removal of the protein inhibitor of mismatch repair from the cell (i.e., curing the cell of the protein inhibitor of mismatch repair). Inactivation of the inhibitor of mismatch repair stabilizes the genome of the hypermutated hybridoma.

In some embodiments of the methods of generating hybridoma cells of the invention, the hybridoma cells are exposed to a chemical inhibitor of mismatch repair. Chemical inhibitors of mismatch repair used in certain embodiments of the methods of the invention include, but are not limited to, at least one of an anthracene, an ATPase inhibitor, a nuclease inhibitor, an RNA interference molecule, a polymerase inhibitor and an antisense oligonucleotide that specifically hybridizes to a nucleotide encoding a mismatch repair protein (WO2004/046330). In preferred embodiments, the chemical inhibitor is an anthracene compound having the formula:

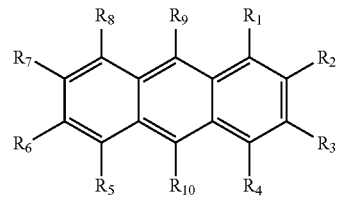

wherein $R_1$-$R_{10}$ are independently hydrogen, hydroxyl, amino, alkyl, substituted alkyl, alkenyl, substituted alkenyl, alkynyl, substituted alkynyl, O-alkyl, S-alkyl, N-alkyl, O-alkenyl, S-alkenyl, N-alkenyl, O-alkynyl, S-alkynyl, N-alkynyl, aryl, substituted aryl, aryloxy, substituted aryloxy, heteroaryl, substituted heteroaryl, aralkyloxy, arylalkyl, alkylaryl, alkylaryloxy, arylsulfonyl, alkylsulfonyl, alkoxycarbonyl, aryloxycarbonyl, guanidino, carboxy, an alcohol, an amino acid, sulfonate, alkyl sulfonate, CN, $NO_2$, an aldehyde group, an ester, an ether, a crown ether, a ketone, an organosulfur compound, an organometallic group, a carboxylic acid, an organosilicon or a carbohydrate that optionally contains one or more alkylated hydroxyl groups; wherein said heteroalkyl, heteroaryl, and substituted heteroaryl contain at least one heteroatom that is oxygen, sulfur, a metal atom, phosphorus, silicon or nitrogen; and wherein said substituents of said substituted alkyl, substituted alkenyl, substituted alkynyl, substituted aryl, and substituted heteroaryl are halogen, CN, $NO_2$, lower alkyl, aryl, heteroaryl, aralkyl, aralkoxy, guanidino, alkoxycarbonyl, alkoxy, hydroxy, carboxy and amino; and wherein said amino groups are optionally substituted with an acyl group, or 1 to 3 aryl or lower alkyl groups. In certain embodiments, $R_5$ and $R_6$ are hydrogen. In other embodiments, $R_1$-$R_{10}$ are independently hydrogen, hydroxyl, methyl, ethyl, propyl, isopropyl, butyl, isobutyl, phenyl, tolyl, hydroxymethyl, hydroxypropyl, or hydroxybutyl. Non-limiting examples of the anthracenes include 1,2-dimethylanthracene, 9,10-dimethylanthracene, 7,8-dimethylanthracene, 9,10-duphenylanthracene, 9,10-dihydroxymethylanthracene, 9-hydroxymethyl-10-methylanthracene, dimethylanthracene-1,2-diol, 9-hydroxymethyl-10-methylanthracene-1,2-diol, 9-hydroxymethyl-10-methylanthracene-3,4-diol, and 9,10-di-m-tolylanthracene.

The chemical inhibitor may be introduced into the growth medium of the cells. In some embodiments, the chemical inhibitor may be withdrawn from the hypermutated hybridoma cells in order to re-stabilize the genome of the cells. Alternatively, the method may comprise inactivation of the chemical inhibitor of mismatch repair, thereby stabilizing the genome of the hypermutated hybridoma.

In some embodiments, the methods further comprise cloning the immunoglobulin-producing genes from the antibody-producing cells and transfecting the immunoglobulin genes into a mammalian expression cell, wherein the immunoglobulin genes are operably linked to expression control sequences.

The invention also provides methods for producing mammalian expression cells that produce high affinity antibodies to target antigen from ex vivo immunized immunoglobulin-producing cells comprising: (a) combining peripheral blood mononuclear cells comprising immunoglobulin-producing cells with a target antigen ex vivo; (b) fusing the immunoglobulin-producing cells with donor cells to form hybridoma cells; (c) determining binding of antigen by antibodies produced from the hybridoma cells; (d) optimizing antibody production of the hybridoma by inhibiting mismatch repair; or cloning immunoglobulin genes from the hybridoma into a mammalian expression cell, wherein the mismatch repair of the mammalian expression cell is inhibited; and (e) selecting hybridoma cells that produce antibodies that bind the target antigen; thereby generating hybridoma cells that produce antibodies against the target antigen. As an alternative to steps (a) and (b), fusion ex vivo of peripheral blood mononuclear cells comprising immunoglobulin-producing B-cells derived from a patient having a disease or an antigen-exposed donor with donor cells to form hybridoma cells may be used.

The invention also provides methods for producing mammalian expression cells that produce high affinity antibodies to target antigen from ex vivo immunized immunoglobulin-producing cells comprising: (a) combining peripheral blood mononuclear cells comprising immunoglobulin-producing cells with target antigen ex vivo; (b) fusing the immunoglobulin-producing cells with myeloma cells to form hybridoma cells; (c) performing a screen for binding of antibodies produced from said hybridoma cells to target antigen; (d) optimizing production of the hybridoma by inhibiting mismatch repair; or cloning immunoglobulin genes from the hybridoma into a mammalian expression cell, wherein the mismatch repair of the mammalian expression cell is inhibited; and (e) performing a screen for mammalian expression cells that secrete antibodies with higher affinity for target antigen as compared to antibodies produced from the hybridoma or recombinant cells.

The invention also provides a method for producing mammalian expression cells that produce high titers of high-affinity antibodies from ex vivo immunized immunoglobulin-producing cells comprising: (a) combining peripheral blood mononuclear cells comprising immunoglobulin-producing cells with a target antigen ex vivo; (b) fusing the immunoglobulin-producing cells with donor cells to form hybridoma cells; (c) determining binding of antigen by antibodies produced from the hybridoma cells; (d) cloning immunoglobulin genes from the hybridoma into a parental mammalian expression cell, wherein mismatch repair of the mammalian expression cell is inhibited; (e) incubating the parental mammalian cell or hybridoma expression cell to allow for mutagenesis, thereby forming hypermutated mammalian expression cells; (f) selecting hypermutable mammalian expression cells that secrete antibodies with higher affinity for target antigen as compared to antibodies produced from the parental hybridoma cells or selecting hypermutable mammalian expression cells that secrete higher titers of antibodies than parental mammalian expression cells; thereby producing mammalian expression cells that produce antibodies to target antigen from ex vivo immunized immunoglobulin-producing cells. As an alternative to steps (a) and (b), fusion ex vivo of peripheral blood mononuclear cells comprising immunoglobulin-producing B-cells derived from a patient having a disease or an antigen-exposed donor with donor cells to form hybridoma cells may be used.

The invention also provides a method for producing mammalian expression cells that produce high titers of high-affinity antibodies from ex vivo immunized immunoglobulin-producing cells comprising: (a) combining peripheral blood mononuclear cells comprising immunoglobulin-producing cells with target antigen ex vivo; (b) fusing the immunoglobulin-producing cells with myeloma cells to form hybridoma cells; (c) performing a screen for binding of antibodies produced from the hybridoma cells to antigen; (d) cloning immunoglobulin genes from the hybridoma into a parental mammalian expression cell, wherein mismatch repair of the mammalian expression cell is inhibited or optimizing production of the hybridoma by inhibiting mismatch repair; (e) incubating the parental mammalian cell or hybridoma expression cell to allow for mutagenesis, thereby forming hypermutated mammalian expression cells; (f) performing a screen of hypermutable mammalian expression cells that secrete antibodies with higher affinity for target antigen as compared to antibodies produced from the hybridoma cells; and (g) performing a screen of hypermutable mammalian expression cells that secrete higher titers of antibodies than parental mammalian expression cells; thereby producing mammalian expression cells that produce high titers of high-affinity antibodies from ex vivo immunized immunoglobulin-producing cells.

In some embodiments of the method of the invention, antibodies are screened using an ELISA-based assay or other assays that can measure antibody-antigen binding known in the art. Crowther, J. R. (2001) The ELISA guidebook, 1st ed. Humana Press, Totowa, N.J.

In some embodiments, the screening assays screen for hypermutated hybridomas that produce higher affinity antibodies than those produced by the parental hybridomas.

In some embodiments, the method of the invention further comprises selecting hypermutated antibody-producing cells having higher titers of antibodies than that produced by the originally selected cells.

Methods of fusion of immunoglobulin-producing cells to myeloma cells and myeloma cells useful in such methods also are known in the art. Kohler & Milstein, *Eur. J. Immunol.* 1976. 6:511-9. Derivation of specific antibody-producing tissue culture and tumor lines by cell fusion.

Human B-cells used for the generation of MAbs designed for administration to humans may represent a potential vehicle of viral transmission. Fusion partner cells and peripheral blood mononuclear cells (PBMCs) from donors may be pre-screened to confirm absence of viral DNA, for example, by PCR, including immunodeficiency-1 and 2, hepatitis B and C, cytomegalo-, herpes-6, and Epstein Barr viruses.

Hybridoma cells produced according to the methods of the invention are included within the scope of the invention.

The invention also comprises antibodies to target antigens produced by the hybridoma cells generated according to the methods of the invention. Antibodies of the invention also comprise antibodies produced recombinantly using the polynucleotides of the invention. Preferred antibodies of the invention are monoclonal antibodies. Antibodies of the invention preferably are fully human, more preferably fully human monoclonal antibodies.

Preferred antibodies of the invention specifically bind an epitope, for example a conformational epitope, of a target antigen. The antibodies of the invention preferably are directed against disease-associated antigen, for example, but not limited to GM-CSF, preferably human GM-CSF (SEQ ID NO: 1), more preferably mature human GM-CSF (SEQ ID NO:2). In some embodiments, the epitope to which the antibody binds comprises at least 5 consecutive amino acids of the amino acid sequence shown in SEQ ID NO:1 or SEQ ID NO:2. In other embodiments, the epitope to which the antibody binds comprises at least 10 consecutive amino acids of the amino acid sequence shown in SEQ ID NO:1 or SEQ ID NO:2. In other embodiments, the epitope to which the antibody binds comprises at least 15 consecutive amino acids of the amino acid sequence shown in SEQ ID NO:1 or SEQ ID NO:2. In other embodiments, the epitope to which the antibody binds comprises at least 20 consecutive amino acids of the amino acid sequence shown in SEQ ID NO:1 or SEQ ID NO:2. In still other embodiments, the epitope to which the antibody binds comprises at least 25 consecutive amino acids of the amino acid sequence shown in SEQ ID NO: 1 or SEQ ID NO:2. In certain preferred embodiments of the invention, the epitope of GM-CSF to which the antibody binds comprises an amino acid sequence of at least one of SEQ ID NOs: 35, 36, 37, 38, and 39. Antibody-producing cells have been placed with the Amer. Type Cult. Coll. (10801 University Blvd., Manassas, Va. 20110-2209) on Jan. 18, 2007 (10G9), and on Feb. 2, 2007 (E10) and have been assigned Access. Nos. PTA-8173 and PTA-8193, respectively. Examples of anti-GM-CSF antibodies of the invention are antibodies produced by such cells.

Those of skill in the art will recognize that antibody specificity is primarily determined by the six CDR regions, especially H chain CDR3 (Kala M et al. (2002) J. Biochem. 132:535-41; Morea V et al. (1998) J. Mol. Biol. 275:269-94; and, Chothia C et al. (1987) J. Mol. Biol. 196:901-17). Antibody framework regions, however, can play a role in antigen-antibody interactions (Panka D J et al. (1988) Proc. Natl. Acad. Sci. USA 85:3080-4), particularly with respect to their role in conformation of CDR loops (Foote J et al. (1992) J. Mol. Biol. 224:487-99). Thus, the inventive antibodies can comprise any combination of H or L chain CDR or FWR regions that confer antibody specificity for GM-CSF. Domain shuffling experiments, which are routinely carried out in the art (Jirholt P et al. (1998) Gene 215:471-6; Söderlind E et al. (2000) Nature Biotechnology 18:852-6), can be employed to generate antibodies that specifically bind GM-CSF according to the specifications described and exemplified herein. Antibodies generated by such domain shuffling experiments are within the scope of the present invention.

Accordingly, in some embodiments, the antibodies comprise a heavy chain CDR1 amino acid sequence substantially the same as or identical to SEQ ID NO:40 or 46. In some embodiments, the antibodies comprise a heavy chain CDR2 amino acid sequence substantially the same as or identical to SEQ ID NO:41 or 47. In some particularly preferred embodiments, the antibodies comprise a heavy chain CDR3 amino acid sequence substantially the same as or identical to SEQ ID NO:42 or 48. In some embodiments, the antibodies comprise a light chain CDR1 amino acid sequence substantially the same as or identical to SEQ ID NO:43 or 49. In some embodiments, the antibodies comprise a light chain CDR2 amino acid sequence substantially the same as or identical to SEQ ID NO:44 or 50. In some embodiments, the antibodies comprise a light chain CDR3 amino acid sequence substantially the same as or identical to SEQ ID NO:45 or 51. In some embodiments, the antibodies comprise a heavy chain FWR1 amino acid sequence substantially the same as or identical to SEQ ID NO:52 or 58. In some embodiments, the antibodies comprise a heavy chain FWR2 amino acid sequence substantially the same as or identical to SEQ ID NO:53 or 59. In some embodiments, the antibodies comprise a heavy chain FWR3 amino acid sequence substantially the same as or identical to SEQ ID NO:54 or 60. In some embodiments, the antibodies comprise a light chain FWR1 amino acid sequence substantially the same as or identical to SEQ ID NO:55 or 61. In some embodiments, the antibodies comprise a light chain FWR2 amino acid sequence substantially the same as or identical to SEQ ID NO:56 or 62. In some embodiments, the antibodies comprise a light chain FWR3 amino acid sequence substantially the same as or identical to SEQ ID NO:57 or 63.

In some preferred embodiments, the antibody of the invention comprises a heavy chain comprising an amino acid sequence of SEQ ID NO:8, 9, or 16. The heavy chain can be encoded by a nucleic acid sequence comprising a nucleotide sequence of SEQ ID NO: 10, 11, or 17. In some preferred embodiments, the antibody of the invention comprises a light chain comprising an amino acid sequence of SEQ ID NO:12, 13, or 18. The light chain can be encoded by a nucleic acid sequence comprising a nucleotide sequence of SEQ ID NO: 14, 15, or 19.

It is to be understood that because of the natural sequence variation likely to exist among heavy and light chains and the genes encoding them, one skilled in the art would expect to find some level of variation within the amino acid sequences or the genes encoding them, while still maintaining the unique binding properties (e.g., specificity and affinity) of the antibodies of the present invention. Such an expectation is due in part to the degeneracy of the genetic code, as well as to the known evolutionary success of conservative amino acid sequence variations, which do not appreciably alter the nature of the encoded protein. Accordingly, such variants and homologs are considered substantially the same as one another and are included within the scope of the present invention.

The antibodies of the invention thus include variants having single or multiple amino acid substitutions, deletions, additions, or replacements that retain the biological properties (e.g., binding affinity or immune effector activity) of the antibodies of the invention. The skilled person can produce variants having single or multiple amino acid substitutions, deletions, additions or replacements. These variants may include, inter alia: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies of the invention may include variants in which amino acid residues from one species are substituted for the corresponding residue in another species, either at the conserved or nonconserved positions. In other embodiments, amino acid residues at nonconserved positions are substituted with conservative or nonconservative residues. The techniques for obtaining these variants, including genetic (suppressions, deletions, mutations, etc.), chemical, and enzymatic techniques, are known to the person having ordinary skill in the art.

In some preferred embodiments, the antibodies can comprise a heavy chain that comprises the amino acid sequence of SEQ ID NO:8 and a light chain that comprises the amino acid sequence of SEQ ID NO: 12. In some preferred embodiments, the antibodies can comprise a heavy chain that comprises the amino acid sequence of SEQ ID NO: 16 and a light chain that comprises the amino acid sequence of SEQ ID NO: 18. In some embodiments, the antibodies can comprise a heavy chain that comprises the amino acid sequence of SEQ ID NO:9 and a light chain that comprises the amino acid sequence of SEQ ID NO: 13. Those of skill in the art will recognize, however, that in some cases, the pairing of a given heavy with various light chains, or the pairing of a given light chain with various heavy chains will produce antibodies with the same or better specificity and/or affinity than the native combination. Accordingly, the invention is not limited to the preferred combinations of H and L chain pairs, and the inventive antibodies thus encompass different combinations of H and L chain pairs, including without limitation, the H and L chains described herein, or other H or L chains that would be known to those of skill in the art, or otherwise experimentally determined to be compatible with the H and L chains described herein in order to obtain specific and high affinity binding to GM-CSF.

Preferred antibodies of the invention comprise two heavy chains. Preferred antibodies of the invention comprise two light chains. More preferred are antibodies comprising two heavy chains and two light chains of the invention.

The antibodies of the invention include variants having single or multiple amino acid substitutions, deletions, additions, or replacements that retain the biological properties (e.g., binding affinity or immune effector activity) of the antibodies of the invention. The skilled person can produce variants having single or multiple amino acid substitutions, deletions, additions or replacements. These variants may include, inter alia: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies of the invention may include variants in which amino acid residues from one species are substituted for the corresponding residue in another species, either at the conserved or nonconserved positions. In another embodiment, amino acid residues at nonconserved positions are substituted with conservative or nonconservative residues. The techniques for obtaining these variants, including genetic (suppressions, deletions, mutations, etc.), chemical, and enzymatic techniques, are known to the person having ordinary skill in the art. Antibodies of the invention also include antibody fragments. A "fragment" refers to polypeptide sequences which are preferably at least about 40, more preferably at least to about 50, more preferably at least about 60, more preferably at least about 70, more preferably at least about 80, more preferably at least about 90, and more preferably at least about 100 amino acids in length, and which retain some biological activity or immunological activity of the full-length sequence, for example, binding affinity or avidity and immune effector activity.

The antibodies of the invention have binding affinities for target antigen that include a dissociation constant ($K_D$) of less than $1\times10^{-2}$. In some embodiments, the $K_D$ is less than $1\times10^{-3}$. In other embodiments, the $K_D$ is less than $1\times10^{-4}$. In some embodiments, the $K_D$ is less than $1\times10^{-5}$. In still other embodiments, the $K_D$ is less than $1\times10^{-6}$. In other embodiments, the $K_D$ is less than $1\times10^{-7}$. In other embodiments, the $K_D$ is less than $1\times10^{-8}$. In other embodiments, the $K_D$ is less than $1\times10^{-9}$. In other embodiments, the $K_D$ is less than $1\times10^{-10}$. In still other embodiments, the $K_D$ is less than $1\times10^{-11}$. In some embodiments, the $K_D$ is less than $1\times10^{-12}$. In other embodiments, the $K_D$ is less than $1\times10^{-13}$. In other embodiments, the $K_D$ is less than $1\times10^{-14}$. In still other embodiments, the $K_D$ is less than $1\times10^{-15}$.

Antibodies of the invention include derivatives that are modified, e.g., by the covalent attachment of any type of molecule to the antibody such that covalent attachment does not prevent the antibody from binding to its epitope. Examples of suitable derivatives include, but are not limited to glycosylated antibodies and fragments, acetylated antibodies and fragments, pegylated antibodies and fragments, phosphorylated antibodies and fragments, and amidated antibodies and fragments. The antibodies of the invention may themselves be derivatized by known protecting/blocking groups, proteolytic cleavage, linkage to a cellular ligand or other proteins, and the like. Further, the antibodies of the invention may contain one or more non-classical amino acids as described above. In some embodiments of the invention, GM-CSF or epitopes thereof are conjugated to an immunogenic protein to enhance the immunogenicity of the antigen. The immunogenic protein may be any protein that enhances the immune response of the cells, such as, but not limited to tetanus toxoid C (TT), keyhole limpet hemocyanin (KLH), albumin, ovalbumin, chick albumin (CAB), bovine serum albumin, thyroglobulin, diptheria toxoid, BCG, cholera toxin and the like. In some embodiments, the antigen is generated by denaturing the mature protein.

The antibodies of the invention may have post-translational moieties that improve upon antibody activity or stability. These moieties include sulfur, methyl, carbohydrate, phosphorus as well as other chemical groups commonly found on immunoglobulin molecules.

Antibodies of the invention may be of any isotype. Whereby isotype of antibody can be changes using in vivo class switching or by genetic engineering.

Nucleotide sequences that encode polypeptides of the invention are provided. Nucleic acids of the invention include but are not limited to genomic DNA, DNA, cDNA, RNA, double- and single-stranded nucleic acids, and complementary sequences thereof.

Preferred polynucleotides of the invention include nucleic acid sequences encoding an amino acid sequence of SEQ ID NO: 8 and/or SEQ ID NO: 12. In some embodiments, the heavy chain of the antibody is encoded by a polynucleotide comprising SEQ ID NO: 10. In some embodiments, the light chain of the antibody is encoded by a polynucleotide comprising SEQ ID NO: 14. Polynucleotides comprising a nucleic acid sequence encoding an amino acid sequence of SEQ ID NO:8 and an amino acid sequence of SEQ ID NO:12 also are provided. Preferably such a polynucleotide comprises a nucleic acid sequence of SEQ ID NO: 10 and/or SEQ ID NO: 14.

Preferred polynucleotides of the invention include nucleic acid sequences encoding an amino acid sequence of SEQ ID NO: 16 and/or SEQ ID NO:18. In some embodiments, the heavy chain of the antibody is encoded by a polynucleotide comprising SEQ ID NO: 17. In some embodiments, the light chain of the antibody is encoded by a polynucleotide comprising SEQ ID NO: 19. Polynucleotides comprising a nucleic acid sequence encoding an amino acid sequence of SEQ ID NO:16 and an amino acid sequence of SEQ ID NO:18 also are provided. Preferably such a polynucleotide comprises a nucleic acid sequence of SEQ ID NO: 17 and/or SEQ ID NO:19.

In some embodiments, polynucleotides of the invention (and the peptides they encode) include a leader sequence. Any leader sequence known in the art may be employed. The leader sequence may include but is not limited to a restriction site and/or a translation start site. For example, the invention provides nucleic acid sequences encoding an amino acid sequence of SEQ ID NO:9 and/or SEQ ID NO: 13. In some embodiments, the heavy chain of the antibody is encoded by a polynucleotide comprising SEQ ID NO: 11. In some embodiments, the light chain of the antibody is encoded by a polynucleotide comprising SEQ ID NO: 15. Polynucleotides comprising a nucleic acid sequence encoding an amino acid sequence of SEQ ID NO:9 and an amino acid sequence of SEQ ID NO: 13 also are provided. Preferably such a polynucleotide comprises a nucleic acid sequence of SEQ ID NO: 11 and/or SEQ ID NO: 15.

Also contemplated by the invention are expression vectors comprising the polynucleotides of the invention and host cells, such as but not limited to recombinant host cells, expressing the polynucleotides of the invention.

Recombinant expression vectors containing a sequence encoding a polypeptide of interest are provided. The expression vector may contain one or more additional sequences such as but not limited to regulatory sequences (e.g., promoter, enhancer), a selection marker, and a polyadenylation signal.

Recombinant expression vectors of the invention include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated.

The transcriptional and translational control sequences in expression vectors to be used in transforming vertebrate cells may be provided by viral sources. Exemplary vectors can be constructed as described in Okayama and Berg (1983) *Mol. Cell. Biol.* 3:280.

Selection markers that can be used in the system include those known in the art, such as positive and negative selection markers, such as but not limited to antibiotic resistance genes (e.g., neomycin resistance gene, a hygromycin resistance gene, a kanamycin resistance gene, a tetracycline resistance gene, a penicillin resistance gene), HSV-TK, HSV-TK derivatives for ganciclovir selection, or bacterial purine nucleoside phosphorylase gene for 6-methylpurine selection (Gadi et al. (2000) *Gene Ther.* 7:1738-1743). [0034] A nucleic acid sequence encoding a selection marker or the cloning site therefor may be upstream or downstream of a nucleic acid sequence encoding a polypeptide of interest or cloning site therefor.

In some embodiments, the vector includes one or more promoters, such as but not limited to a constitutive, inducible, host-specific, and/or tissue-specific promoter. For example, commonly used promoters and enhancers are derived from human cytomegalovirus (CMV), Adenovirus 2, Simian Virus 40 (SV40), and Polyoma. Viral genomic promoters, control and/or signal sequences may be utilized to drive expression which are dependent upon compatible host cells. Promoters derived from house-keeping genes can also be used (e.g., the β-globin, thymidine kinase, and the EF-1α promoters), depending on the identity of the cell type in which the vector is to be expressed. In some embodiments, a promoter is upstream of a nucleic acid sequence encoding one or more polypeptides of interest.

Vectors of the invention may contain one or more Internal Ribosome Entry Site(s) (IRES). Inclusion of an IRES sequence into fusion vectors may be beneficial for enhancing expression of some proteins.

In some embodiments the vector system will include one or more polyadenylation sites (e.g., SV40), which may be upstream or downstream of any of the aforementioned nucleic acid sequences.

Vector components may be contiguously linked, or arranged in a manner that provides optimal spacing for expressing the gene products (i.e., by the introduction of "spacer" nucleotides between the ORFs), or positioned in another way. Regulatory elements, such as the IRES motif, can also be arranged to provide optimal spacing for expression.

Cells transfected with expression vectors of the invention can be selected under positive selection conditions and/or screened for recombinant protein expression. Recombinant-positive cells are expanded and screened for subclones exhibiting a desired phenotype.

Cells, including eukaryotic and prokaryotic cells, can be transformed with the expression vectors of the invention. Accordingly, another embodiment of the invention provides a host cell transformed with an expression vector of the instant invention. Cells of the invention are preferably eukaryotic cells, more preferably cells of plant, rodent, or human origin, for example but not limited to NSO, CHO, perC.6, Tk-ts13, BHK, HEK293 cells, COS-7, T98G, CV-1/EBNA, L cells, C127, 3T3, HeLa, NS1, Sp2/0 myeloma cells, and BHK cell lines, among others.

In general, transfection will be carried out using a suspension of cells, or a single cell, although other methods can also be applied to the extent that sufficient fraction of the treated cells or tissue incorporates the polynucleotide, thereby allowing transfected cells to be grown and utilized. Techniques for transfection are well known. Several transformation protocols are known in the art. See, e.g., Kaufman (1988) *Meth. Enzymology* 185:537. As is readily understood by those skilled in the art, the appropriate transformation protocol is determined by the host cell type and the nature of the gene of interest. The basic components of any such protocol include introducing nucleic acid sequence encoding the protein of interest into a suitable host cell, and then identifying and isolating host cells which have incorporated the vector DNA in a stable, expressible manner. Techniques for introducing polynucleotides include but are not limited to electroporation, transduction, cell fusion, the use of calcium chloride, and packaging of the polynucleotide together with lipid for fusion with the cells of interest. If the transfection is stable, such that the selectable marker gene is expressed at a consistent level for multiple cell generations, then a cell line results.

One common method for transfection into mammalian cells in particular is calcium phosphate precipitation. Another method is polyethylene glycol (PEG)-induced fusion of bacterial protoplasts with mammalian cells. Schaffner et al. (1980) *Proc. Natl. Acad. Sci. USA* 77:2163. Yet another method is electroporation, which can also be used to introduce DNA directly into the cytoplasm of a host cell, as described, for example, in Potter et al. (1988) *Proc. Natl. Acad. Sci. USA* 81:7161.

Transfection of DNA can also be carried out using polyliposome reagents such as Lipofectin and Lipofectamine (available from Gibco BRL, Gaithersburg, Md.) which form lipid-nucleic acid complexes (or liposomes), which, when applied to cultured cells, facilitate uptake of the nucleic acid into the cells.

Once a cell expressing the desired protein is identified, it can be expanded and selected. Transfected cells may be selected in a number of ways. For example, cells may be selected for expression of the polypeptide of interest. For cells in which the vector also contains an antibiotic resistance gene, the cells may be selected for antibiotic resistance, which positively selects for cells containing the vector. In other embodiments, the cells may be allowed to grow under selective conditions.

Once a clone producing a protein is identified, the line can be further screened to identify subclones having one or more desired phenotypes, such as but not limited to cells that exhibit high-titer expression, enhanced growth properties, and/or the ability to yield proteins with desired biochemical characteristics, for example, due to protein modification and/or altered post-translational modifications. These phenotypes may be due to inherent properties of a given subclone or to mutagenesis. Mutagenesis can be effected through the use of chemicals, UV-wavelength light, radiation, viruses, insertional mutagens, defective DNA repair, or a combination of such methods.

Another aspect of the invention features pharmaceuticals composition of antibodies of the invention. The pharmaceutical compositions may be used to treat a disease, for example, cancer, an infectious disease, or an inflammatory disease in a patient.

The invention provides pharmaceutical compositions comprising one or more MAbs for the treatment of disease, such as but not limited to cancer, an infectious disease, or an inflammatory disease, formulated together with a pharmaceutically acceptable carrier.

In prophylactic applications, pharmaceutical compositions are administered to a patient susceptible to, or otherwise at risk of a disease or condition (e.g., cancer, an infectious disease, or an inflammatory disease) in a prophylactically effective amount. At-risk individuals include, but are not limited to, individuals with a family history of cancer, an infectious disease, or an inflammatory disease, individuals who have previously been treated for cancer, an infectious disease, or an inflammatory disease, and individuals presenting any other clinical indicia suggesting that they have an increased likelihood of developing cancer, an infectious disease, or an inflammatory disease. Alternatively stated, an at-risk individual is any individual who is believed to be at a higher risk than the general population for developing cancer, an infectious disease, or an inflammatory disease. The term "prophylactically effective amount" is meant to refer to an amount of a formulation which produces an effect observed as the prevention of the onset or recurrence of cancer, an infectious disease, or an inflammatory disease. Prophylactically effective amounts of a formulation are typically determined by the effect they have compared to the effect observed when a second formulation lacking the active agent is administered to a similarly situated individual.

In therapeutic applications, compositions are administered to a patient suspected of, or already suffering from such a disease in a therapeutically effective amount sufficient to cure, or at least partially arrest, the symptoms of the disease (biochemical and/or histological), including its complications and intermediate pathological phenotypes in development of the disease.

In both prophylactic and therapeutic regimes, agents are usually administered in several dosages until a sufficient response has been achieved. Typically, the response is monitored and repeated dosages are given if the response starts to wane.

Effective doses of a monoclonal antibody for the treatment of disease, e.g., cancer, an infectious disease, or an inflammatory disease, as described herein, vary depending upon many different factors, including means of administration, target site, physiological state of the patient, whether the patient is human or an animal, other medications administered, and whether treatment is prophylactic or therapeutic. Usually, the patient is a human but nonhuman mammals can also be treated.

Dosing is dependent on severity and responsiveness of the disease state to be treated, with the course of treatment lasting from days to several days to several months, or until a cure is effected or a diminution of the disease state is achieved. Optimal dosing schedules can be calculated from measurements of drug accumulation in the body of a patient or subject. Persons of ordinary skill can easily determine optimum dosages, dosing methodologies and repetition rates. Optimum dosages can vary depending on the relative potency of individual antibodies and, in the case of concomitant administration, the relative potency of known drugs used in the treatment of disease. Optimum dosages can generally be estimated based on EC50s found to be effective in in vitro and in vivo animal models.

In general, dosage is from 0.01 µg to 100 g per kg of body weight and can be given once or more daily, weekly, monthly or yearly, or even once every 2 to 20 years. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Although individual needs can vary, determination of optimal ranges for effective amounts of formulations is within the skill of the art. Human doses can be extrapolated from animal studies (REMINGTON'S PHARMACEUTICAL SCIENCES, 20TH ED., Gennaro, ed., Mack Publishing Co., Easton, Pa., 2000). Generally the dosage required to provide an effective amount of a formulation, which can be adjusted by one skilled in the art, will vary depending on the age, health, physical condition, weight, type and extent of the disease or disorder of the recipient, frequency of treatment, the nature of concurrent therapy (if any) and the nature and scope of the desired effect(s).

Pharmaceutical compositions of the invention may be formulated with a pharmaceutically acceptable carrier. Suitable pharmaceutically acceptable carriers include water, PBS, salt solution (such as Ringer's solution), alcohols, oils, gelatins, and carbohydrates, such as lactose, amylose, or starch, fatty acid esters, hydroxymethylcellulose, and polyvinyl pyrolidine. Such preparations can be sterilized, and if desired, mixed with auxiliary agents such as lubricants, preservatives, stabilizers, wetting agents, emulsifiers, salts for influencing osmotic pressure, buffers, and coloring. Pharmaceutical carriers suitable for use in the present invention are known in the art (REMINGTON'S PHARMACEUTICAL SCIENCES, 20TH ED., Gennaro, ed., Mack Publishing Co., Easton, Pa., 2000).

The pharmaceutical formulations, which can conveniently be presented in unit dosage form, can be prepared according to conventional techniques well known in the pharmaceutical industry. Such techniques include the step of bringing into association the active ingredients with the pharmaceutical carrier(s). In general the formulations are prepared by uniformly and intimately bringing into association the active ingredients with liquid carriers or finely divided solid carriers or both. The formulations can be presented in unit-dose or multi-dose containers, for example sealed ampoules and vials, and can be stored in a frozen or freeze-dried (lyophilized) condition requiring only the addition of sterile liquid carrier immediately prior to use.

The pharmaceutical compositions are generally formulated as sterile, substantially isotonic and in full compliance with all Good Manufacturing Practice (GMP) regulations of the U.S. Food and Drug Administration.

Additional guidance regarding formulation, dose and administration regimen is available in the art (Berkow et al., 1997, THE MERCK MANUAL OF MEDICAL INFORMATION, Home, ed., Merck Research Laboratories, Whitehouse Station, N.J.; Goodman et al., 1996, GOODMAN & GILMAN'S THE PHARMACOLOGICAL BASIS OF THERAPEUTICS, 9th ed. McGraw-Hill Health Professions Division, New York; Ebadi, 1998, CRC DESK REFERENCE OF CLINICAL PHARMACOLOGY, CRC Press, Boca Raton, Fla.; Katzung, 2001, BASIC & CLINICAL PHARMACOLOGY, 8TH ED. Lange Medical Books/McGraw-Hill Medical Pub. Division, New York; Speight et al., 1997, AVERV'S DRUG TREATMENT: A GUIDE TO THE PROPERTIES, CHOICE, THERAPEUTIC USE AND ECONOMIC VALUE OF DRUGS IN DISEASE MANAGEMENT, 4TH ED. Adis International, Auckland/Philadelphia, Pa.).

When used as a pharmaceutical treatment, the compositions of the present invention can be administered either alone or co-administered with other compounds or compositions that are used in the treatment of disease, for cancer, an infectious disease, or an inflammatory disease. Examples of such compounds, referred to herein as "supplemental compounds," or "supplemental compositions," include, but are not limited to, antibiotics, anti-cytokines, anti-asthma drugs, antiphospholipases (e.g., inhibitors of phospholipase), vasodilators (e.g., adenosine, beta-adrenergic agonists or antagonists, β-adrenergic blockers, α-adrenergic blockers, diuretics, smooth muscle vasodilators, nitrates, and angiotensin-converting enzyme inhibitors), biomolecules, cytostatic agents, and chemotherapeutic agents. Pharmaceutical compositions of the invention may comprise, for example, one or more supplemental compounds. In some embodiments, the antibody is conjugated to the supplemental compound.

According to yet another aspect of the invention, kits are provided, for example, for the treatment of cancer, an infectious disease, or an inflammatory disease.

The kits of the invention comprise antibody or an antibody composition of the invention and instructions for using the kit in a method for treating cancer, an infectious disease, or an inflammatory disease in a patient or for inhibiting the biological activity of target antigen (e.g., GM-CSF). The kit may comprise at least one supplemental compound. The kit may comprise instructions and/or means for administering the antibody or antibody composition, for example, by injection.

Antibodies of the invention may be used to detect antigen in a biological sample such as but not limited to blood serum. Any method known in the art may be used, such as but not limited to flow cytometry. For example, a biological sample may be incubated with antibody of the invention followed by washing and incubation with a labelled secondary antibody. For example, the secondary antibody may be directed to the light chain and conjugated to either FITC or phycoerythrin for purpose of detection.

Antigen neutralizing activity of antibodies of the invention may be tested in an antigen neutralization assay by any method known in the art. For example, neutralization activity of the antibodies may be assessed using antigen-dependent cell lines. Examples of GM-CSF-dependent cell lines include but are not limited to TF-1 and AML-193.

In a first antigen neutralization assay, antigen-dependent cells are suspended in assay medium, assay medium, antigen, or antigen pre-incubated for one hour with test or isotype control antibodies. Following the incubation period, growth inhibition is evaluated by any method known in the art. For example, Cell Titer reagent (Promega, WI) may be added followed by further incubation and measurement of optical density (O.D.) at 490 nm in a spectrophotometer and subtraction of medium background from samples. Percentage of antigen neutralization is calculated as follows: 100–[O.D. with Ig/O.D. without Ig)×100].

In another neutralization assay, antigen is mixed with anti-antigen antibodies of the invention. Antigen-dependent cells are added to the mixture, followed by incubation. After this incubation period, growth inhibition is measured. For example, the DNA proliferation marker MTS may be added followed by measurement of dye incorporation. Decreased dye incorporation in the presence of antibody relative to that in the absence of the anti-antigen antibody indicates neutralization of antigen.

Alternatively, antigen-dependent cells are grown in the presence of antigen followed by addition of increasing amounts of antibody to the culture media and assessment of neutralizing activity as described above.

Therapeutic methods of the invention include methods of inhibiting the biological activity of a target antigen, for example, GM-CSF and methods of treating a disease such as but not limited to cancer, an infectious disease, or an inflammatory disease by administering the pharmaceutical compositions of the antibodies of the invention to a patient or subject in need thereof. Biological activity of GM-CSF includes but is not limited to binding to the GM-CSF receptor. The methods may be employed, for example, to effect prophylactic or therapeutic treatment of a disease such as, but not limited to, cancer, an infectious disease, or an inflammatory disease.

The therapeutic methods of the invention are suitable for use in humans and non-human animals. Non-human animals which benefit from the invention include pets, exotic (e.g., zoo animals) and domestic livestock. Preferably the non-human animals are mammals.

The antibodies for use in the invention may be administered orally in any acceptable dosage form such as capsules, tablets, aqueous suspensions, solutions or the like. The antibodies may also be administered parenterally. That is via the following routes of administration: subcutaneous, intravenous, intramuscular, intra-articular, intra-synovial, intrasternal, intranasal, topically, intrathecal, intrahepatic, intralesional, and intracranial injection or infusion techniques. Generally, the antibodies will be provided as an intramuscular or intravenous injection.

The antibodies of the invention may be administered alone or with a pharmaceutically acceptable carrier, including acceptable adjuvants, vehicles and excipients.

The antibodies of the invention may be administered before, after, or simultaneously with another therapeutic agent. For example, the antibodies of the invention may be administered alone or co-administered with a supplemental compound.

The antibodies of the invention may be administered as a homogenous mixture of unconjugated or conjugated antibody or as a heterogeneous mixture of unconjugated and conjugated antibody.

Effective treatment may be assessed in a variety of ways. In one embodiment, effective treatment of cancer, an infectious disease, or an inflammatory disease is determined by a slowed progression of the disease. In still other embodiments, effective therapy is measured by increased well-being of the patient including such signs as weight gain, regained strength, decreased pain, thriving, and subjective indications from the patient of better health.

The following examples are provided to describe the invention in greater detail. They are intended to illustrate, not to limit, the invention.

Example 1

Generation of Antigen-Specific Human MAbs to GM-CSF

Materials and Methods

Human B-Cells, Ex-Vivo Immunization and Cell Culturing.

In all procedures followed, cells were grown in 5% $CO_2$ at 37° C. Leukopacks were obtained from tetanus toxoid (TT)-vaccinated healthy individuals. PBMCs were purified by Ficoll-Plaque (Amersham BioSciences) and CD19 positive B-cells and CD4 positive T-cells were isolated from PBMCs by EasySep® human CD4 and CD19 selection kit (StemCell Technologies), respectively, and mixed to make a B-cell/T-cell pool (BT4 cells). BT4 cells were cultured in complete RPMI1640 (Invitrogen, CA), which contained 10% heat-inactivated human serum AB (Nabi, FL), 2 mM L-glutamine, 0.1 mM non-essential amino acids, 1 mM sodium pyruvate, 55 µM 2-mercaptoethanol (Invitrogen, CA).

For ex-vivo immunizations, BT4 cells were co-cultured in the presence of T- and B-cell epitopes. Briefly, BT4 cells were seeded at a density of $10^6$/mL in complete RPMI containing 1 Lf/mL of tetanus toxoid (TT) (Cylex, MD) in the presence of irradiated autologous PBMCs at a 1:1 ratio to produce activated T cells (T-pool). To generate antigen-activated B-cells (B-pool), BT4 cells were seeded at a density of $3\times10^6$ cells/mL in complete RPMI containing 10% human serum AB, 5% condition medium from activated T-cells, 20 U/mL IL-2, 0.5 ng/mL IL-6, 100 U/mL IL-10 (PrepoTech, NJ), and 250 ng/mL of a cocktail of peptides (bio-World, OH) representing various regions of the targeted antigen, synthesized to contain both T- and B-cell epitopes as previously described (Zafiropoulos et al. (1997) J. Immunol. Methods 200:181-90).

The selected B-cell epitopes for GM-CSF were: EHVNAIQEARRLLNL (SEQ ID NO:3), STQPWE-HVNAIQEAR (SEQ ID NO:4), MASHYKQHCPPTPET (SEQ ID NO:5).

T- and B-pools were separately cultured for 7 days and then co-cultured ($10^6$ cell/mL) at a 1:10 ratio, respectively, on a monolayer of irradiated CHO feeder cells, in complete RPMI containing 10% heat-inactivated human AB serum and 400 U/ml IL-4 (PeproTech, NJ). After five days, co-cultured T- and B-pools were fused to generate hybridomas as described.

For the immortalization of pulmonary alveolar proteinosis (PAP) patients' B-cells, 100 mL of whole blood was processed to purify PBMCs. Lymphocytes were cultured for 7-10 days in complete RPMI containing 10% heat inactivated fetal bovine serum (FBS), (JRH Biosciences, KS), 2 ng/mL IL-4 (PeproTech, NJ), 2 mM L-glutamine, 0.1 mM non-essential amino acids, 1 mM sodium pyruvate, 55 µM 2-mercaptoethanol (Invitrogen, CA), 50 g/mL transferrin, 5 ng/mL phorbol myristate acetate (PMA), and 0.5 g/mL cyclosporine A (Sigma, MO), in the presence of irradiated CHO feeder cells. Lymphocytes were then electro-fused as described below.

Cell Fusion and Enzyme-Linked Immunosorbent Assay (ELISA) Screening of Antigen-Reacting Hybridomas.

Human B-cells used for the generation of MAbs designed for administration to humans may represent a potential vehicle of viral transmission. Fusion partner cells and PBMCs from healthy donors were pre-screened to confirm absence of viral DNA by PCR, including immunodeficiency-1 and 2, hepatitis B and C, cytomegalo-, herpes-6, and Epstein Barr viruses. Lymphocytes were fused with K6H6/B5 cells (ATCC, VA) using the CYTOPULSE CEEF-50 apparatus (Cyto Pulse Sciences, Inc., MD) at 1:1 lymphocytes to K6H6/B5 ratio.

After fusion, cells were seeded in flat-bottom 96-well microplates at ~5,000 cells/well in complete RPMI containing 10% heat inactivated FBS, 2 mM L-glutamine, 0.1 mM non-essential amino acids, 1 mM sodium pyruvate, 55 µM 2-mercaptoethanol (Invitrogen, CA), 100 µM hypoxanthine, 0.4 µM aminopterin, and 16 µM thymidine (HAT, Sigma, MO). Medium was replaced weekly and HAT selection was maintained until completion of antigen reactivity screening (3-5 weeks).

For the identification of antigen-reacting MAbs, ELISA-based screenings were performed robotically using a BIOMEK FX liquid handling system integrated with plate washer and spectrophotometer. Briefly, microtiter plates were coated at room temperature for 6 hours with 50 µL/well of in-house produced recombinant antigen (1 g/mL GM-CSF) diluted in coating buffer (50 mM carbonate-bicarbonate, pH 9.4). Plates were then blocked with binding buffer (PBS containing 1% BSA (Sigma, MO) and 0.05% Tween 20 (BioRad, CA)) for 2 hours at room temperature. Plates were washed once with washing buffer (PBS containing 0.05% Tween 20) and 50 µL/well of hybridoma supernatant was transferred into the ELISA plates. Binding reaction was carried out at room temperature for 2 hours. Subsequently, plates were washed 4 times and 100 µL of horseradish peroxidase (HRP)-conjugated goat anti-human IgG+M (Jackson ImmunoResearch Laboratories, PA) diluted 1:10,000 in binding buffer was added and reactions carried out at room temperature for 1.5 hours. Finally, plates were washed 4 times and 100 µL/well of SureBlue substrate (KPL, MD) was added for 10 min. Reactions were stopped by adding 50 µL/well of 1 N sulfuric acid and the absorbance was determined at 450 nm.

Fluorescent-Activated Cell Sorting (FACS) Analyses.

Figure 3:
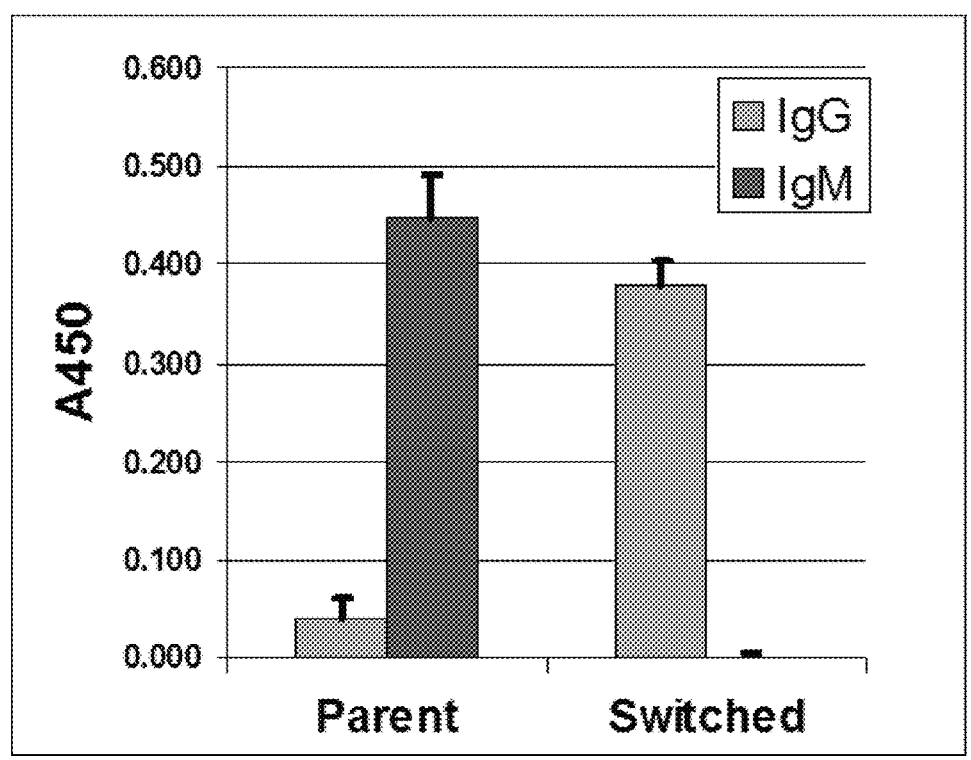
FIG. 3 demonstrates secretion of antigen-binding IgG by class-switched hybridoma cells. Hybridoma E5 cells (parent) were treated as described in Materials and Methods. Hybridoma clones that had class-switched (switched) were identified using an ELISPOT-based screening method. An ELISA measuring specific binding to human GM-CSF coated onto plates was carried out to assess binding of either IgM or IgG. Switched IgG MAbs exhibited comparable binding to antigen as the parental IgM.

Ig binding and cell washing steps were conducted using ice-cold binding buffer (DPBS) without calcium or magnesium, 0.5% BSA), reactions were set up in V-bottom microplates, and samples were analyzed using a FACSAria apparatus (BD Biosciences, NJ). For the FACS experiment shown in FIG. 3A, $10^6$ murine anti-GM-CSF hybridoma cells (Mul19/2) were loaded with 100 ng/reaction of GM-CSF and then incubated with anti-GM-CSF human MAb E5. The binding of GM-CSF specific MAbs were detected with 10 µg/mL FITC-labeled goat anti-human Ig (SouthernBiotech, AL). For the FACS experiment shown in FIG. 3B, the E10 hybridoma cells were washed and seeded at 500,000 cells/well in a volume of 90 µL. Ten µL of phycoerythrin (PE)-labeled GM-CSF (R&D System, MN) was then added in each well and cells were incubated on ice for one hour. For unlabeled GM-CSF competition, the hybridoma cells were pre-incubated with 5 µg/mL recombinant human GM-CSF (PeproTech, NJ) at room temperature for one hour, washed three times, and then incubated with PE-GM-CSF as above before analysis. For the FACS experiment shown in FIG. 4, A431 and A431-K5 cells (gift of Dr. Ira Pastan, National Cancer Institute) were stained with 10 µg/mL of C12 MAb or normal human IgM (Jackson ImmunoResearch Laboratories, PA) diluted in binding buffer and reactions were carried out as above.

GM-CSF Neutralization Bioassay.

The GM-CSF-dependent human erythroleukemia cell line TF-1 (ATCC, VA) was grown in complete RPMI 1640 (see above) containing 10 ng/mL recombinant human GM-CSF (PeproTech, NJ). On the day preceding the experiment, TF-1 cells were grown in 0.1% FBS in the absence of GM-CSF. Starved cells were washed twice, resuspended in assay medium, and seeded in 96-well microplates at a concentration of 10,000 cell/well. Wells contained either assay medium, 100 pg/mL GM-CSF, or GM-CSF pre-incubated for one hour with test or isotype control Ig at concentrations indicated in the figure legends. After 3 days, 40 µL of Cell Titer reagent (Promega, WI) was added to each well, and plates were further incubated at 37° C. for 1 hour. Optical density (O.D.) was measured at 490 nm in spectrophotometer and medium background was subtracted to all samples. Percentage of GM-CSF neutralization was calculated as follows: 100−(O.D. with Ig/O.D. without Ig×100).

Antibody class-switch. Hybridoma cells were washed once with 10 mL PBS, resuspended in complete RPMI, seeded into flat bottom 96-well microplates and incubated at 37° C. in 5% $CO_2$. After four days, cells were resuspended by pipetting and 100 µL transferred to 20 ELISPOT plates (Millipore, MA) coated with 2.3 g/mL goat anti-human IgG (H+L) (Jackson Immunoresearch, PA). The remaining cells in the tissue plates were fed with an additional 100 µL complete RPMI. After overnight incubation, ELISPOT plates were washed three times with PBS containing 0.05% Tween (PBST), then 100 µL of 2 g/mL goat anti-human IgG (H+L)-HRP was added and the plates incubated one hour at room temperature with shaking. Plates were washed three times with PBST then 100 µL of AEC substrate solution (Sigma, St. Louis, Mo.) was added to wells and incubated 90 minutes at room temperature with shaking. Substrate was aspirated and plates were washed with $dH_2O$ and allowed to air dry. Clones from wells exhibiting positive spots (indicating IgG production) were expanded. The above step was sequentially repeated by reseeding positive clones at 1000, 100, 10, and 0.25 cells/well while tracking positive wells until a single-cell colony was identified that secreted IgG.

Fermentation Using Hollow Fibers and Stirred Bioreactor.

Cells were seeded at $2.5 \times 10^5$/mL in a 2 L bioreactor (B Braun Stat B-DU) containing 1 L HyQCDM4NS0 serum free medium (HyClone, UT) maintaining glucose and glutamine at 6 g/L and 4 mM respectively. Controlled set points were: pH 7.1, $dO_2$ 40% saturation with air, temperature 37° C., and agitation rates at 80 rpm. Two mLs of sample was harvested daily, 1 mL for cell counting using a Cedex apparatus, and 1 mL used to measure Ig concentrations by ELISA. For the hollow fiber run, $10^8$ viable cells were seeded in a FiberCell system (Bellco, NJ) containing 15 mL of complete RPMI and re-fed using an inline reservoir containing one liter of fresh medium when 50% of the glucose was consumed.

Mismatch Repair Inhibition to Increase Genetic Diversity of Hybridoma Lines.

Hybridoma cells were grown in complete RPMI (negative control) or complete RPMI containing 250 µM or 500 µM of MMR-inhibiting anthracene compound. Cells were passed at a 1:5 dilution every three to four days in fresh media with or without morphocene and after three weeks cells were harvested and resuspended at $2 \times 10^6$ cells/mL in FACS buffer (PBS with 1% BSA). Cells were stained with 10 g/mL FITC-conjugated goat anti-human Ig (Jackson Immunoresearch) for 30 minutes on ice. Cells were washed with 10 mL ice cold FACS buffer and resuspended in 3 mL FACS buffer. 10 µL Viaprobe (Becton Dickinson, Franklin Lakes, N.J.) was added for 5 minutes on ice and viable cells were sorted for high Ig surface staining on a FACSAria cell sorter (Becton Dickinson). The gate was set to sort cells representing the 5% subpopulation with the highest Ig surface staining. For selection of clones with enhanced titers, FACS sorted cells were seeded in U-bottom 96 well plates and incubated for one week at 37° C. in 5% $CO_2$. Fifty L of supernatants were harvested from wells and analyzed for IgM production via ELISA using goat anti-human IgM+G coated plates. As an internal control, 3 wells of each ELISA plate were seeded with 50 µL of 10 ng/mL human IgM (Jackson Immunoresearch). O.D. values obtained at 450 nm were normalized to the mean values of internal control wells. Wells exhibiting high IgM signals were expanded for further analysis. For microsatellite instability (MSI) analysis, DNA was extracted from parental or morphocene-treated cells using the Qiagen DNeasy Tissue kit (Qiagen). The BAT poly A repeat marker (7) was amplified using the D4 fluorescent-labeled BAT-26-F (5'-tcaccatccattgcacagtt-3') (SEQ ID NO:20) and BAT-26-R (5'-ctgcgagaaggtact-caccc-3') (SEQ ID NO:21) primers, pfuUltra™ high-fidelity polymerase (Stratagene, CA), and reactions incubated as follows: 5 min. at 95° C.; 9 cycles of 1 min. at 94° C., 1 min. at 60° C. and 2 min. at 72° C., with the annealing temperature decreasing by 1° C. each cycle; 30 cycles of 1 min. at 94° C., 1 min. at 52° C., and 2 min. at 72° C.; final extension of 10 min. at 72° C. Single-copies of the marker allele were obtained by using a dilution of DNA that yielded an amplicon in only 50% of the PCR reactions. PCR products were diluted 1:10 with CEQ sample load solution and then loaded into the Beckman CEQ 8000 Genetic Analysis System for fragment analysis.

Generation of Antigen-Specific Human MAbs.

Ex-vivo immunizations were carried out using cryopreserved B-cells obtained from volunteer subjects (healthy donors) as described above. Alternatively, B-cells were obtained from human subjects whose sera contained high titers of MAbs specific to an antigen of interest. The rationale of the latter approach stems from the possibility that some antigen-specific MAbs could result from an abnormal immune response (as in the case of autoimmune patients), or derive from an in vivo immune response to tumor, microbial, or vaccine antigens.

Figure 2A:
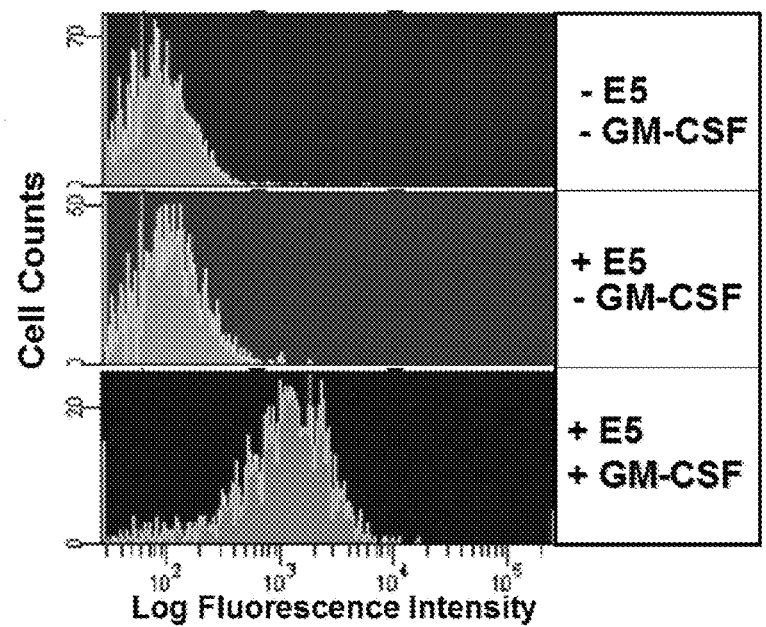
FIGS. 2A and 2B illustrate the high specificity of human MAbs to native human GM-CSF.
Figure 2B:
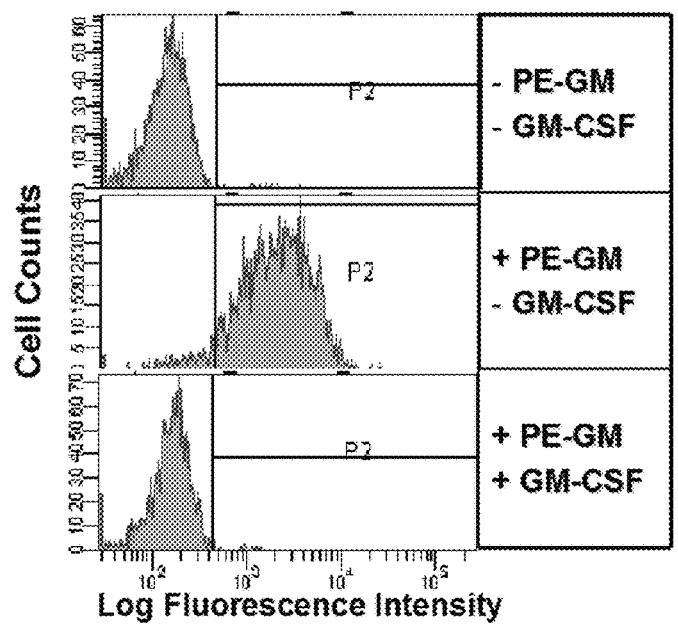

Several antigen-reacting human MAbs were identified after fusion of ex-vivo immunized cells and from hybridoma libraries generated from PAP patients B-cells. Four hybridoma lines, E5 (IgM), G7 (IgM), E10 (IgG), and G9 (IgG) were selected for further studies and the human MAbs they produce were tested for specificity by ELISA. FIG. 1 shows that E5, G7, and E10 human MAbs only reacted with human GM-CSF and none of the other ten unrelated antigens tested, including murine GM-CSF, which shares a 53% identity with the human homolog. Similar results were obtained for the G9 hybridoma. FACS analyses were carried out to confirm specificity of these human MAbs. Human GM-CSF was allowed to bind to the surface of mouse hybridoma cells, which express membrane bound-MAbs specific to human GM-CSF at a different epitope. E5 MAb bound the surface of these cells under these conditions, as indicated by the fluorescence intensity shift (FIG. 2A, bottom panel). This result demonstrates the ability of E5 MAb to bind native human GM-CSF. In absence of cell-bound GM-CSF, E5 MAb did not cross-react with any of the membrane bound proteins expressed by these hybridoma cells (FIG. 2A, middle panel). Similarly, E10 MAb showed high specificity via FACS analysis. In addition, since E10 MAb was found associated to the hybridoma cell membrane, its ability to bind soluble, phycoerythrin (PE)-labeled GM-CSF was shown by FACS (FIG. 2B, middle panel). Binding specificity was demonstrated by pre-incubation of the E10 hybridoma cells with an excess of unlabeled GM-CSF (FIG. 2B, lower panel).

De Novo Class-Switch of Human MAbs.

Using the two strategies described above, IgG and IgM human MAbs to a variety of human and nonhuman antigens have been generated. Although most therapeutic antibodies in the market are of the IgG isotype, cancer trials testing potentially therapeutic IgM MAbs have shown regression of tumors in vivo (16, 17). These clinical responses can be attributable to the ability of IgM to strongly fix and activate the complement pathway and effectively kill tumor cells. IgG binds to the Fc receptors on macrophages and NK cells and thus can mediate ADCC activity against tumor cells. Both IgG and IgM with identical specificity (same antigen and epitope) can be tested for best pharmacological activity in vivo. In the case where an IgG isotype is preferred, a quick robust procedure (see Materials and Methods) for de novo class-switching of IgM has been followed. Using the E5 line as an example, a subset of cells that had class-switched to an IgG isotype under the growth conditions used was identified. The E5 IgG showed identical nucleotide sequence in its variable region and similar reactivity to GM-CSF (FIG. 3) as the parental E5 IgM.

Biological Activities of Human MAbs.

Figure 4:
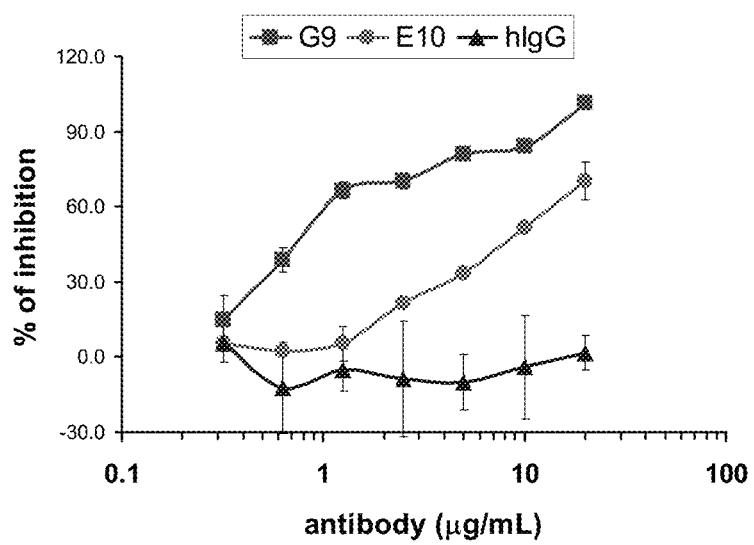
FIG. 4 demonstrates GM-CSF-dependent growth inhibition of TF-1 cell lines with fully human MAbs. The human GM-CSF-dependent human erythroleukemia cell line TF-1 (ATCC, VA) was grown in complete RPMI 1640 containing 10 ng/mL recombinant human GM-CSF (PeproTech, NJ). On the day preceding the experiment, TF-1 cells were grown in 0.1% FBS in the absence of GM-CSF. The starved TF-1 cells were harvested and washed twice with assay medium (plain RPMI with 0.5% BSA). Cells were resuspended in assay medium and seeded in 96-well microplates at a concentration of 10,000 cell/well. Wells contained either assay medium, 100 pg/mL GM-CSF, or GM-CSF pre-incubated for one hour with test or isotype control Igs at concentrations indicated in the figure. After 3 days, 40 µL of Cell Titer reagent (Promega, WI) was added to each well, and plates were further incubated at 37° C. for 1 hour. Optical density (O.D.) was measured at 490 nm in spectrophotometer and medium background was subtracted from samples. Percentage of GM-CSF neutralization was calculated as follows: 100−[O.D. with Ig/O.D. without Ig)×100].

Pharmacological properties sought for therapeutic MAbs that target soluble mediators of disease include the ability to neutralize growth factors. As mentioned above, one such example is GM-CSF as a mediator of RA (9-11). The ability of the human MAbs to block GM-CSF function using a cell-based assay whereby the growth of human erythroblastoid cells (TF1) is dependent on the presence of this cytokine in their culture medium was assessed. As shown in FIG. 4, both E10 and G9 significantly inhibited GM-CSF-dependent cell growth, whereas the human IgG isotype control showed no effect. The difference in potency seen between E10 and G9 correlates well with their apparent affinities of 870 and 14 picomolar, respectively. The E5 MAb only showed minimal neutralizing activity consistent with its lower affinity (5 nM).

Assessment of Titers and Stability of Hybridomas Secreting Human MAbs.

Figure 5A:
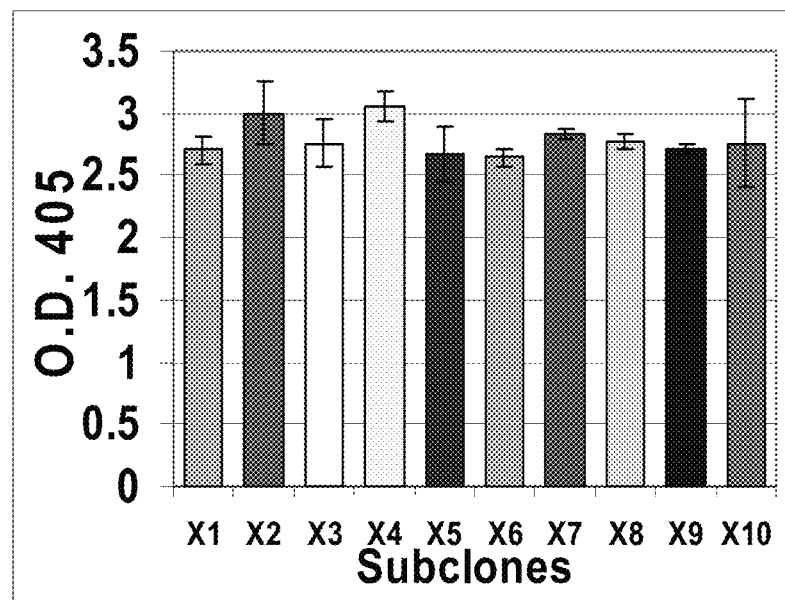
FIG. 5A illustrates ELISA results demonstrating that all E5-3D2 subclones tested secrete high levels of Ig. The hybridoma E5-3D2 line was grown for 60 generations and then stability of production was assessed by analyzing frequency of producing cells. Subclones (X1-X10) derived from 3D2 cells via limiting dilution were randomly chosen and their Ig production measured using an ELISA-based assay. Absorbance at 405 nm was normalized for colony size by visual inspection of the cell-containing wells.
Figure 5B:
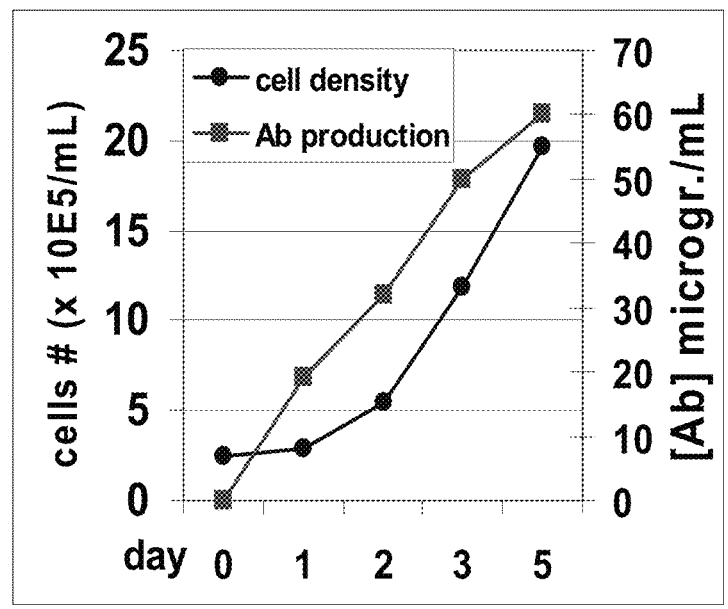
FIG. 5B demonstrates that the specific productivity measured during the log phase was 24 pg/cell/day following inoculation of 3D2 cells in a stirred bioreactor containing 1 liter of serum-free medium and Ig production and recordation of number of viable cells on day 1 through 5.

An important property of a MAb manufacturing line is stability of Ig secretion during the entire batch manufacturing cycle. In one scenario where the cycle duration is about two months, a line doubling every 24 hours would go through about 60 generations from thawing to harvest. An E5 line was used as a model for testing MAb titers and production stability of hybridoma generated using our method. A clone derived from this line, 3D2, showed a doubling time of 24 hours and was re-cloned by limiting dilutions after more than two months of continuous culturing. The frequency of producing clones was determined via ELISA, measuring Ig concentrations in their conditioned media normalized for cell densities. FIG. 5A shows that all E5-3D2 subclones tested secrete high levels of Ig, demonstrating homogeneous retention of Ig production in this cell population after 60 generations. Ig production was then assessed using a small scale (15 mL) hollow fiber system. Cells were inoculated in a hollow fiber cartridge and continuously fed using an inline reservoir containing one liter of fresh medium. Starting on day 5, all conditioned medium from the cartridge (15 mL) was harvested daily and replaced with fresh medium. Fermentation was carried out for additional 4 days, while daily Ig titers were determined by ELISA using an Ig standard of known concentration. A cumulative titer of 1.2 g/L during the 4-day run was recorded. Between day 8 and 9, glucose consumption was at its peak (2 gram/L a day), indicating that cells tolerated well the extremely high cell densities. Production performance was also evaluated in a 1-liter scale fed-batch run using a stirred bioreactor system. Cells from a frozen ampule were first thawed and inoculated in a shake flask and later seeded in stirred bioreactor (Bauer) containing 1 liter of serum-free medium. Fermentation was carried out until cell viability dropped below 60% (day 6). Ig production and cell densities were recorded between day 1 and 5 and are shown in FIG. 5B. During the log phase (day 1-4), a specific productivity of 24 pg/cell/day with a doubling time averaging 23.4 hours was measured, suggesting good scalability of these cells from flask to bioreactor while maintaining higher titers.

Genetic Optimization of Hybridoma Secreting Human MAbs Via Mismatch Repair Regulation.

Figure 6A:
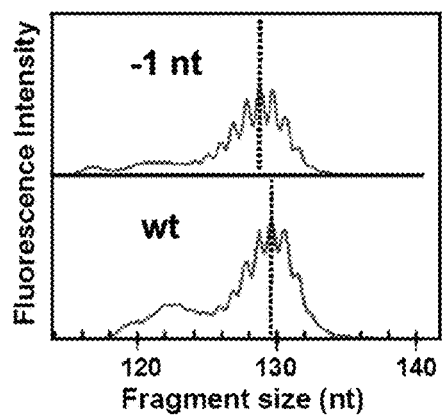
FIG. 6A shows results of an example of a single nucleotide deletion in the BAT marker found in E5 hybridoma cells treated with mismatch repair inhibitors. Dotted lines crossing the central peak in the histogram represent the size of wild type (wt) or contracted (−1 nt) fragment.
Figure 6B:
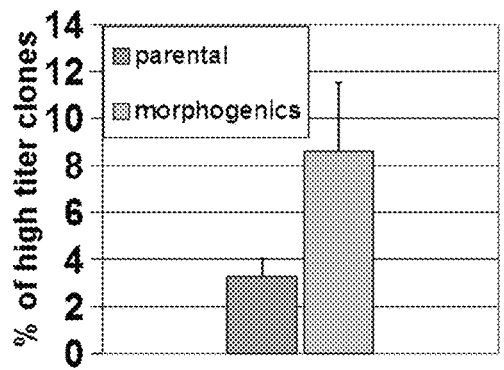
In FIG. 6B, parental and mismatch repair-inhibited cells were seeded in microplates to yield 3,763 and 2,437 Ig-secreting clones (O.D.>0.2), respectively. Ig concentrations were determined by ELISA and the frequency of clones with O.D. values greater than 1 was recorded and expressed as percentage of total number of clones screened.
Figure 7:
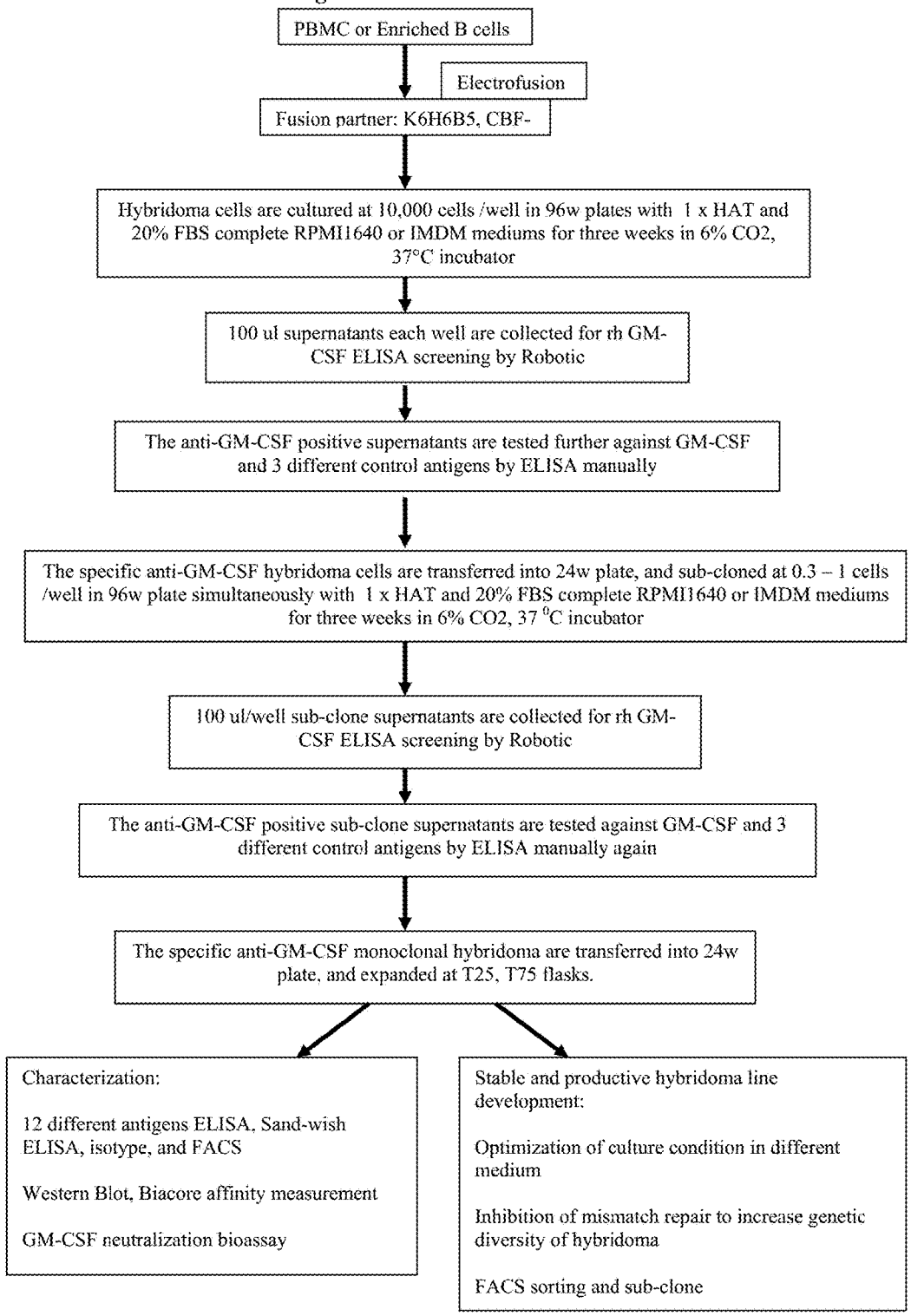
FIG. 7 provides a diagrammatic flow chart describing each step for the generation of a fully human hybridoma cell line.

The usefulness of improving the quality of MAb-producing cell lines using a process, termed morphogenics, which entails the transient regulation of MMR has been previously demonstrated (Nicolaides et al. (1995) Genomics 30:195-206; and, Nicolaides et al. (1998) Mol. Cell. Biol. 18:1635-41.). After increasing the genetic diversity of the cell pool using this method, high throughput screenings were carried out to identify subclones exhibiting higher titer, affinity (Grasso et al. (2004) Bioprocess Int. 2:58-64; and, Nicolaides et al. (2005) Ann. N.Y. Acad. Sci. 1059:1-11), or enhanced growth rates (Grasso, L. personal observation). E5 cells were subjected to morphogenics to demonstrate the ability to increase phenotypic diversity in the MAb-secreting lines generated using our hybridoma strategy. MMR inhibition was monitored by detecting microsatellite instability (MSI) in the BAT poly-A repeat marker. Of the 24 BAT alleles analyzed in cells exposed to the morphogenics process, 3 alleles showed alterations that included single nucleotide deletions, shown in FIG. 6A, and insertions. No MSI was detected in any of the 24 BAT alleles in parental cells. Subsequently, parental or morphogenics-treated cells were seeded by limiting dilutions in microplates. Cell clones were allowed to secret MAbs for one week and their conditioned medium analyzed for Ig concentrations by ELISA. The frequency of clones with O.D. greater than 1 (high Ig secretion) was determined from the total number of clones screened (3,763 for parental and 2,437 for morphocene pool) and found to have increased by 260% (p=0.0014) in the morphogenics-treated population (FIG. 6B).

Summary

This study represents a viable strategy for developing human MAbs for immunotherapies using an optimized ex-vivo immunization and human B-cell immortalization process combined with inhibition of mismatch repair. With this approach, highly specific and biologically active MAbs secreted by stable hybridoma lines can be generated.

According to the methods of the invention, stable MAb production for over 60 doublings and production of over 1 gram of MAb per liter during a 4-day hollow fiber fermentation run has been achieved, suggesting that hybridoma cells generated by the present methods are suited for perfusion systems and potentially large scale manufacturing. Moreover, hybridomas generated by this process have performed well in fed-batch bioreactor runs, suggesting a potential use of these lines for commercial applications. In summary, the platform process presented here offers an alternative approach for a rapid and cost-effective development of good quality, fully human antibodies for immunotherapeutic use.

Example 2

Generation of Fully Human Anti-GM-CSF Antibody; Isolation of PAP Cells

Patients with adult human pulmonary alveolar proteinosis (PAP) accumulate phospholipids and surfactant proteins in the alveoli. It has been hypothesized that PAP is due to the inability of the alveolar macrophages and type II epithelial cells to clear excess surfactant. As described above, the role for GM-CSF in the control of lung surfactant homeostasis has been established in the murine model and by extension is causative of the human pathology. Furthermore, patients with PAP have been shown to have circulating, neutralizing antibodies to GM-CSF, thereby implicating this cytokine as causative of the disease. Whether this autoimmune response is specific for GM-CSF is unclear. However, it has been shown that a subset of PAP patients improve with GM-CSF therapy, supporting the hypothesis that the absence of GM-CSF either by gene disruption or antibody-mediated neutralization results in the development of PAP.

Isolation of GM-CSF-Specific Antibodies.

Peripheral blood mononuclear cells (PBMCs) were isolated from PAP patients. Briefly, the PAP patient's B cells were recovered from the whole blood. The whole blood was diluted with equal volume PBS-/- and the contents was mixed gently by inverting the container. 25 ml diluted blood was overlayed onto a 50 ml tube that contained 25 ml Ficoll-Paque (Amersham Biosciences AB, Uppsala Sweden). The tubes were centrifuged at 2,000 rpm for 30 mins at room temperature. PBMCs were collected from the interface layer using a 10-ml pipette, transferred to new 50-ml tubes, and washed twice with PBS-/-. The PBMC pellet was re-suspended in 10 ml ACK Lysing Buffer (150 mM $NH_4Cl$, 10 mM $KHCO_3$, 0.1 mM $Na_2EDTA$, pH 7.2), incubated for 5 min. at room temperature to lyse the red cells, and washed twice with PBS-/-.

Fusion of PAP B-Cells with Myeloma Cell Line to Generate Hybridoma.

Enriched B-cells from PAP patients were fused with a variety of myeloma cells (human-mouse heterohybridoma, ATCC, VA, USA); CBF-7 cells (human-mouse heterohybridoma); HEK293; human myeloma cells by the following method. The B cells and fusion partner cells should have good viability (≥90% viable and in log phase). Both cell types in their original medium were counted and mixed in 15 ml tubes at 1:1 ratio, followed by centrifugation at 1,000 RPM for 6 min at 4° C. Cells were washed 3 times using 10-15 ml cold CPFM (CYTOPULSE fusion medium, Cyto Pulse Sciences, MD USA). The final pellet was resuspended in $10 \times 10^6$ cells/ml CPFM. Electro-fusion was performed using CYTOPULSE CEEF-50 (Cyto Pulse Sciences, MD USA). Fusion parameters were optimized following manufacturer and empirical guidelines, and fusion efficiency averaged one hybrid in 5,000 cells pulsed. After fusion, cells were seeded in flat-bottom 96-well microplates at ~5,000 cell/well in complete RPMI containing 10% heat inactivated FBS, 100 µM hypoxanthine, 0.4 µM aminopterin, and 16 µM thymidine (HAT, Sigma, MO USA). Medium was replaced weekly and HAT selection was maintained until completion of antigen reactivity.

ELISA Screening Assay.

For the identification of antigen-reacting MAbs, ELISA-based screenings were performed robotically using a BIOMEK FX liquid handling system integrated with plate washer and spectrophotometer. Briefly, microtiter plates were coated at room temperature for 6 hours with 50 µL/well of in-house produced recombinant antigens (1 µg/mL GM-CSF) diluted in coating buffer (50 mM carbonate-bicarbonate, pH 9.4). Plates were then blocked with binding buffer (PBS containing 3% BSA (Sigma, MO) and 0.05% Tween 20 (BioRad, CA)) for 2 hours at room temperature. Plates were washed once with washing buffer (PBS containing 0.05% Tween 20) and 50 µL/well of hybridoma supernatant was transferred into the ELISA plates. Binding reaction was carried out at room temperature for 2 hours. Subsequently, plates were washed 4 times and 100 µL of HRP-conjugated goat anti-human IgG+M (Jackson ImmunoResearch Laboratories, PA) diluted 1:10,000 in binding buffer was added and reactions carried out at room temperature for 1.5 hours. Finally, plates were washed 4 times and 100 µL/well of SUREBLUE substrate (KPL, MD) was added for 10 min. Reactions were stopped by adding 50 µL/well of 1 N sulfuric acid and the absorbance was determined at 450 nm.

FACS Analysis and Sorting.

Figure 9:
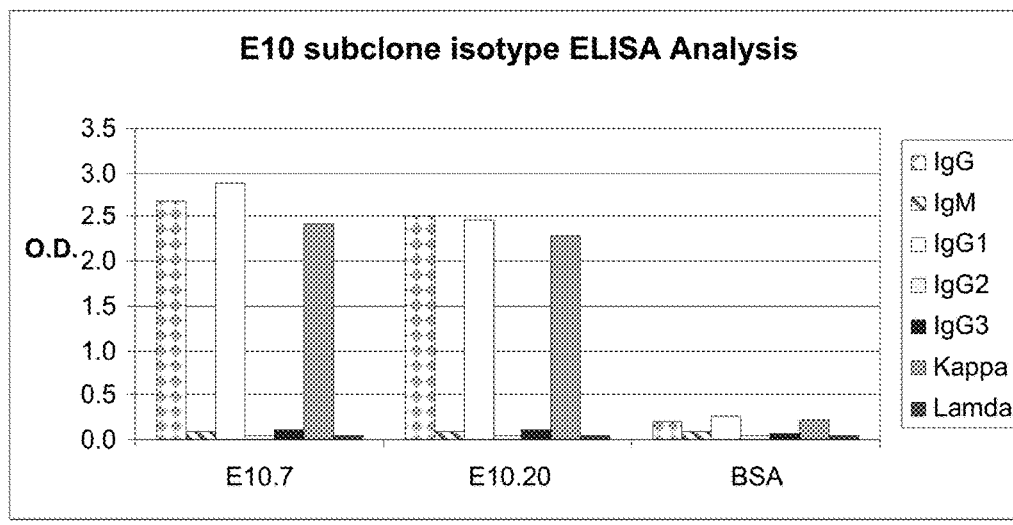
FIG. 9 demonstrates isotype determination of MAb E10. To determine the isotype of E10, a standard analysis was performed using anti-human IgG, IgG1, IgG2, IgG3, IgM, Lκ, and Lλ Fc specific antibodies to derive the isotype.

In every study, Ig binding and cell washing steps were conducted using ice-cold binding buffer (DPBS without calcium or magnesium, 0.5% BSA). The PBMC or hybridoma cells were washed and seeded at 500,000 cell/well. The FITC and phycoerythrin (PE)-labeled anti-human CD3, CD19, CD20 (SouthernBiotech, AL), and PE-labeled GM-CSF (R&D System, MN) were added (10-100 diluted), and incubated on ice for one hour. The cells were then washed three times with binding buffer, and analyzed or sorted using a FACSARIA apparatus (BD Biosciences, NJ). Results of isotype analysis of Mab E10 are shown in FIG. 9. To determine the isotype of E10, a standard analysis was performed using anti-human IgG, IgG1, IgG2, IgG3, IgM, Lκ, and Lλ Fc specific antibodies to derive the isotype.

GM-CSF Neutralization Bioassay.

The human GM-CSF-dependent human erythroleukemia cell line TF-1 (ATCC, VA) was grown in complete RPMI 1640 (see above) containing 10 ng/mL recombinant human GM-CSF (PeproTech, NJ). On the day preceding the experiment, TF-1 cells were grown in 0.5% FBS in the absence of GM-CSF. The starved TF-1 cells were harvested and washed twice with assay medium (plain RPMI with 0.5% BSA). Cells were resuspended in assay medium and seeded in 96-well microplates at a concentration of 10,000 cells/well. Wells contained either assay medium, 100 pg/mL GM-CSF, or GM-CSF pre-incubated for one hour with test or isotype control Igs at concentrations indicated in the figure. After 3 days, 40 µL of Cell Titer reagent (Promega, WI) was added to each well, and plates were further incubated at 37° C. for 1 hour. Optical density (O.D.) was measured at 490 nm in a spectrophotometer and medium background was subtracted from all samples. Percentage of GM-CSF neutralization was calculated as follows: 100−[(O.D. with Ig/O.D. without Ig)×100)]. FIG. 4 demonstrates GM-CSF-dependent growth inhibition of TF-1 cell lines with fully human MAbs.

Inhibition of Mismatch Repair to Increase Genetic Diversity of Hybridoma Cell Lines.

Inhibition of mismatch repair can lead to genetically diverse sibling cells with enhanced production, cell growth, or antibody activity. To improve MAb activity and cell growth, hybridoma cells were grown in complete RPMI (negative control) or complete RPMI containing 250 µM or 500 uM of the mismatch repair inhibitor morphocene (9,10-dimethyl anthracene, MP Biomedicals, CA). Cells were passed at a 1:5 dilution every three to four days in fresh media with or without morphocene and after three weeks cells were harvested and resuspended at 2×10⁶ cells/mL in FACS buffer (PBS with 1% BSA). Cells were stained with 10 g/mL FITC-conjugated goat anti-human Ig (Jackson Immunoresearch) for 30 minutes on ice. Cells were washed with 10 mL ice cold FACS buffer and resuspended in 3 mL FACS buffer. 10 L VIAPROBE (Becton Dickinson, Franklin Lakes, N.J.) was added for 5 minutes on ice and viable cells were sorted for high Ig surface staining on a FACSARIA cell sorter (Becton Dickinson). The gate was set to sort cells representing the 5% sub-population with the highest Ig surface staining. This population was expanded for one week in the presence or absence of chemical inhibitor of mismatch repair (MMR) and the procedure repeated two additional times. For selection of clones with enhanced titers, FACS sorted cells were seeded in U-bottom 96 well plates at 0.8 cells/well in 200 µL complete RPMI. Plates were incubated for one week at 37° C. in 5% CO$_2$. 50 µL of supernatants were harvested from wells and analyzed for IgM production via ELISA using goat anti-human IgM+G coated plates. As an internal control, 3 wells of each ELISA plate were seeded with 50 µL of 10 ng/mL human IgM (Jackson Immunoresearch). O.D. values obtained at 450 nm were normalized to the mean values of internal control wells. Wells exhibiting high IgM signals were expanded for further analysis. For MSI analysis, DNA was extracted from parental or MMR inhibitor-treated cells using the Qiagen DNeasy Tissue kit (Qiagen). The BAT poly A repeat marker was amplified using the D4 fluorescent-labeled mBAT-26-F (5'-tcaccatccattgcacagtt-3') (SEQ ID NO:20) and mBAT-26-R (5'-ctgcgagaaggtactcaccc-3') (SEQ ID NO:21) primers, pfuUltra™ high-fidelity polymerase (Stratagene, CA), and reactions incubated as follows: 5 min. at 95° C.; 9 cycles of 1 min. at 94° C., 1 min. at 60° C. and 2 min. at 72° C., with the annealing temperature decreasing by 1° C. each cycle; 30 cycles of 1 min. at 94° C., 1 min. at 52° C., and 2 min. at 72° C.; final extension of 10 min. at 72° C. Single-copy of the marker's alleles were obtained by using a dilution of DNA that yielded an amplicon in only 50% of the PCR reactions. PCR products were diluted 1:10 with CEQ sample load solution and then loaded into the Beckman CEQ 8000 Genetic Analysis System for fragment analysis. (Blake et al. Stepwise deletions of polyA sequences in mismatch repair-deficient colorectal cancers. (2001) Am. J. Pathol. 158:1867-70.)

Example 3

Generation of Monoclonal Antibody E10 with High Specificity to GM-CSF

Several antibodies were derived from B-cells of patients with PAP. These antibodies were of the IgM, IgG isotype. Each of these antibodies were found to specifically bind to GM-CSF using the assays for specificity described herein. One anti-GM-CSF human IgG1 monoclonal antibody E10 was generated from Pulmonary alveolar proteinosis (PAP) patient's B cells fused with either myeloma cells then subsequently screened for anti-human GM-CSF monoclonal antibodies by ELISA as described above.

Blood from a PAP patient (91 ml whole blood) was used to isolate a total of 49.5 million PBMCs. The viability of these cells was 99.0%. The results from a FACS analysis are shown in Table 2. The B cells were expanded by culturing approximately 25 million PBMCs in cRPMI1640 (10 ml) with IL-4 2 ng/ml (PeproTech), transferrin 50 ug/ml (Sigma), PMA 5 ng/ml (Sigma), and cyclosporine A 0.5 ug/ml (Sigma) with feeder cells. After 11 days of culture, 12 million cells remained and were subsequently fused with a myeloma cell by electro-fusion (CytoPulse CEEF-50). FACS analysis results are set forth in Table 2.

TABLE 2

Generation of E10 monoclonal antibody and analysis by FACS

|  | FITC-CD3(%) | FITC-CD20(%) | PE-GMCSF(%) | CD20/GMCSF |
|---|---|---|---|---|
| PBMC | 62.6 | 14.4 | 5.9 | 6.3 |
| 11 day culture | 77.2 | 17.0 | 0.7 | 0.1 |

The fused cells were cultured in RPMI 1640 (Invitrogen, CA, USA) with 10% FBS, heat inactivated (JRH Biosciences, KS USA); L-glutamine, 200 mM (Invitrogen, CA, USA); non-essential amino acids, 10 mM (Invitrogen, CA, USA); sodium pyruvate solution, 100 mM (Invitrogen, CA, USA); Pen-Strep (Invitrogen, CA, USA); 2-Mercaptoethanol, 55 mM (Invitrogen, CA, USA); and 1×HAT (Sigma, MO USA).

After 12 days culture, about 48% of the hybridoma culture showed growth. Next, the hybridomas were screened using a GM-CSF specific ELISA with recombinant GM-CSF (PeproTech, NJ, USA). Several clones were isolated, including those that were positive for GM-CSF. These clones were tested again by ELISA to confirm that they were specific for the recombinant GM-CSF and not for tetanus toxin (TT). Clone 4E10 showed specifically reaction with GM-CSF, but not TT. Clone 4E10 was subsequently subcloned. After 3 weeks the cultured subclones were screened by ELISA to confirm specificity to GM-CSF was maintained and then further characterized as described below.

Characterization of E10.

Figure 8:
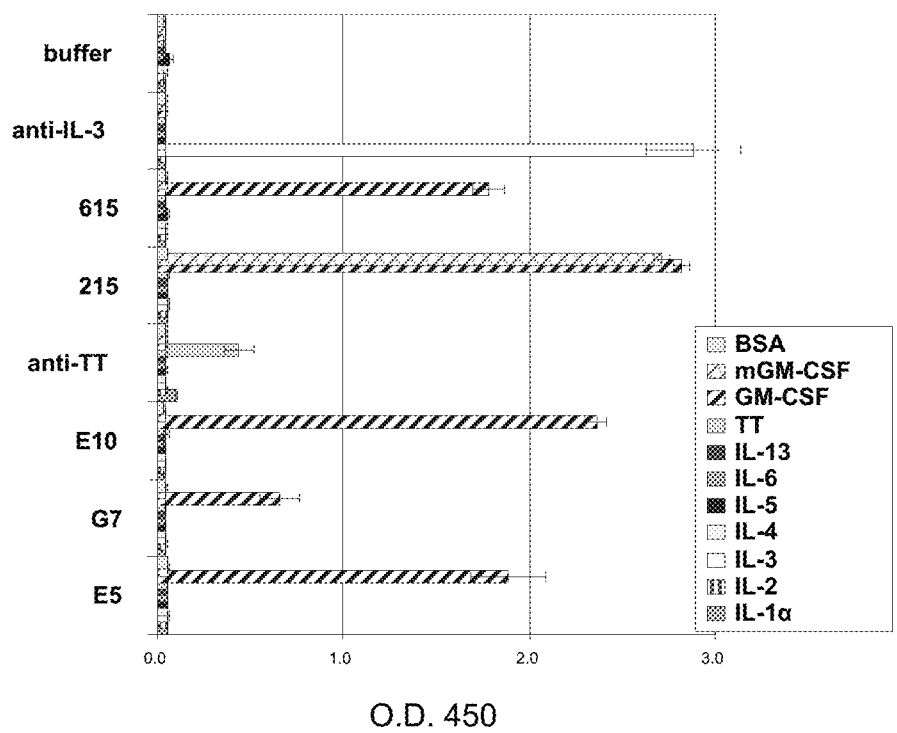
FIG. 8 illustrates an antigen panel ELISA for selection of antigen-specific human MAbs. Three GM-CSF specific huMAbs, E10, G9, and E5 (not described), reacted with human GM-CSF and none of the other antigens in the panel. Efficient antigen coating was optimized using specific MAbs to the various antigens for greater assay sensitivity. 615 and 215 are two anti-human GM-CSF murine MAbs.

To determine the specificity of the anti-GM-CSF antibodies E10, an antigen-specific ELISA was performed with a range of antigens (FIG. 8). FIG. 8 compares binding to the following antigens: hIL-1a, hIL-2, hIL-3, hIL-4, hIL-5, IL-6, hIL-13, hGM-CSF, mGM-CSF, BSA, and TT. In subsequent studies, the binding of anti-GM-CSF antibodies was compared to human GM-CSF, human Mesothilin, SEB, BGG, CAB, HEL, TT, BSA, Goat IgG, human mucin, and Mouse IgG (data not shown). In both studies 4E10 only reacted with human GM-CSF.

To determine the isotype of E10, a standard analysis was performed using anti-human IgG, IgG1, IgG2, IgG3, IgM, Lκ, and Lλ to derive the isotype. This analysis demonstrated that 4E10 is an IgG1 and Kappa antibody (see FIG. 9).

The ability of E10 to neutralize the biological activity of GM-CSF in vitro was tested by using a cell line, TF-1, that is dependent upon this cytokine for survival and growth (see FIG. 8). The human GM-CSF-dependent human erythroleukemia cell line TF-1 (ATCC, VA) was grown in complete RPMI 1640 containing 10 ng/mL recombinant human GM-CSF (PeproTech, NJ). On the day preceding the experiment, TF-1 cells were grown in 0.1% FBS in the absence of GM-CSF. The starved TF-1 cells were harvested and washed twice with assay medium (plain RPMI with 0.5% BSA). Cells were suspended in assay medium and seeded in 96-well microplates at a concentration of 10,000 cell/well. Wells contained either assay medium, 100 pg/mL GM-CSF, or GM-CSF pre-incubated for one hour with test or isotype control Igs at concentrations ranging from 20 g/mL to 0.315 g/mL. After 3 days, 40 uL of CELL TITER reagent (Promega, WI) was added to each well, and plates were further incubated at 37° C. for 1 hour. Optical density (O.D.) was measured at 490 nm in spectrophotometer and medium background was subtracted from all samples. Percentage of GM-CSF neutralization was calculated as follows: 100−[(O.D. with Ig/O.D. without Ig)×100]. The antibody 4E10 was capable of neutralizing the activity of GM-CSF in vitro at a concentration of 100 pg/ml.

Figure 10:
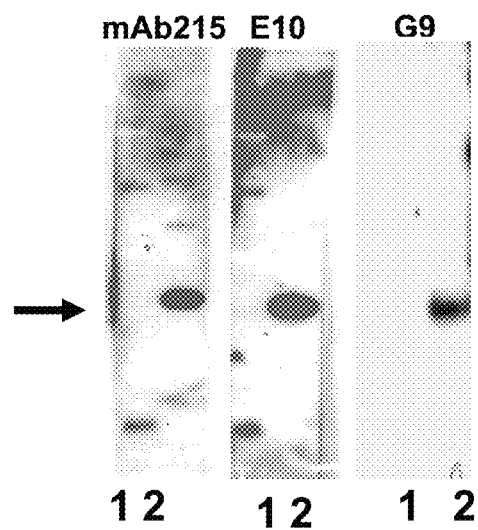
FIG. 10 shows a Western analysis with E10 and G9 MAbs. The western blot analyses were performed with E10 and G9 to determine if the antibodies would cross-react with human recombinant GM-CSF. The mAb215 is mouse anti-human GM-CSF neutralizing monoclonal antibody as a positive control, Lane: 1 were loaded with tumor cell lysate as negative protein control, Lane: 2 were loaded with 500 ng rh GM-CSF (PeProTech, NJ USA), As shown in FIG. 5 E10 and G9 reacted with human GM-CSF.

A Western blot analysis was performed with E10 to determine if the antibody would cross-react with human recombinant GM-CSF. As shown in FIG. 10, E10 cross-reacts with human GM-CSF under reducing conditions.

Figure 11:
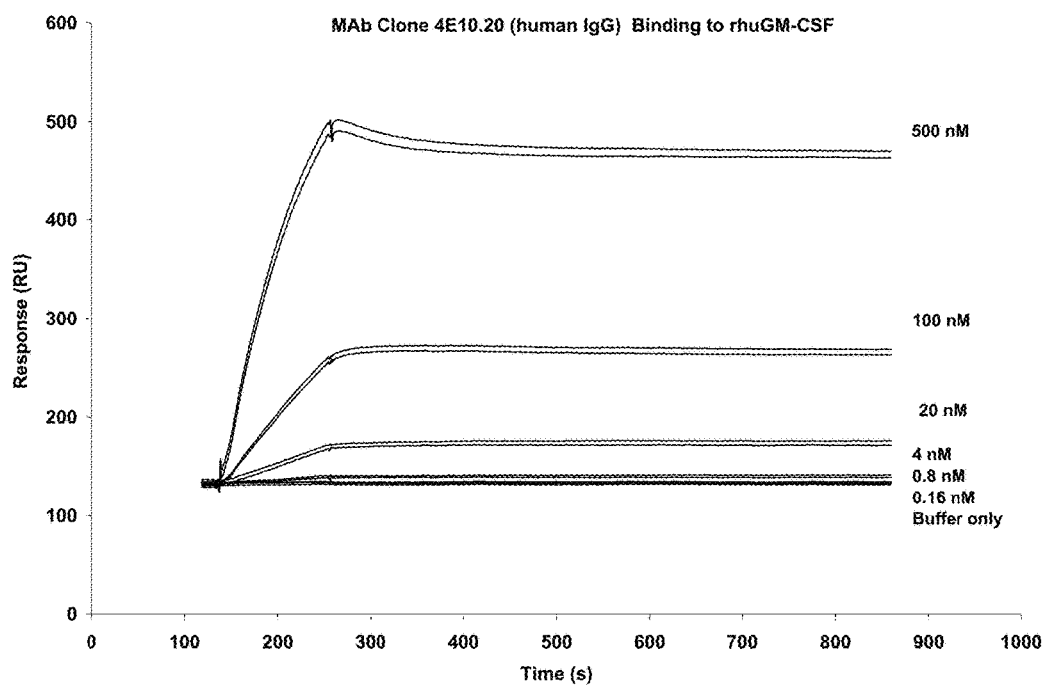
FIG. 11 shows a BIACORE analysis for E10. E10.20 had an association rate constant $(k_a)=2.47\times10^4$, a dissociation rate constant $(k_d)=2.16\times10^{-5}$ and an overall affinity $(K_D)$ of 0.87 nM.

To determine the binding affinity of E10, a BIACORE analysis was performed as follows. The binding constant for E10 is about 870 pM (FIG. 11).

Example 4

Generation of Monoclonal Antibody G9 with High Specificity to GM-CSF

The anti-GM-CSF human IgG1 monoclonal antibody G9 was generated from Pulmonary alveolar proteinosis (PAP) patient's B cells fused with either K6 or CBF-7 then subsequently screened for anti-human GM-CSF monoclonal antibodies by ELISA as described above.

Blood from a PAP patient (91 ml whole blood) was used to isolate a total of 49.5 million PBMCs. The viability of these cells was 99.0% (data not shown). The B cells were expanded by culturing approximately 25 million PBMCs in cRPMI1640 (10 ml) with IL-4 2 ng/ml (PeproTech); transferrin 50 ug/ml (Sigma); PMA 5 ng/ml (Sigma); and cyclosporine A 0.5 ug/ml (Sigma) with feeder cells. After 11 days of culture, 12 million cells remained and were subsequently fused to myeloma cells by electro-fusion (CytoPulse CEEF-50).

The fused cells were cultured in RPMI 1640 (Invitrogen, CA, USA) with 10% FBS, heat inactivated (JRH Biosciences, KS USA); L-glutamine, 200 mM (Invitrogen, CA, USA); non-essential amino acids, 10 mM (Invitrogen, CA, USA); sodium pyruvate solution, 100 mM (Invitrogen, CA, USA); Pen-Strep (Invitrogen, CA, USA); 2-Mercaptoethanol, 55 mM (Invitrogen, CA, USA); and 1×HAT (Sigma, MO USA).

After 12 days culture, about 48% of the hybridoma culture showed growth. Next, the hybridomas were screened using a GM-CSF-specific ELISA with recombinant GM-CSF (PeproTech, NJ, USA). Several clones were isolated, including those that were positive for GM-CSF. These clones were tested again by ELISA to confirm that they were specific for the recombinant GM-CSF and not for tetanus toxin (TT). The G9 population showed highly specific reactivity with GM-CSF, but not TT. Next, the G9 population was subcloned to obtain a pure culture. After 3 weeks the cultured subclones were screened by ELISA to confirm specificity to GM-CSF was maintained and then further characterized as described below.

Characterization of G9.

To determine the specificity of the anti-GM-CSF antibodies G9, an antigen specific ELISA was performed with a range of antigens (FIG. 8). FIG. 8 compares binding to the following antigens: hIL-1a, hIL-2, hIL-3, hIL-4, hIL-5, IL-6, hIL-13, hGM-CSF, mGM-CSF, BSA, and TT. In subsequent studies the binding of anti-GM-CSF antibodies was compared to human GM-CSF, human mesothelin, SEB, BGG, CAB, HEL, TT, BSA, Goat IgG, human mucin, and Mouse IgG (data not shown). In both studies G9 only reacted with human GM-CSF.

Figure 12:
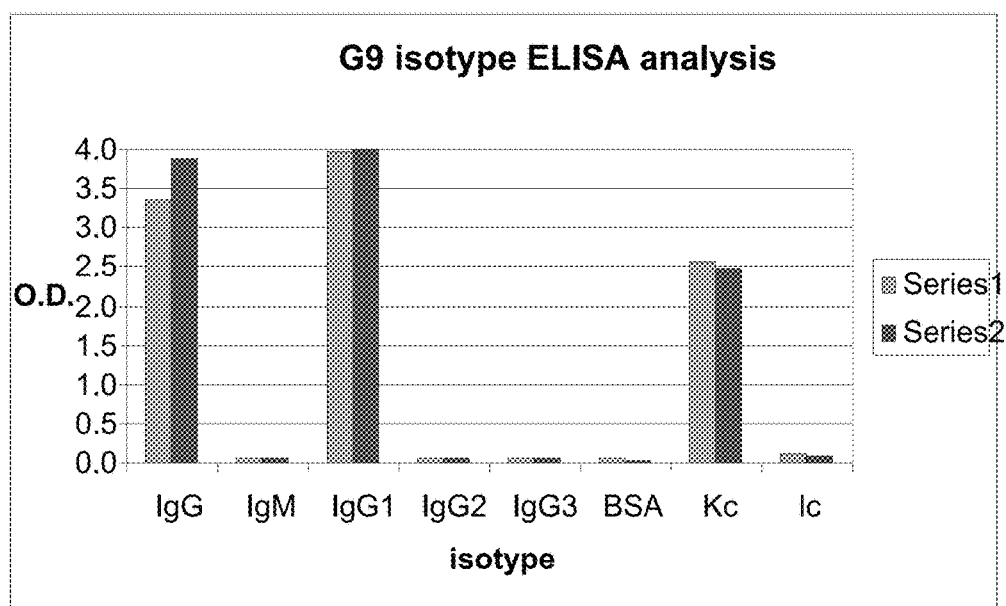
FIG. 12 demonstrates isotype determination of MAb G9. To determine the isotype of G9, a standard analysis was performed using anti-human IgG, IgG1, IgG2, IgG3, IgM, Lκ, and Lλ specific antibodies to derive the isotype (in double samples, FIG. 3).

To determine the isotype of G9, a standard analysis was performed using anti-human IgG, IgG1, IgG2, IgG3, IgM, Lκ, and Lλ to derive the isotype. This analysis demonstrated that G9 is an IgG1 and Kappa antibody (FIG. 12).

G9 Neutralization Bioassay.

The ability of G9 to neutralize the biological activity of GM-CSF in vitro was tested by using a cell line, TF-1, that is dependent upon this cytokine for survival and growth (FIG. 4). The human GM-CSF-dependent human erythroleukemia cell line TF-1 (ATCC, VA) was grown in complete RPMI 1640 containing 10 ng/mL recombinant human GM-CSF (PeproTech, NJ). On the day preceding the experiment, TF-1 cells were grown in 0.1% FBS in the absence of GM-CSF. The starved TF-1 cells were harvested and washed twice with assay medium (plain RPMI with 0.5% BSA). Cells were suspended in assay medium and seeded in 96-well microplates at a concentration of 10,000 cell/well. Wells contained either assay medium, 100 pg/mL GM-CSF, or GM-CSF pre-incubated for one hour with test or isotype control Igs at concentrations ranging from 20 g/mL to 0.315 g/mL. After 3 days, 40 uL of CELL TITER reagent (Promega, WI) was added to each well, and plates were further incubated at 37° C. for 1 hour. Optical density (O.D.) was measured at 490 nm in spectrophotometer and medium background was subtracted from all samples. Percentage of GM-CSF neutralization was calculated as follows: 100−[O.D. with Ig/O.D. without Ig)×100]. The antibody G9 was capable of neutralizing the activity of GM-CSF in vitro at a concentration of 100 pg/ml.

A Western blot analysis was performed with G9 to determine if the antibody would cross-react with human recombinant GM-CSF. As shown in FIG. 10, G9 cross-reacts with human GM-CSF under reducing conditions.

Figure 13:
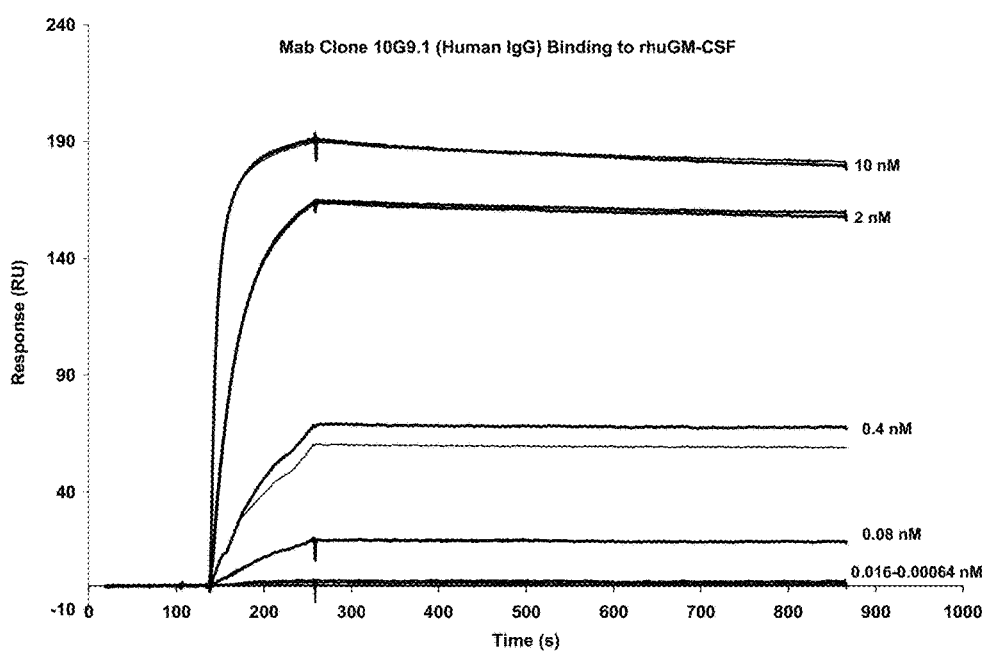
FIG. 13 shows a BIACORE analysis for G9. 10G9.1 had an association rate constant $(k_a)=8.47\times10^6$, a dissociation rate constant $(k_d)=9.27\times10^{-5}$ and an overall affinity $(K_D)$ of 0.87 nM.

To determine the binding affinity of G9, BIACORE analysis was performed as described above. The binding constant for G9 is about 11-17 pM (FIG. 13).

Example 5

Nucleotide Sequences Encoding Fully Human Anti-GM-CSF Antibody G9 and E10

Antibody G9. Nucleotide and amino acid sequences for fully human anti-GM-CSF antibody G9 was obtained by standard methods. Briefly, total RNA was isolated from hybridoma G9 using Trizol reagent (Invitrogen) according to the manufacturer's instructions. The message was synthesized to cDNA using Superscript II reverse transcriptase (Invitrogen) according to the manufacturer's instructions. To amplify the light and heavy chain variable regions, PCR reactions were carried out with Herculase DNA polymerase (Stratagene) using primers SEQ ID NO:22 and SEQ ID NO:23 for the light chain and SEQ ID NO:24 and SEQ ID NO:25 for the heavy chain. PCR products were cloned into pCR4-TOPO vector (Invitrogen), transformed into *E. coli* Mach1 cells and transformants selected on LB Kanamycin plates. Colonies were screened for inserts with the same primer pairs as above and four positive colonies each were used to generate template DNA for DNA sequence determination, using TempliPhi reagent (GE Healthcare). DNA inserts were sequenced with primers SEQ ID NO:26 and SEQ ID NO:27 using Beckman Coulter DTCS sequencing reagent followed by data acquisition and analysis on a Beckman Coulter CEQ2000. In order to add a leader peptide sequence to the light chain, a positive clone was re-amplified with primers SEQ ID NO:28 and SEQ ID NO:23 using Herculase DNA polymerase. To generate a full length heavy chain (SEQ ID NO: 11), including a leader peptide sequence, PCR was carried out with primers SEQ ID NO:29 and SEQ ID NO:30 using the original cDNA as template. The resulting PCR product was TA cloned, transformed into Mach1 cells and positive clones were identified as described above. Full length G9 heavy chain cDNA was sequenced with primers SEQ ID NO:25, SEQ ID NO:26, SEQ ID NO:31, SEQ ID NO:32, SEQ ID NO:33, SEQ ID NO:34, SEQ ID NO:27 and SEQ ID NO:30 using template DNA generated with TempliPhi reagent. The resulting DNA sequences for full length heavy chain for G9 (SEQ ID NO: 11) and full length light chain for G9 (SEQ ID NO: 15) are shown below. The predicted translation products derived from SEQ ID NO: 11 and SEQ ID NO:15 are shown in SEQ ID NO:9 and SEQ ID NO:13, respectively. The predicted translation products derived from SEQ ID NO:10 and SEQ ID NO:14 are shown in SEQ ID NO:8 and SEQ ID NO:12, respectively. The underlined sequences of SEQ ID NOs: 11 and 15 represent the leader sequence added by PCR. The polynucleotide sequences of SEQ ID NO: 10 and 14 encode the heavy and light chains of the G9 antibody, respectively, without the added leader sequences. The lower case sequences of SEQ ID NOs:9 and 13 represent the human leader peptides added by the PCR reaction. The underlined sequences of SEQ ID NOs: 8, 9, 12, and 13 represent the CDR regions. The remaining sequences of SEQ ID NOs:8, 9, 12 and 13 are the frameworks of the variable regions and the constant regions. The constant region for heavy chain starts with amino acid sequence WGQG (amino acid 111 of SEQ ID NO:8 or 130 of SEQ ID NO:9), and the constant region for the light chain starts with amino acid sequence FGQG (amino acid 98 of SEQ ID NO:12 or 117 of SEQ ID NO:13).

Antibody E10.

Nucleotide and amino acid sequences for fully human anti-GM-CSF antibody E10 was obtained by standard methods. Briefly, total RNA was isolated from hybridoma E10 using Trizol reagent (Invitrogen) according to the manufacturer's instructions. The message was synthesized to cDNA using Superscript II reverse transcriptase (Invitrogen) according to the manufacturer's instructions. To amplify the light and heavy chain variable regions, PCR reactions were carried out with Herculase DNA polymerase (Stratagene) using primers SEQ ID NO:22 and SEQ ID NO:23 for the light chain and SEQ ID NO:24 and SEQ ID NO:25 for the heavy chain. PCR products were cloned into pCR4-TOPO vector (Invitrogen), transformed into *E. coli* Mach1 cells and transformants selected on LB Kanamycin plates. Colonies were screened for inserts with the same primer pairs as above and four positive colonies each were used to generate template DNA for DNA sequence determination, using TempliPhi reagent (GE Healthcare). DNA inserts were sequenced with primers SEQ ID NO:26 and SEQ ID NO:27 using Beckman Coulter DTCS sequencing reagent followed by data acquisition and analysis on a Beckman Coulter CEQ2000. The resulting DNA sequences encoding the heavy chain variable region for E10 (SEQ ID NO: 17) and full length light chain for E10 (SEQ ID NO: 19) are shown below. The predicted translation products derived from SEQ ID NO:17 and SEQ ID NO:19 are shown in SEQ ID NO:16 and SEQ ID NO:18, respectively. The underlined sequences of SEQ ID NOs: 16 and 18 represent the CDR regions. The remaining sequences of SEQ ID NOs: 16 and 18 are the framework of the variable region and the constant regions. The constant region for heavy chain starts with amino acid sequence WGQG (amino acid 115 of SEQ ID NO: 16), and the constant region for the light chain starts with amino acid sequence FGQG (amino acid 98 of SEQ ID NO: 18).

Example 6

Epitope Mapping of Anti-GM-CSF Antibody

To map the epitope of GM-CSF to which G9 binds, a series of overlapping peptides were generated that span the length of human GM-CSF (FIG. 14). Briefly, twenty-five overlapping 12-mer peptides encompassing the human GM-CSF sequence (GenBank Accession # AAA52578, residues 14 to 144) were designed to contain 7 amino acid overlaps. Peptides were generated as individual 3.7 mm×3.7 mm spots by solid phase synthesis via attachment of the C-terminus of each peptide to the surface of a derivatized cellulose membrane (SPOTs technology, Sigma Genosys). A standard Western blot analysis was employed to determine which peptides cross-react with G9 (FIG. 15). The cellulose membrane was wetted in methanol and blocked in Blocking Solution (5% BSA, 1×TBS, 0.1% Tween-20, 0.1% NaN$_3$) overnight at 4° C. Fresh Blocking Solution containing 1 mg/ml purified 10G9 antibody was added, and the blot was incubated overnight at 4° C. The blot was washed three times, 5 min each, in TBS-T (1×TBS, 0.1% Tween-20), and incubated for one hour in a 1:10,000 dilution of HRP-conjugated goat anti-human IgG (H+L) (Jackson ImmunoResearch cat. 109-035-088) in diluent (5% BSA, 1×TBS, 0.1% Tween-20). The blot was developed using SuperSignal West Femto ECL Substrate Kit (Pierce cat. 34095), followed by a one second exposure to BioMAX film (Kodak). By this method, peptides #6, 13, 14, 15, and possibly peptide #23 were specifically recognized by the G9 antibody, which correspond to SEQ ID NO: 35, SEQ ID NO: 36, SEQ ID NO: 37, SEQ ID NO: 38, and SEQ ID NO: 39, respectively.

The present invention is not limited to the embodiments described and exemplified above, but is capable of variation and modification within the scope of the appended claims.

Sequence Listing:

SEQ ID NO: 1:
MWLQSLLLLGTVACSISAPARSPSPSTQPWEHVNAIQEARRLLNLSRDTA
AEMNETVEVISEMFDLQEPTCLQTRLELYKQGLRGSLTKLKGPLTMMASH
YKQHCPPTPETSCATQIITFESFKENLKDFLLVIPFDCWEPVQE

Sequence Listing:

SEQ ID NO: 2:
APARSPSPSTQPWEHVNAIQEARRLLNLSRDTAAEMNETVEVISEMFDLQ
EPTCLQTRLELYKQGLRGSLTKLKGPLTMMASHYKQHCPPTPETSCATQI
ITFESFKENLKDFLLVIPFDCWEPVQE

SEQ ID NO: 3: EHVNAIQEARRLLNL

SEQ ID NO: 4: STQPWEHVNAIQEAR

SEQ ID NO: 5: MASHYKQHCPPTPET

SEQ ID NO: 6: LSTAVKELVENSLDAGATNIDLKLKDYGVDLIEVSD
NGCGVEEENFE

SEQ ID NO: 7: LRQVLSNLLDNAIKYTPEGGEITVSLERDGDHLEIT
VEDNGPGIPEEDLE

SEQ ID NO: 8: G9 Predicted Heavy Chain Amino Acid
Sequence
EVQLVESGGGLVQPGGSLRLSCAASGFTFSRHWMHWLRQVPGKGPVWVSR
INGAGTSITYADSVRGRFTISRDNANNTLFLQMNSLRADDTALYFCARAN
SVWFRGLFDYWGQGTPVTVSSASTKGPSVFPLAPSSKSTSGGTAALGCLV
KDYFPEPVTVSWNSGALTSGVHTFPAVLQSSGLYSLSSVVTVPSSSLGTQ
TYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPG
K*

SEQ ID NO: 9: G9 Predicted Heavy Chain Amino Acid
Sequence (w/Leader)
mgwsciilflvatatgvhsEVQLVESGGGLVQPGGSLRLSCAASGFTFSR
HWMHWLRQVPGKGPVWVSRINGAGTSITYADSVRGRFTISRDNANNTLFL
QMNSLRADDTALYFCARANSVWFRGLFDYWGQGTPVTVSSASTKGPSVFP
LAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCP
PCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSV
MHEALHNHYTQKSLSLSPGK*

SEQ ID NO: 10: G9 Heavy Chain Nucleic Acid
Sequence
GAGGTGCAGCTGGTGGAGTCTGGGGGAGGCTTAGTTCAGCCGGGGGGGTC
CCTGAGACTCTCCTGTGCAGCCTCTGGATTCACTTTCAGTAGACACTGGA
TGCACTGGCTTCGCCAGGTTCAGGTAAGGGGCCGGTCTGGGTCTCACGT
ATCAATGGTGCTGGGACTTCCATAACCTACGCGGACTCCGTGAGGGGCCG
ATTCACCATCTCCAGAGACAACGCCAACAACACACTGTTTCTGCAAATGA
ACAGTCTGAGAGCCGACGACACGGCTCTTTATTTCTGTGCAAGAGCGAAC
AGCGTCTGGTTCCGGGGCCTCTTTGACTACTGGGGCCAGGGAACCCCGGT
CACCGTCTCCTCAGCCTCCACCAAGGGCCCATCGGTCTTCCCCCTGGCAC
CCTCCTCCAAGAGCACCTCTGGGGGCACAGCGGCCCTGGGCTGCCTGGTC
AAGGACTACTTCCCCGAACCGGTGACGGTGTCGTGGAACTCAGGCGCCCT
GACCAGCGGCGTGCACACCTTCCCGGCTGTCCTACAGTCCTCAGGACTCT
ACTCCCTCAGCAGCGTGGTGACCGTGCCCTCCAGCAGCTTGGGCACCCAG
ACCTACATCTGCAACGTGAATCACAAGCCCAGCAACACCAAGGTGGACAA
GAAAGTTGAGCCCAAATCTTGTGACAAAACTCACACATGCCCACCGTGCC
CAGCACCTGAACTCCTGGGGGGACCGTCAGTCTTCCTCTTCCCCCCAAAA
CCCAAGGACACCCTCATGATCTCCCGGACCCCTGAGGTCACATGCGTGGT
GGTGGACGTGAGCCACGAAGACCCTGAGGTCAAGTTCAACTGGTACGTGG
ACGGCGTGGAGGTGCATAATGCCAAGACAAAGCCGCGGGAGGAGCAGTAC
AACAGCACGTACCGTGTGGTCAGCGTCCTCACCGTCCTGCACCAGGACTG
GCTGAATGGCAAGGAGTACAAGTGCAAGGTCTCCAACAAAGCCCTCCCAG
CCCCCATCGAGAAAACCATCTCCAAAGCCAAAGGGCAGCCCCGAGAACCA
CAGGTGTACACCCTGCCCCCATCCCGGGATGAGCTGACCAAGAACCAGGT
CAGCCTGACCTGCCTGGTCAAAGGCTTCTATCCCAGCGACATCGCCGTGG
AGTGGGAGAGCAATGGGCAGCCGGAGAACAACTACAAGACCACGCCTCCC
GTGCTGGACTCCGACGGCTCCTTCTTCCTCTACAGCAAGCTCACCGTGGA
CAAGAGCAGGTGGCAGCAGGGGAACGTCTTCTCATGCTCCGTGATGCATG
AGGCTCTGCACAACCACTACACGCAGAAGAGCCTCTCCCTGTCTCCCGGG
AAATGA SEQ ID NO: 11: G9 Heavy Chain Nucleic Acid
Sequence (w/Leader)
aagcttgccgccaccATGGGATGGAGCTGTATCATCCTCTTCTTGGTAGC
AACAGCTACAGGTGTACACAGCGAGGTGCAGCTGGTGGAGTCTGGGGGAG
GCTTAGTTCAGCCGGGGGGGTCCCTGAGACTCTCCTGTGCAGCCTCTGGA
TTCACTTTCAGTAGACACTGGATGCACTGGCTTCGCCAGGTTCAGGTAA
GGGGCCGGTCTGGGTCTCACGTATCAATGGTGCTGGGACTTCCATAACCT
ACGCGGACTCCGTGAGGGGCCGATTCACCATCTCCAGAGACAACGCCAAC
AACACACTGTTTCTGCAAATGAACAGTCTGAGAGCCGACGACACGGCTCT
TTATTTCTGTGCAAGAGCGAACAGCGTCTGGTTCCGGGGCCTCTTTGACT
ACTGGGGCCAGGGAACCCCGGTCACCGTCTCCTCAGCCTCCACCAAGGGC
CCATCGGTCTTCCCCCTGGCACCCTCCTCCAAGAGCACCTCTGGGGGCAC
AGCGGCCCTGGGCTGCCTGGTCAAGGACTACTTCCCCGAACCGGTGACGG
TGTCGTGGAACTCAGGCGCCCTGACCAGCGGCGTGCACACCTTCCCGGCT
GTCCTACAGTCCTCAGGACTCTACTCCCTCAGCAGCGTGGTGACCGTGCC
CTCCAGCAGCTTGGGCACCCAGACCTACATCTGCAACGTGAATCACAAGC
CCAGCAACACCAAGGTGGACAAGAAAGTTGAGCCCAAATCTTGTGACAAA
ACTCACACATGCCCACCGTGCCCAGCACCTGAACTCCTGGGGGGACCGTC
AGTCTTCCTCTTCCCCCCAAAACCCAAGGACACCCTCATGATCTCCCGGA
CCCCTGAGGTCACATGCGTGGTGGTGGACGTGAGCCACGAAGACCCTGAG
GTCAAGTTCAACTGGTACGTGGACGGCGTGGAGGTGCATAATGCCAAGAC
AAAGCCGCGGGAGGAGCAGTACAACAGCACGTACCGTGTGGTCAGCGTCC
TCACCGTCCTGCACCAGGACTGGCTGAATGGCAAGGAGTACAAGTGCAAG
GTCTCCAACAAAGCCCTCCCAGCCCCCATCGAGAAAACCATCTCCAAAGC
CAAAGGGCAGCCCCGAGAACCACAGGTGTACACCCTGCCCCCATCCCGGG
ATGAGCTGACCAAGAACCAGGTCAGCCTGACCTGCCTGGTCAAAGGCTTC
TATCCCAGCGACATCGCCGTGGAGTGGGAGAGCAATGGGCAGCCGGAGAA
CAACTACAAGACCACGCCTCCCGTGCTGGACTCCGACGGCTCCTTCTTCC
TCTACAGCAAGCTCACCGTGGACAAGAGCAGGTGGCAGCAGGGGAACGTC
TTCTCATGCTCCGTGATGCATGAGGCTCTGCACAACCACTACACGCAGAA
GAGCCTCTCCCTGTCTCCCGGGAAATGAgaattc SEQ ID NO: 12: G9 Predicted Light Chain Amino
Acid Sequence
EIVLTQSPVTLSVSPGERVILSCRASQSVSTNLAWYQQKLGQPRLLIYG
ASTRATDIPARFSGSGSETEFTLTISSLQSEDFAVYYCQQYDKWPDTFGQ
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC*

SEQ ID NO: 13: G9 Predicted Light Chain Amino
Acid Sequence (w/Leader)
mgwsciilflvatatgvhsEIVLTQSPVTLSVSPGERVTLSCRASQSVST
NLAWYQQKLGQPRLLIYGASTRATDIPARFSGSGSETEFTLTISSLQSE
DFAVYYCQQYDKWPDTFGQGTKLEIKRTVAAPSVFIFPPSDEQLKSGTAS
VVCLLNNFYPREAKVQWKVDNALQSGNSQESVTEQDSKDSTYSLSSTLTL
SKADYEKHKVYACEVTHQGLSSPVTKSFNRGEC*

SEQ ID NO: 14 G9 Light Chain Nucleic Acid Sequence
GAAATTGTGCTGACTCAGTCTCCAGTCACCCTGTCTGTGTCTCCAGGGGA
AAGAGTCACTCTCTCCTGCAGGGCCAGTCAGAGTGTTAGCACCAACTTAG
CCTGGTATCAGCAGAAACTTGGCCAGGGTCCCAGGCTCCTCATTTATGGT
GCATCCACCAGGGCCACTGATATCCCAGCCAGGTTCAGTGGCAGTGGGTC
TGAGACAGAGTTCACTCTCACCATCAGCAGCCTGCAGTCTGAAGATTTTG
CAGTTTATTACTGTCAGCAATATGATAAGTGGCCGGACACTTTTGGCCAG
GGGACCAAGCTGGAGATCAAACGAACTGTGGCTGCACCATCTGTCTTCAT
CTTCCCGCCATCTGATGAGCAGTTGAAATCTGGAACTGCCTCTGTTGTGT
GCCTGCTGAATAACTTCTATCCCAGAGAGGCCAAAGTACAGTGGAAGGTG
GATAACGCCCTCCAATCGGGTAACTCCCAGGAGAGTGTCACAGAGCAGGA
CAGCAAGGACAGCACCTACAGCCTCAGCAGCACCCTGACGCTGAGCAAAG
CAGACTACGAGAAACACAAAGTCTACGCCTGCGAAGTCACCCATCAGGGC
CTGAGTTCGCCCGTCACAAAGAGCTTCAACAGGGGAGAGTGTTAA SEQ ID NO: 15 G9 Light Chain Nucleic Acid Sequence
(w/Leader)
aagcttgccgccaccATGGGATGGAGCTGTATCATCCTCTTCTTGGTAGC
AACAGCTACAGGTGTACACAGCGAAATTGTGCTGACTCAGTCTCCAGTCA
CCCTGTCTGTGTCTCCAGGGGAAAGAGTCACTCTCTCCTGCAGGGCCAGT
CAGAGTGTTAGCACCAACTTAGCCTGGTATCAGCAGAAACTTGGCCAGGG
TCCCAGGCTCCTCATTTATGGTGCATCCACCAGGGCCACTGATATCCCAG
CCAGGTTCAGTGGCAGTGGGTCTGAGACAGAGTTCACTCTCACCATCAGC
AGCCTGCAGTCTGAAGATTTTGCAGTTTATTACTGTCAGCAATATGATAA
GTGGCCGGACACTTTTGGCCAGGGGACCAAGCTGGAGATCAAACGAACTG
TGGCTGCACCATCTGTCTTCATCTTCCCGCCATCTGATGAGCAGTTGAAA
TCTGGAACTGCCTCTGTTGTGTGCCTGCTGAATAACTTCTATCCCAGAGA
GGCCAAAGTACAGTGGAAGGTGGATAACGCCCTCCAATCGGGTAACTCCC

Sequence Listing:

AGGAGAGTGTCACAGAGCAGGACAGCAAGGACAGCACCTACAGCCTCAGC
AGCACCCTGACGCTGAGCAAAGCAGACTACGAGAAACACAAAGTCTACGC
CTGCGAAGTCACCCATCAGGGCCTGAGTTCGCCCGTCACAAAGAGCTTCA
ACAGGGGAGAGTGTTAAgaattc SEQ ID NO: 16 Predicted E10 Heavy Chain Amino
Acid Sequence
QVQLEESGGGVVQPGRSLRLSCAASGFTFTNYGMHWVRQAPGKGLEWLAL
ISYDGNRQYYADSVKGRFTVSRDNPNNTLHLEMKSLRAEDSAIYYCARGA
GVLLWFGDLSWFDPWGQGTLVIVSSASTKGPSVFPLAPSSKSTSGGTAAL
GCLVKDYFPEPVTVSWNSGALTSGVHTFPAVLQSSGLYSLSSVVTVPSSS
LGTQTYICNVNHKPSNTKVD SEQ ID NO: 17 E10 Heavy Chain Nucleic Acid
Sequence
CAGGTACAGCTGGAGGAGTCAGGGGGAGGCGTGGTCCAGCCTGGGAGGTC
CCTCAGACTCTCCTGTGCAGCGTCTGGATTCACCTTCACTAATTATGGCA
TGCACTGGGTCCGCCAGGCTCCAGGCAAGGGACTCGAGTGGCTGGCACTC
ATATCCTATGATGGAAATAGGCAATACTATGCAGACTCCGTGAAGGGCCG
ATTCACCGTCTCCAGAGACAATCCCAACAACACACTGCATCTGGAGATGA
AGAGCCTGCGAGCCGAAGACTCGGCTATATATTACTGTGCGAGAGGGGCT
GGGGTATTACTGTGGTTCGGCGACTTATCCTGGTTCGACCCCTGGGGCCA
GGGAACCCTGGTCACCGTCTCCTCAGCCTCCACCAAGGGCCCATCGGTCT
TCCCCCTGGCACCCTCCTCCAAGAGCACCTCTGGGGGCACAGCGGCCCTG
GGCTGCCTGGTCAAGGACTACTTCCCCGAACCGGTGACGGTGTCGTGGAA
CTCAGGCGCCCTGACCAGCGGCGTGCACACCTTCCCGGCTGTCCTACAGT
CCTCAGGACTCTACTCCCTCAGCAGCGTGGTGACCGTGCCCTCCAGCAGC
TTGGGCACCCAGACCTACATCTGCAACGTGAATCACAAGCCCAGCAACAC
CAAGGTGGAC SEQ ID NO: 18 Predicted E10 Light Chain Amino Acid
Sequence
DIQMTQSPSNLSASVGDRVTITCRASQNINTWLAWYQHKPGKPPKLRIYQ
ASTLESGVPSRFSGSGSGTIFTLTISSLQPDDFGTYYCQQNNSYPYTFGQ
GTKLEINRTVAAPSVFIFPPSDEQLKSGTASVVCLLNNFYPREAKVQWKV
DNALQSGNSQESVTEQDSMDSTYSLSSTLTLSKADYEKHKVYACEVTHQG
LSSPVTKSFNRGEC SEQ ID NO: 19 E10 Light Chain Nucleic Acid
Sequence
GATATCCAGATGACCCAGTCTCCTTCCAACCTGTCTGCATCTGTAGGAGA
CAGAGTCACAATCACTTGTCGGGCCAGTCAAAATATTAATACCTGGCTGG
CCTGGTATCAGCACAAACCAGGGAAACCCCCTAAGCTCCGGATATATCAG
GCGTCTACGTTAGAAAGTGGGGTCCCTTCAAGGTTCAGCGGCAGTGGATC
TGGGACGATATTCACTCTCACCATCAGCAGCCTGCAGCCTGATGATTTTG
GAACTTATTACTGCCAACAGAATAATAGTTACCCGTACACTTTTGGCCAG
GGGACCAAGCTGGAGATCAACCGAACTGTGGCTGCACCATCTGTCTTCAT
CTTCCCGCCATCTGATGAGCAGTTGAAATCTGGAACTGCCTCTGTTGTGT
GCCTGCTGAATAACTTCTATCCCAGAGAGGCCAAAGTACAGTGGAAGGTG
GATAACGCCCTCCAATCGGGTAACTCCCAGGAGAGTGTCACAGAGCAGGA
CAGCATGGACAGCACCTACAGCCTCAGCAGCACCCTGACGCTGAGCAAAG
CAGACTACGAGAAACACAAAGTCTACGCCTGCGAAGTCACCCATCAGGGC
CTGAGCTCGCCCGTCACAAAGAGCTTCAACAGGGGAGAGTGTTAA

SEQ ID NO: 20: TCACCATCCATTGCACAGTT

SEQ ID NO: 21: CTGCGAGAAGGTACTCACCC

SEQ ID NO: 22: GAHRTYSWGHTGACBCAGTCTCC

SEQ ID NO: 23:
GATCGAATTCTTAACACTCTCCCCTGTTGAAGCTCTTTGTGACGGGCGAG
CTCAGGCC

SEQ ID NO: 24: AGGTRCAGCTGBWGSAGTCDG

SEQ ID NO: 25: GTCCACCTTGGTGTTGCTGGGCTT

SEQ ID NO: 26: AGCGGATAACAATTTCACACAGG

SEQ ID NO: 27: CGCCAGGGTTTTCCCAGTCACGAC

SEQ ID NO: 28:
GATCGGATCCGCCGCCACCATGGGATGGAGCTGTATCATCCTCTTCTTGG
TAGCAACAGCTACAGGTGTACACAGCGAAATTGTGCTGACTCAGTCTCC

SEQ ID NO: 29: GATCGAATTCTCATTTCCCGGGAGACAGGGAGAGG

SEQ ID NO: 30:
GATCGGATCCAAGCTTGCCGCCACCATGGGATGGAGCTGTATCATCCTCT
TCTTGGTAGCAACAGCTACAGGTGTACACAGCGAGGTGCAGCTGGTGGAG
TCTGG

SEQ ID NO: 31: GGACAAGAAAGTTGAGCCCA

SEQ ID NO: 32: TGCAAGGTCTCCAACAAAGC

SEQ ID NO: 33: CCTGGTTCTTGGTCAGCTCA

SEQ ID NO: 34: GGCACGGTGGGCATGTGTGA

SEQ ID NO: 35: ARRLLNLSRDTA

SEQ ID NO: 36: TRLELYKQGLRG

SEQ ID NO: 37: YKQGLRGSLTKL

SEQ ID NO: 38: RGSLTKLKGPLT

SEQ ID NO: 39: KENLKDFLLVIP (G9 H CDR1)
SEQ ID NO: 40
GFTFSRHWMH (G9 H CDR2)
SEQ ID NO: 41
RINGAGTSITYADSVRG (G9 H CDR3)
SEQ ID NO: 42
ANSVWFRGLFDY (G9 L CDR1)
SEQ ID NO: 43
RASQSVSTNLA (G9 L CDR2)
SEQ ID NO: 44
GASTRAT (G9 L CDR3)
SEQ ID NO: 45
QQYDKWPDT (E10 H CDR1)
SEQ ID NO: 46
GFTFTNYGMH (E10 H CDR2)
SEQ ID NO: 47
LISYDGNRQYYADSVKG (E10 H CDR3)
SEQ ID NO: 48
GAGVLLWFGDLSWFDP (E10 L CDR1)
SEQ ID NO: 49
RASQNINTWLA (E10 L CDR2)
SEQ ID NO: 50
QASTLES (E10 L CDR3)
SEQ ID NO: 51
QQNNSYPYT (G9 H FWR1)
SEQ ID NO: 52
EVQLVESGGGLVQPGGSLRLSCAAS

| | |
|---|---|
| (G9 H FWR2) | SEQ ID NO: 53 |
| WLRQVPGKGPVWVS | |
| (G9 H FWR3) | SEQ ID NO: 54 |
| RFTISRDNANNTLFLQMNSLRADDTALYFCAR | |
| (G9 L FWR1) | SEQ ID NO: 55 |
| EIVLTQSPVTLSVSPGERVTLSC | |
| (G9 L FWR2) | SEQ ID NO: 56 |
| WYQQKLGQGPRLLIY | |
| (G9 L FWR3) | SEQ ID NO: 57 |
| DIPARFSGSGSETEFTLTISSLQSEDFAVYYC | |
| (E10 H FWR1) | SEQ ID NO: 58 |
| QVQLEESGGGVVQPGRSLRLSCAAS | |
| (E10 H FWR2) | SEQ ID NO: 59 |
| WVRQAPGKGLEWLA | |
| (E10 H FWR3) | SEQ ID NO: 60 |
| RFTVSRDNPNNTLHLEMKSLRAEDSAIYYCAR | |
| (E10 L FWR1) | SEQ ID NO: 61 |
| DIQMTQSPSNLSASVGDRVTITC | |
| (E10 L FWR2) | SEQ ID NO: 62 |
| WYQHKPGKPPKLRIY | |
| (E10 L FWR3) | SEQ ID NO: 63 |
| GVPSRFSGSGSGTIFTLTISSLQPDDFGTYYC | |

What is claimed:

1. A recombinant polynucleotide encoding the heavy and/or light chain of an antibody that specifically binds to granulocyte-macrophage colony stimulating factor (GM-CSF), wherein said antibody comprises a heavy chain comprising a CDR1 of SEQ ID NO: 40, a CDR2 of SEQ ID NO: 41, and a CDR3 of SEQ ID NO: 42 and a light chain comprising a CDR1 of SEQ ID NO: 43, a CDR2 of SEQ ID NO: 44, and a CDR3 of SEQ ID NO: 45.

2. A recombinant polynucleotide encoding the heavy and/or light chain of an antibody that binds to granulocyte-macrophage colony stimulating factor (GM-CSF), said antibody comprising the six complementarity determining regions of the antibody produced by the cell assigned ATCC Accession No. PTA-8173.

3. A vector comprising the polynucleotide of claim 1.

4. A vector comprising the polynucleotide of claim 2.

5. An isolated cell that recombinantly expresses an antibody that specifically binds to granulocyte-macrophage colony stimulating factor (GM-CSF), wherein said antibody comprises a heavy chain comprising a CDR1 of SEQ ID NO: 40, a CDR2 of SEQ ID NO: 41, and a CDR3 of SEQ ID NO: 42 and a light chain comprising a CDR1 of SEQ ID NO: 43, a CDR2 of SEQ ID NO: 44, and a CDR3 of SEQ ID NO: 45.

6. An isolated cell that recombinantly expresses an antibody that binds to granulocyte-macrophage colony stimulating factor (GM-CSF), said antibody comprising the six complementarity determining regions of the antibody produced by the cell assigned ATCC Accession No. PTA-8173.

7. An isolated hybridoma cell that expresses a monoclonal antibody that specifically binds to granulocyte-macrophage colony stimulating factor (GM-CSF), wherein said antibody comprises a heavy chain comprising a CDR1 of SEQ ID NO: 40, a CDR2 of SEQ ID NO: 41, and a CDR3 of SEQ ID NO: 42 and a light chain comprising a CDR1 of SEQ ID NO: 43, a CDR2 of SEQ ID NO: 44, and a CDR3 of SEQ ID NO: 45.

8. An isolated hybridoma cell that expresses a monoclonal antibody that binds to granulocyte-macrophage colony stimulating factor (GM-CSF), said antibody comprising the six complementarity determining regions of the antibody produced by the cell assigned ATCC Accession No. PTA-8173.

* * * * *

SEQUENCE LISTING

```
<160> NUMBER OF SEQ ID NOS: 86

<210> SEQ ID NO 1
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 1

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
        50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 2
<211> LENGTH: 127
<212> TYPE: PRT
<213> ORGANISM: Artificial Sequence
<220> FEATURE:
<223> OTHER INFORMATION: Description of Artificial Sequence: Synthetic
```

-continued polypeptide construct

<400> SEQUENCE: 2

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 3

Glu His Val Asn Ala Ile Gln Glu Ala Arg Arg Leu Leu Asn Leu
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 4

Ser Thr Gln Pro Trp Glu His Val Asn Ala Ile Gln Glu Ala Arg
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 5

Met Ala Ser His Tyr Lys Gln His Cys Pro Pro Thr Pro Glu Thr
1               5                   10                  15

<210> SEQ ID NO 6
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 6

Leu Ser Thr Ala Val Lys Glu Leu Val Glu Asn Ser Leu Asp Ala Gly
1               5                   10                  15

Ala Thr Asn Ile Asp Leu Lys Leu Lys Asp Tyr Gly Val Asp Leu Ile
            20                  25                  30

Glu Val Ser Asp Asn Gly Cys Gly Val Glu Glu Glu Asn Phe Glu
        35                  40                  45

<210> SEQ ID NO 7
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 7

Leu Arg Gln Val Leu Ser Asn Leu Leu Asp Asn Ala Ile Lys Tyr Thr
1               5                   10                  15

Pro Glu Gly Gly Glu Ile Thr Val Ser Leu Glu Arg Asp Gly Asp His
            20                  25                  30

Leu Glu Ile Thr Val Glu Asp Asn Gly Pro Gly Ile Pro Glu Glu Asp
        35                  40                  45

Leu Glu
    50

<210> SEQ ID NO 8
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg His
            20                  25                  30

Trp Met His Trp Leu Arg Gln Val Pro Gly Lys Gly Pro Val Trp Val
        35                  40                  45

Ser Arg Ile Asn Gly Ala Gly Thr Ser Ile Thr Tyr Ala Asp Ser Val
    50                  55                  60

Arg Gly Arg Phe Thr Ile Ser Arg Asp Asn Ala Asn Asn Thr Leu Phe
65                  70                  75                  80

Leu Gln Met Asn Ser Leu Arg Ala Asp Asp Thr Ala Leu Tyr Phe Cys
                85                  90                  95

Ala Arg Ala Asn Ser Val Trp Phe Arg Gly Leu Phe Asp Tyr Trp Gly
            100                 105                 110

Gln Gly Thr Pro Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val

```
                180                 185                 190
Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 9
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 9

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Arg His Trp Met His Trp Leu Arg Gln Val Pro Gly Lys Gly Pro
    50                  55                  60

Val Trp Val Ser Arg Ile Asn Gly Ala Gly Thr Ser Ile Thr Tyr Ala
65                  70                  75                  80
```

```
Asp Ser Val Arg Gly Arg Phe Thr Ile Ser Arg Asp Asn Ala Asn Asn
             85                  90                  95

Thr Leu Phe Leu Gln Met Asn Ser Leu Arg Ala Asp Asp Thr Ala Leu
        100                 105                 110

Tyr Phe Cys Ala Arg Ala Asn Ser Val Trp Phe Arg Gly Leu Phe Asp
            115                 120                 125

Tyr Trp Gly Gln Gly Thr Pro Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
450                 455                 460

Ser Leu Ser Pro Gly Lys
465                 470

<210> SEQ ID NO 10
<211> LENGTH: 1356
<212> TYPE: DNA
```

<213> ORGANISM: Artificial Sequence
<220> FEATURE:
<223> OTHER INFORMATION: Description of Artificial Sequence: Synthetic polynucleotide construct

<400> SEQUENCE: 10

```
gaggtgcagc tggtggagtc tgggggaggc ttagttcagc cggggggtc cctgagactc      60
tcctgtgcag cctctggatt cactttcagt agacactgga tgcactggct tcgccaggtt    120
ccaggtaagg ggccggtctg gtctcacgt atcaatggtg ctgggacttc cataacctac     180
gcggactccg tgaggggccg attcaccatc tccagagaca acgccaacaa cacactgttt    240
ctgcaaatga acagtctgag agccgacgac acggctcttt atttctgtgc aagagcgaac    300
agcgtctggt tccggggcct ctttgactac tggggccagg gaaccccggt caccgtctcc    360
tcagcctcca ccaagggccc atcggtcttc cccctggcac cctcctccaa gagcacctct    420
gggggcacag cggccctggg ctgcctggtc aaggactact ccccgaacc ggtgacggtg     480
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gaaagttgag    660
cccaaatctt gtgacaaaac tcacacatgc ccaccgtgcc cagcacctga actcctgggg    720
ggaccgtcag tcttcctctt ccccccaaaa cccaaggaca cctcatgat ctcccggacc     780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca gtgcaaggt ctccaacaaa gccctcccag cccccatcga gaaaaccatc    1020
tccaaagcca agggcagcc cgagaaccag caggtgtaca ccctgccccc atcccgggat   1080
gagctgacca agaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctcccggg aaatga                             1356
```

<210> SEQ ID NO 11
<211> LENGTH: 1434
<212> TYPE: DNA
<213> ORGANISM: Artificial Sequence
<220> FEATURE:
<223> OTHER INFORMATION: Description of Artificial Sequence: Synthetic polynucleotide construct

<400> SEQUENCE: 11

```
aagcttgccg ccaccatggg atggagctgt atcatcctct tcttggtagc aacagctaca      60
ggtgtacaca gcgaggtgca gctggtggag tctgggggag gcttagttca gccgggggg     120
tccctgagac tctcctgtgc agcctctgga ttcactttca gtagacactg gatgcactgg    180
cttcgccagg ttccaggtaa ggggccggtc tgggtctcac gtatcaatgg tgctgggact    240
tccataacct acgcggactc cgtgaggggc cgattcacca tctccagaga caacgccaac    300
aacacactgt ttctgcaaat gaacagtctg agagccgacg acacggctct ttatttctgt    360
gcaagagcga acagcgtctg gttccggggc ctctttgact actggggcca gggaaccccg    420
gtcaccgtct cctcagcctc caccaagggc ccatcggtct tccccctggc accctcctcc    480
```

```
aagagcacct ctgggggcac agcggccctg ggctgcctgg tcaaggacta cttccccgaa    540
ccggtgacgg tgtcgtggaa ctcaggcgcc ctgaccagcg gcgtgcacac cttcccggct    600
gtcctacagt cctcaggact ctactccctc agcagcgtgg tgaccgtgcc ctccagcagc    660
ttgggcaccc agacctacat ctgcaacgtg aatcacaagc ccagcaacac caaggtggac    720
aagaaagttg agcccaaatc ttgtgacaaa actcacacat gcccaccgtg cccagcacct    780
gaactcctgg ggggaccgtc agtcttcctc ttccccccaa aacccaagga caccctcatg    840
atctcccgga cccctgaggt cacatgcgtg gtggtggacg tgagccacga agaccctgag    900
gtcaagttca actggtacgt ggacggcgtg gaggtgcata atgccaagac aaagccgcgg    960
gaggagcagt acaacagcac gtaccgtgtg gtcagcgtcc tcaccgtcct gcaccaggac   1020
tggctgaatg gcaaggagta caagtgcaag gtctccaaca aagccctccc agcccccatc   1080
gagaaaacca tctccaaagc caaagggcag ccccgagaac acaggtgta caccctgccc   1140 ccatcccggg atgagctgac caagaaccag gtcagcctga cctgcctggt caaaggcttc   1200
tatcccagcg acatcgccgt ggagtgggag agcaatgggc agccggagaa caactacaag   1260
accacgcctc ccgtgctgga ctccgacggc tccttcttcc tctacagcaa gctcaccgtg   1320
gacaagagca ggtggcagca ggggaacgtc ttctcatgct ccgtgatgca tgaggctctg   1380
cacaaccact acacgcagaa gagcctctcc ctgtctcccg ggaaatgaga attc          1434
```

<210> SEQ ID NO 12
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 12

```
Glu Ile Val Leu Thr Gln Ser Pro Val Thr Leu Ser Val Ser Pro Gly
1               5                   10                  15

Glu Arg Val Thr Leu Ser Cys Arg Ala Ser Gln Ser Val Ser Thr Asn
            20                  25                  30

Leu Ala Trp Tyr Gln Gln Lys Leu Gly Gln Gly Pro Arg Leu Leu Ile
        35                  40                  45

Tyr Gly Ala Ser Thr Arg Ala Thr Asp Ile Pro Ala Arg Phe Ser Gly
    50                  55                  60

Ser Gly Ser Glu Thr Glu Phe Thr Leu Thr Ile Ser Ser Leu Gln Ser
65                  70                  75                  80

Glu Asp Phe Ala Val Tyr Tyr Cys Gln Gln Tyr Asp Lys Trp Pro Asp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 13

Met Gly Trp Ser Cys Ile Ile Leu Phe Leu Val Ala Thr Ala Thr Gly
1               5                   10                  15

Val His Ser Glu Ile Val Leu Thr Gln Ser Pro Val Thr Leu Ser Val
            20                  25                  30

Ser Pro Gly Glu Arg Val Thr Leu Ser Cys Arg Ala Ser Gln Ser Val
        35                  40                  45

Ser Thr Asn Leu Ala Trp Tyr Gln Gln Lys Leu Gly Gln Gly Pro Arg
    50                  55                  60

Leu Leu Ile Tyr Gly Ala Ser Thr Arg Ala Thr Asp Ile Pro Ala Arg
65                  70                  75                  80

Phe Ser Gly Ser Gly Ser Glu Thr Glu Phe Thr Leu Thr Ile Ser Ser
                85                  90                  95

Leu Gln Ser Glu Asp Phe Ala Val Tyr Tyr Cys Gln Gln Tyr Asp Lys
            100                 105                 110

Trp Pro Asp Thr Phe Gly Gln Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 14
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 14
gaaattgtgc tgactcagtc tccagtcacc ctgtctgtgt ctccagggga aagagtcact      60
ctctcctgca gggccagtca gagtgttagc accaacttag cctggtatca gcagaaactt     120
ggccagggtc ccaggctcct catttatggt gcatccacca gggccactga tatcccagcc    180

```
aggttcagtg gcagtgggtc tgagacagag ttcactctca ccatcagcag cctgcagtct        240
gaagattttg cagtttatta ctgtcagcaa tatgataagt ggccggacac ttttggccag        300
gggaccaagc tggagatcaa acgaactgtg ctgcaccat ctgtcttcat cttcccgcca         360
tctgatgagc agttgaaatc tggaactgcc tctgttgtgt gcctgctgaa taacttctat        420
cccagagagg ccaaagtaca gtggaaggtg ataacgccc tccaatcggg taactcccag         480
gagagtgtca cagagcagga cagcaaggac agcacctaca gcctcagcag caccctgacg        540
ctgagcaaag cagactacga aaacacaaa gtctacgcct gcgaagtcac ccatcagggc         600
ctgagttcgc ccgtcacaaa gagcttcaac aggggagagt gttaa                       645
```

<210> SEQ ID NO 15
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 15

```
aagcttgccg ccaccatggg atggagctgt atcatcctct tcttggtagc aacagctaca         60
ggtgtacaca gcgaaattgt gctgactcag tctccagtca ccctgtctgt gtctccaggg        120
gaaagagtca ctctctcctg cagggccagt cagagtgtta gcaccaactt agcctggtat        180
cagcagaaac ttggccaggg tcccaggctc ctcatttatg gtgcatccac cagggccact        240
gatatcccag ccaggttcag tggcagtggg tctgagacag agttcactct caccatcagc        300
agcctgcagt ctgaagattt tgcagtttat tactgtcagc aatatgataa gtggccggac        360
acttttggcc aggggaccaa gctggagatc aaacgaactg tggctgcacc atctgtcttc        420
atcttcccgc catctgatga gcagttgaaa tctggaactg cctctgttgt gtgcctgctg        480
aataacttct atcccagaga ggccaaagta cagtggaagg tggataacgc cctccaatcg        540
ggtaactccc aggagagtgt cacagagcag gacagcaagg acagcaccta cagcctcagc        600
agcaccctga cgctgagcaa agcagactac gaaaacacaa agtctacgc ctgcgaagtc        660 acccatcagg gcctgagttc gcccgtcaca aagagcttca caggggaga gtgttaagaa       720 ttc                                                                    723
```

<210> SEQ ID NO 16
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 16

```
Gln Val Gln Leu Glu Glu Ser Gly Gly Gly Val Val Gln Pro Gly Arg
1               5                   10                  15

Ser Leu Arg Leu Ser Cys Ala Ala Ser Gly Phe Thr Phe Thr Asn Tyr
            20                  25                  30

Gly Met His Trp Val Arg Gln Ala Pro Gly Lys Gly Leu Glu Trp Leu
        35                  40                  45

Ala Leu Ile Ser Tyr Asp Gly Asn Arg Gln Tyr Tyr Ala Asp Ser Val
    50                  55                  60

Lys Gly Arg Phe Thr Val Ser Arg Asp Asn Pro Asn Asn Thr Leu His
65                  70                  75                  80
```

Leu Glu Met Lys Ser Leu Arg Ala Glu Asp Ser Ala Ile Tyr Tyr Cys
            85                  90                  95

Ala Arg Gly Ala Gly Val Leu Leu Trp Phe Gly Asp Leu Ser Trp Phe
        100                 105                 110

Asp Pro Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp
    210                 215                 220

<210> SEQ ID NO 17
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 17
caggtacagc tggaggagtc agggggaggc gtggtccagc ctggaggtc cctcagactc      60 tcctgtgcag cgtctggatt caccttcact aattatggca tgcactgggt ccgccaggct    120
ccaggcaagg gactcgagtg gctggcactc atatcctatg atggaaatag caatactat    180 gcagactccg tgaagggccg attcaccgtc tccagagaca tcccaacaa cacactgcat    240 ctggagatga gagcctgcg agccgaagac tcggctatat attactgtgc gagaggggct    300
ggggtattac tgtggttcgg cgacttatcc tggttcgacc cctggggcca gggaaccctg    360
gtcaccgtct cctcagcctc caccaagggc ccatcggtct tccccctggc acctcctcc     420 aagagcacct ctgggggcac agcggccctg ggctgcctgg tcaaggacta cttccccgaa    480
ccggtgacgg tgtcgtggaa ctcaggcgcc ctgaccagcg gcgtgcacac cttcccggct    540
gtcctacagt cctcaggact ctactccctc agcagcgtgg tgaccgtgcc ctccagcagc    600
ttgggcaccc agacctacat ctgcaacgtg aatcacaagc ccagcaacac caaggtggac    660

<210> SEQ ID NO 18
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 18

Asp Ile Gln Met Thr Gln Ser Pro Ser Asn Leu Ser Ala Ser Val Gly
1               5                   10                  15

Asp Arg Val Thr Ile Thr Cys Arg Ala Ser Gln Asn Ile Asn Thr Trp
            20                  25                  30

Leu Ala Trp Tyr Gln His Lys Pro Gly Lys Pro Pro Lys Leu Arg Ile

```
                    35                  40                  45
Tyr Gln Ala Ser Thr Leu Glu Ser Gly Val Pro Ser Arg Phe Ser Gly
         50                  55                  60

Ser Gly Ser Gly Thr Ile Phe Thr Leu Thr Ile Ser Ser Leu Gln Pro
 65                  70                  75                  80

Asp Asp Phe Gly Thr Tyr Tyr Cys Gln Gln Asn Asn Ser Tyr Pro Tyr
                 85                  90                  95

Thr Phe Gly Gln Gly Thr Lys Leu Glu Ile Asn Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Met Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 19
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 19

```
gatatccaga tgacccagtc tccttccaac ctgtctgcat ctgtaggaga cagagtcaca    60
atcacttgtc gggccagtca aaatattaat acctggctgg cctggtatca gcacaaacca   120
gggaaacccc ctaagctccg gatatatcag gcgtctacgt tagaaagtgg ggtcccttca   180
aggttcagcg gcagtggatc tgggacgata ttcactctca ccatcagcag cctgcagcct   240
gatgattttg gaacttatta ctgccaacag aataatagtt acccgtacac ttttggccag   300
gggaccaagc tggagatcaa ccgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcatggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gttaa                   645
```

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tcaccatcca ttgcacagtt                                              20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ctgcgagaag gtactcaccc                                              20

<210> SEQ ID NO 22
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 22

Gly Ala His Arg Thr Tyr Ser Trp Gly His Thr Gly Ala Cys Asx Cys
1               5                   10                  15

Ala Gly Thr Cys Thr Cys Cys
            20

<210> SEQ ID NO 23
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gatcgaattc ttaacactct cccctgttga agctctttgt gacgggcgag ctcaggcc    58

<210> SEQ ID NO 24
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 24

Ala Gly Gly Thr Arg Cys Ala Gly Cys Thr Gly Asx Trp Gly Ser Ala
1               5                   10                  15

Gly Thr Cys Asp Gly
            20

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gtccaccttg gtgttgctgg gctt                                         24

<210> SEQ ID NO 26
<211> LENGTH: 23
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 26
agcggataac aatttcacac agg                                          23

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cgccagggtt ttcccagtca cgac                                         24

<210> SEQ ID NO 28
<211> LENGTH: 99
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gatcggatcc gccgccacca tgggatggag ctgtatcatc ctcttcttgg tagcaacagc   60
tacaggtgta cacagcgaaa ttgtgctgac tcagtctcc                          99

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gatcgaattc tcatttcccg ggagacaggg agagg                             35

<210> SEQ ID NO 30
<211> LENGTH: 105
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gatcggatcc aagcttgccg ccaccatggg atggagctgt atcatcctct tcttggtagc   60
aacagctaca ggtgtacaca gcgaggtgca gctggtggag tctgg                  105

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggacaagaaa gttgagccca                                              20
```

```
<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tgcaaggtct ccaacaaagc                                                   20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cctggttctt ggtcagctca                                                   20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ggcacggtgg gcatgtgtga                                                   20

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 35

Ala Arg Arg Leu Leu Asn Leu Ser Arg Asp Thr Ala
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 36

Thr Arg Leu Glu Leu Tyr Lys Gln Gly Leu Arg Gly
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 37

Tyr Lys Gln Gly Leu Arg Gly Ser Leu Thr Lys Leu
1               5                   10
```

```
<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 38

Arg Gly Ser Leu Thr Lys Leu Lys Gly Pro Leu Thr
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 39

Lys Glu Asn Leu Lys Asp Phe Leu Leu Val Ile Pro
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 40

Gly Phe Thr Phe Ser Arg His Trp Met His
1               5                   10

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 41

Arg Ile Asn Gly Ala Gly Thr Ser Ile Thr Tyr Ala Asp Ser Val Arg
1               5                   10                  15

Gly

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 42

Ala Asn Ser Val Trp Phe Arg Gly Leu Phe Asp Tyr
1               5                   10

<210> SEQ ID NO 43
<211> LENGTH: 11
<212> TYPE: PRT
<213> ORGANISM: Artificial Sequence
<220> FEATURE:
```

```
<223> OTHER INFORMATION: Description of Artificial Sequence: Synthetic
      peptide construct

<400> SEQUENCE: 43

Arg Ala Ser Gln Ser Val Ser Thr Asn Leu Ala
1               5                   10

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 44

Gly Ala Ser Thr Arg Ala Thr
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 45

Gln Gln Tyr Asp Lys Trp Pro Asp Thr
1               5

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 46

Gly Phe Thr Phe Thr Asn Tyr Gly Met His
1               5                   10

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 47

Leu Ile Ser Tyr Asp Gly Asn Arg Gln Tyr Tyr Ala Asp Ser Val Lys
1               5                   10                  15

Gly

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 48

Gly Ala Gly Val Leu Leu Trp Phe Gly Asp Leu Ser Trp Phe Asp Pro
1               5                   10                  15
```

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 49

Arg Ala Ser Gln Asn Ile Asn Thr Trp Leu Ala
1               5                   10

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 50

Gln Ala Ser Thr Leu Glu Ser
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 51

Gln Gln Asn Asn Ser Tyr Pro Tyr Thr
1               5

<210> SEQ ID NO 52
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 53

Trp Leu Arg Gln Val Pro Gly Lys Gly Pro Val Trp Val Ser
1               5                   10

<210> SEQ ID NO 54
<211> LENGTH: 32
<212> TYPE: PRT
<213> ORGANISM: Artificial Sequence

```
<220> FEATURE:
<223> OTHER INFORMATION: Description of Artificial Sequence: Synthetic
      polypeptide construct

<400> SEQUENCE: 54

Arg Phe Thr Ile Ser Arg Asp Asn Ala Asn Asn Thr Leu Phe Leu Gln
1               5                  10                  15

Met Asn Ser Leu Arg Ala Asp Asp Thr Ala Leu Tyr Phe Cys Ala Arg
            20                  25                  30

<210> SEQ ID NO 55
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 55

Glu Ile Val Leu Thr Gln Ser Pro Val Thr Leu Ser Val Ser Pro Gly
1               5                  10                  15

Glu Arg Val Thr Leu Ser Cys
            20

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 56

Trp Tyr Gln Gln Lys Leu Gly Gln Gly Pro Arg Leu Leu Ile Tyr
1               5                  10                  15

<210> SEQ ID NO 57
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 57

Asp Ile Pro Ala Arg Phe Ser Gly Ser Gly Ser Glu Thr Glu Phe Thr
1               5                  10                  15

Leu Thr Ile Ser Ser Leu Gln Ser Glu Asp Phe Ala Val Tyr Tyr Cys
            20                  25                  30

<210> SEQ ID NO 58
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 58

Gln Val Gln Leu Glu Glu Ser Gly Gly Gly Val Val Gln Pro Gly Arg
1               5                  10                  15

Ser Leu Arg Leu Ser Cys Ala Ala Ser
            20                  25

<210> SEQ ID NO 59
```

<211> LENGTH: 14
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 59

Trp Val Arg Gln Ala Pro Gly Lys Gly Leu Glu Trp Leu Ala
1               5                   10

<210> SEQ ID NO 60
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 60

Arg Phe Thr Val Ser Arg Asp Asn Pro Asn Asn Thr Leu His Leu Glu
1               5                   10                  15

Met Lys Ser Leu Arg Ala Glu Asp Ser Ala Ile Tyr Tyr Cys Ala Arg
            20                  25                  30

<210> SEQ ID NO 61
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 61

Asp Ile Gln Met Thr Gln Ser Pro Ser Asn Leu Ser Ala Ser Val Gly
1               5                   10                  15

Asp Arg Val Thr Ile Thr Cys
            20

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 62

Trp Tyr Gln His Lys Pro Gly Lys Pro Pro Lys Leu Arg Ile Tyr
1               5                   10                  15

<210> SEQ ID NO 63
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 63

Gly Val Pro Ser Arg Phe Ser Gly Ser Gly Ser Gly Thr Ile Phe Thr
1               5                   10                  15

Leu Thr Ile Ser Ser Leu Gln Pro Asp Asp Phe Gly Thr Tyr Tyr Cys
            20                  25                  30

<210> SEQ ID NO 64

```
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 64

Cys Ser Ile Ser Ala Pro Ala Arg Ser Pro Ser Pro Ser Thr Gln Pro
1               5                   10                  15

Trp Glu His Val Asn Ala Ile Gln Glu Ala Arg Arg Leu Leu Asn Leu
            20                  25                  30

Ser Arg Asp Thr Ala Ala Glu Met Asn Glu Thr Val Glu Val Ile Ser
        35                  40                  45

Glu Met Phe Asp Leu Gln Glu Pro Thr Cys Leu Gln Thr Arg Leu Glu
    50                  55                  60

Leu Tyr Lys Gln Gly Leu Arg Gly Ser Leu Thr Lys Leu Lys Gly Pro
65                  70                  75                  80

Leu Thr

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 65

Cys Ser Ile Ser Ala Pro Ala Arg Ser Pro Ser Pro
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 66

Pro Ala Arg Ser Pro Ser Pro Ser Thr Gln Pro Trp
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 67

Ser Pro Ser Thr Gln Pro Trp Glu His Val Asn Ala
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 68
```

Pro Trp Glu His Val Asn Ala Ile Gln Glu Ala Arg
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 69

Asn Ala Ile Gln Glu Ala Arg Arg Leu Leu Asn Leu
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 70

Asn Leu Ser Arg Asp Thr Ala Ala Glu Met Asn Glu
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 71

Thr Ala Ala Glu Met Asn Glu Thr Val Glu Val Ile
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 72

Asn Glu Thr Val Glu Val Ile Ser Glu Met Phe Asp
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 73

Val Ile Ser Glu Met Phe Asp Leu Gln Glu Pro Thr
1               5                   10

<210> SEQ ID NO 74
<211> LENGTH: 12
<212> TYPE: PRT
<213> ORGANISM: Artificial Sequence
<220> FEATURE:

```
<223> OTHER INFORMATION: Description of Artificial Sequence: Synthetic
      peptide construct

<400> SEQUENCE: 74

Phe Asp Leu Gln Glu Pro Thr Cys Leu Gln Thr Arg
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 75

Pro Thr Cys Leu Gln Thr Arg Leu Glu Leu Tyr Lys
1               5                   10

<210> SEQ ID NO 76
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 76

Lys Leu Lys Gly Pro Leu Thr Met Met Ala Ser His Tyr Lys Gln His
1               5                   10                  15

Cys Pro Pro Thr Pro Glu Thr Ser Cys Ala Thr Gln Ile Ile Thr Phe
            20                  25                  30

Glu Ser Phe Lys Glu Asn Leu Lys Asp Phe Leu Leu Val Ile Pro Phe
        35                  40                  45

Asp Cys Trp Glu Pro Val Gln Glu
    50                  55

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 77

Lys Leu Lys Gly Pro Leu Thr Met Met Ala Ser His
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 78

Leu Thr Met Met Ala Ser His Tyr Lys Gln His Cys
1               5                   10

<210> SEQ ID NO 79
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide construct

<400> SEQUENCE: 79

Ser His Tyr Lys Gln His Cys Pro Pro Thr Pro Glu
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 80

His Cys Pro Pro Thr Pro Glu Thr Ser Cys Ala Thr
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 81

Pro Glu Thr Ser Cys Ala Thr Gln Ile Ile Thr Phe
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 82

Ala Thr Gln Ile Ile Thr Phe Glu Ser Phe Lys Glu
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 83

Thr Phe Glu Ser Phe Lys Glu Asn Leu Lys Asp Phe
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 84

Asp Phe Leu Leu Val Ile Pro Phe Asp Cys Trp Glu
1               5                   10
```

```
<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 85

Ile Pro Phe Asp Cys Trp Glu Pro Val Gln Glu
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 86

Gly Glu Gln Lys Leu Ile Ser Glu Glu Asp Cys Gly
1               5                   10
```